US008728795B2

(12) United States Patent
Kröger et al.

(10) Patent No.: US 8,728,795 B2
(45) Date of Patent: May 20, 2014

(54) PGRO EXPRESSION UNITS

(75) Inventors: Burkhard Kröger, Limburgerhof (DE); Oskar Zelder, Speyer (DE); Corinna Klopprogge, Mannheim (DE); Hartwig Schröder, Nussloch (DE); Stefan Haefner, Speyer (DE)

(73) Assignee: BASF SE, Ludwigshafen (DE)

(*) Notice: Subject to any disclaimer, the term of this patent is extended or adjusted under 35 U.S.C. 154(b) by 853 days.

(21) Appl. No.: 12/038,642

(22) Filed: Feb. 27, 2008

(65) Prior Publication Data

US 2008/0286841 A1 Nov. 20, 2008

Related U.S. Application Data

(62) Division of application No. 10/582,822, filed as application No. PCT/EP2004/014263 on Dec. 18, 2004, now abandoned.

(30) Foreign Application Priority Data

Dec. 18, 2003 (DE) .................................... 10359595

(51) Int. Cl.
*C12N 1/21* (2006.01)
*C12N 15/77* (2006.01)

(52) U.S. Cl.
USPC ........................................ 435/252.3; 435/471

(58) Field of Classification Search
None
See application file for complete search history.

(56) References Cited

U.S. PATENT DOCUMENTS

| | | | |
|---|---|---|---|
| 4,489,160 | A | 12/1984 | Katsumata et al. |
| 4,601,893 | A | 7/1986 | Cardinal |
| 5,158,891 | A | 10/1992 | Takeda et al. |
| 5,175,108 | A | 12/1992 | Bachmann et al. |
| 5,759,610 | A | 6/1998 | Nishimoto et al. |
| 5,824,837 | A | 10/1998 | Chen et al. |
| 5,965,391 | A | 10/1999 | Reinscheid et al. |
| 6,238,896 | B1 | 5/2001 | Ozaki et al. |
| 6,921,651 | B2 | 7/2005 | Farwick et al. |
| 7,313,177 | B2 | 12/2007 | Radjassamy |
| 2002/0197605 | A1 | 12/2002 | Nakagawa et al. |
| 2003/0049804 | A1 | 3/2003 | Pompejus et al. |
| 2003/0092137 | A1 | 5/2003 | Farwick et al. |
| 2003/0162267 | A1 | 8/2003 | Pompejus et al. |
| 2003/0175503 | A1 | 9/2003 | Lucast et al. |
| 2004/0043953 | A1 | 3/2004 | Pompejus et al. |
| 2004/0180408 | A1 | 9/2004 | Pompejus et al. |

FOREIGN PATENT DOCUMENTS

| | | | |
|---|---|---|---|
| DE | 4440118 | C1 | 11/1995 |
| DE | 10112992 | A1 | 9/2002 |
| EP | 0472869 | B1 | 3/1992 |
| EP | 1108790 | A2 | 6/2001 |
| JP | 10229891 | A | 9/1998 |
| WO | WO-96/15246 | A1 | 5/1996 |
| WO | WO-01/00804 | A2 | 1/2001 |
| WO | WO-01/00842 | A2 | 1/2001 |
| WO | WO-01/00843 | A2 | 1/2001 |
| WO | WO-01/00844 | A2 | 1/2001 |
| WO | WO-02/29029 | A2 | 4/2002 |
| WO | WO-02/40679 | A2 | 5/2002 |
| WO | WO-02/051231 | A1 | 7/2002 |

OTHER PUBLICATIONS

Gupta, R. S., "Evolution of the Chaperonin Families (Hsp60, Hsp10 and Tcp-1) of Proteins and the Origin of Eukaryotic Cells", Molecular Microbiology, vol. 15, No. 1, (1995), pp. 1-11.
Kalinowski, J., et al., "The Complete *Corynebacterium glutamicum* ATCC 13032 Genome Sequence and Its Impact on the Production of L-aspartate-derived Amino Acids and Vitamins", Journal of Biotechnology, vol. 104, (2003), pp. 5-25.
"*Corynebacterium glutamicum* ATCC 13032 DNA, Complete Genome, Section 10/10", GenBank Database, Accession No. AP005283, Aug. 8, 2002.
Reinscheid, D. J., et al., "Cloning, Sequence Analysis, Expression and Inactivation of the *Corynebacterium glutamicum* pta-ack Operon Encoding Phosphotransacetylase and Acetate Kinase", Microbiology, vol. 145, (1999), pp. 503-513.
Patek, M., et al., "Promoters from *Corynebacterium glutamicum*: Cloning, Molecular Analysis and Search for a Consensus Motif", Microbiology, vol. 142, (1996), pp. 1297-1309.
De Leon, P., et al., "*Streptomyces lividans* groES, groEL1 and groEL2 Genes", Microbiology, vol. 143, (1997), pp. 3563-3571.
Tauschek, M., et al., "Transcriptional Analysis of the groESL Operon of *Neisseria gonorrhoeae*", Gene, vol. 189, (1997), pp. 107-112.
Thies, F. L., "Cloning, Sequencing and Molecular Analysis of the *Campylobacter jejuni* groESL Bicistronic Operon", Microbiology, vol. 145, (1999), pp. 89-98.
Patek, M , et al , "Function of *Corynebacterium glutamicum* Promoters in *Escherichia coli, Streptomyces lividans,* and *Bacillus subtilis*", Journal of Biotechnology, vol. 104, (2003), pp. 325-334.
Patek, M., et al., "Promoters of *Corynebacterium glutamicum*", Journal of Biotechnology, vol. 104, (2003), pp. 311-323.
Bernard, P., et al., "The F Plasmid CdcB Protein Induces Efficient ATP-dependent DNA Cleavage by Gyrase", Journal of Molecular Biology, vol. 234, (1993), pp. 534-541.
Blomfield, I.C., et al., "Allelic Exchange in *Escherichia coli* using the *Bacillus subtilis* sacB Gene and a Temperature-Sensitive pSC101 Replicon", Molecular Microbiology, vol. 5, No. 6, (1991), pp. 1447-1457.
Bradford, M. M., "A Rapid and Sensitive Method for the Quantitation of Microgram Quantities of Protein Utilizing the Principle of Protein-Dye Binding", Analytical Biochemistry, vol. 72, (1976), pp. 248-254.

(Continued)

*Primary Examiner* — Nancy T Vogel
(74) *Attorney, Agent, or Firm* — Novak Druce Connolly Bove + Quigg LLP

(57) ABSTRACT

The present invention relates to the use of nucleic acid sequences for regulating the transcription and expression of genes, the novel promoters and expression units themselves, methods for altering or causing the transcription rate and/or expression rate of genes, expression cassettes comprising the expression units, genetically modified microorganisms with altered or caused transcription rate and/or expression rate, and methods for preparing biosynthetic products by cultivating the genetically modified microorganisms.

17 Claims, 2 Drawing Sheets

(56) References Cited

OTHER PUBLICATIONS

Cane, D. E., et al. "Harnessing the Biosynthetic Code: Combinations, Permutations, and Mutations", Science, vol. 282, (1998), pp. 63-68.
Christopherson, R. I., et al., "Potent Inhibitors of De Novo Pyrimidine and Purine Biosynthesis as Chemotherapeutic Agents", vol. 10, No. 4, (1990), pp. 505-548.
Dunican, L. K., et al., "High Frequency Transformation of Whole Cells of Amino Acid Producing Coryneform Bacteria Using High Voltage Electroporation", Bio/Technology, vol. 7, (1989), pp. 1067-1070.
Eikmanns, B. J., et al., "A Family of *Corynebacterium glutamicum/Escherichia coli* Shuttle Vectors for Cloning, Controlled Gene Expression, and Promoter Probing", Gene, vol. 102, (1991), pp. 93-98.
Eikmanns, B. J., et al., "Nucleotide Sequence, Expression and Transcriptional Analysis of the *Corynebacterium glutamicum* gltA Gene Encoding Citrate Synthase", Microbiology, vol. 140, (1994), pp. 1817-1828.
GenBank Accession No. ATCC13032.
Greasham, R. L., et al., "Design and Optimization of Growth Media", Applied Microbial Physiology. Eds. P.M. Rhodes, et al., IRL Press at Oxford University Press, (1997), pp. 53-73.
Guerrero, C., et al., "Directed Mutagenesis of a Regulatory Palindromic Sequence Upstream from the *Brevibacterium lactofermentum* Tryptophan Operon", Gene, vol. 138, (1994), pp. 35-41.
Higgins, D. G., et al., "Fast and Sensitive Multiple Sequence Alignments on a Microcomputer", Cabios Communications, vol. 5, No. 2, (1989), pp. 151-153.
International Preliminary Report on Patentability for Application No. PCT/EP2004/014263, dated Nov. 18, 2005.
International Search Report for Application No. PCT/EP2004/014263, dated Dec. 18, 2003.
Jaeger, W., et al., "Expression of the *Bacillus subtilis* sacB Gene Leads to Sucrose Sensitivity in the Gram-Positive Bacterium *Corynebacterium glutamicum* but Not in *Streptomyces lividans*", Journal of Bacteriology, vol. 174, No. 16, (1992), pp. 5462-5465.
Jensen, P. R., et al., "Artificial Promoters for Metabolic Optimization", Biotechnology and Bioengineering, vol. 58, Nos. 2&3, (1998), pp. 191-195.
Kenell, D., Prog. Nucl. Acid Res. Mol. Biol, vol. 11, (1971), pp. 259-301.
Kuninaka, A., "Nucleotides and Related Compounds", Biotechnology, Ed. Rehm et al., VCH, vol. 6, (1996), pp. 561-612.
Labarre, J., et al., "Gene Replacement, Integration, and Amplification at the gdhA Locus of *Corynebacterium glutamicum*", Journal of Bacteriology, vol. 175, No. 4, (1993), pp. 1001-1007.
Lennox, E. S., "Transduction of Linked Genetic Characters of the Host by Bacteriophage P1", Virology, vol. 1, (1955), pp. 190-206.
Leuchtenberger, W., "Amino Acids—Technical Production and Use", Biotechnology, Ed. Rehm et al., VCH, vol. 6, No. 14a, (1996), pp. 465-502.
Liebl, W., et al., "High Efficiency Electroporation of Intact *Corynebacterium glutamicum* Cells", FEMS Microbiology Letters, vol. 65, (1989), pp. 299-304.
Makrides, S. C., "Strategies for Achieving High-Level Expression of Genes in *Escherichia coli*", Microbiological Reviews, vol. 60, No. 3, (1996), pp. 512-538.
Malakhova, I.I., et al., "Thin-Layer Chromatography of Free Amino Acids. Selection of Conditions for the Separation of L-Lysine, L-Homoserine, and L-Threonine", Russian Biotechnology, vol. 11, (1996), pp. 26-31.
Malumbres, M., et al., "Codon Preference in Corynebacteria", Gene, vol. 134, (1993), pp. 15-24.
Martin, J.F., et al., "Cloning Systems in Amino Acid-Producing Corynebacteria", Bio/Technology, vol. 5, (1987), pp. 137-146.
Menkel, E., et al., "Influence of Increased Aspartate Availability on Lysine Formation by a Recombinant Strain of *Corynebacterium glutamicum* and Utilization of Fumarate", Applied and Environmental Microbiology, vol. 44, No. 3, (1989), pp. 684-688.
Michal, G., "Nucleotide and Nucleoside", Biochemical Pathways: An Atlas of Biochemistry and Molecular Biology, Ed. Viley, (1999), pp. 99-107.
Neidhardt, F.C., et al., "Chemical Composition of *Escherichia coli", Escherichia coli* and *Salmonella*, ASM Press, 2nd Edition, vol. 1, (1996), pp. 13-16.
Paiva, C.L.A., et al., "Biotechnological Applications of the Disaccharide Trehalose", Biotechnology Annual Review, vol. 2, (1996), pp. 293-314.
Pátek, M., et al., "Leucine Synthesis in *Cornebacterium glutamicum*: Enzyme Activities, Structure of leuA, and Effect of leuA Inactiviation on Lysine Synthesis", Applied and Environmental Microbiology, vol. 60, No. 1., (1994), pp. 133-140.
Reinscheid, D. J., et al., "Stable Expression of hom-1-thrB in *Corynebacterium glutamicum* and its Effect on the Carbon Flux to Threonine and Related Amino Acids", Applied and Environmental Microbiology, vol. 60, No. 1, (1994), pp. 126-132.
Sambrook, J., et al., "Analysis of Genomic DNA by Southern Hybridization", Molecular Cloning, a Laboratory Manual, 2nd Edition, Cold Spring Harbor Laboratory Press, (1989), pp. 9.31-9.62.
Sanger, F., et al., "DNA Sequencing with Chain-Terminating Inhibitors", Proc. Natl. Acad. Sci. USA, vol. 74, No. 12, (1977), pp. 5463-5467.
Schaefer, A., et al., "Small Mobilizable Multi-Purpose Cloning Vectors Derived from the *Escherichia coli* Plasmids pK18 and pK19: Selection of Defined Deletions in the Chromosome of *Corynebacterium glutamicum*", Gene, vol. 145, (1994), pp. 69-73.
Schmidt, S., et al., "Near Infrared Spectroscopy in Fermentation and Quality Control for Amino Acid Production", Bioprocess Engineering, vol. 19, (1998), pp. 67-70.
Schrumpf, B., et al., "A Functionally Split Pathway for Lysine Synthesis in *Corynebacterium glutamicum*", Journal of Bacteriology, vol. 178, No. 14, (1991), pp. 4510-4516.
Schwarzer, A., et al., "Manipulation of *Corynebacterium glutamicum* by Gene Disruption and Replacement", Bio/Technology, vol. 9, (1991), pp. 84-87.
Serwold-Davis, T. M., et al., "Localization of an Origin of Replication in *Corynebacterium diphtheriae* Broad Host Range Plasmid pNG2 that also Functions in *Escherichia coli*", FEMS Microbiology Letters, vol. 66, (1990), pp. 119-124.
Shiosaka, M., "Application of Trehalose", FFI Journal, vol. 172, (1997), pp. 97-102.
Simmonds, H.A., "The Enzymes of Nucleotide Biosynthesis", Biochemical Society Transactions, vol. 23, (1995), pp. 877-902.
Simon, R., et al., "A Broad Host Range Mobilization System for In Vivo Genetic Engineering: Transposon Mutagenesis in Gram Negative Bacteria", Bio/Technology, vol. 1, (1983), pp. 784-791.
Singer, M. A., et al., "Thermotolerance in *Saccharomyces cerevisiae*: the Yin and Yang of Trehalose", Trends Biotech, vol. 16, (1998), pp. 460-467.
Smith, J.L., "Enzymes of Nucleotide Synthesis", Current Opinion in Structural Biology, vol. 5, (1995), pp. 752-757.
Sonnen, H., et al., "Characterization of pGA1, a New Plasmid from *Corynebacterium glutamicum* LP-6", Gene, vol. 107, (1991), pp. 69-74.
Spratt, B. G., et al., "Kanamycin-Resistant Vectors that are Analogues of Plasmids pUC8, pUC9, pEMBL8 and pEMBL9", Gene, vol. 41, (1986), pp. 337-342.
Strauss, W. M., "Hybridization with Radioactive Probes", Current Protocols in Molecular Biology, John Wiley & Sons, N.Y., (1993), pp. 6.3.1-6.3.6.
Stryer, L., "Amino Acid Degradation and the Urea Cycle", Biochemistry, Third Edition, W.H. Freeman and Company, Chapter 21, (1988), pp. 495-516.
Stryer, L., "Biosynthesis of Amino Acids and Heme", Biochemistry, Third Edition, W.H. Freeman and Company, Chapter. 24, (1988), pp. 575-600.
Tauch, A., et al., "*Corynebacterium glutamicum* DNA is Subjected to Methylation-Restriction in *Escherichia coli*", FEMS Microbiology Letters, vol. 123, (1994), pp. 343-348.
Tauch, A., et al., "The Erythromycin Resistance Gene of the *Corynebacterium xerosis* R-plasmid pTP10 also Carrying Chloramphenicol, Kanamycin, and Tetracycline Resistances is

(56) References Cited

OTHER PUBLICATIONS

Capable of Transposition in *Corynebacterium glutamicum*", Plasmid, vol. 33, (1995), pp. 168-179.
Thierbach, G., et al., "Transformation of Spheroplasts and Protoplasts of *Corynebacterium glutamicum*", Appl. Microbiol. Biotechnol., vol. 29, (1988), pp. 356-362.
Tsuchiya, M., et al., "Genetic Control Systems of *Escherichia coli* Can Confer Inducible Expression of Cloned Genes in Coryneform Bacteria", Bio/Technology, vol. 6, (1988), pp. 428-430.
Ullmann's Encyclopedia of Industrial Chemistry, "Amino Acids", Eds. Barbara Elvers et al., VCH, vol. A2, (1985), pp. 57-97.
Ullmann's Encyclopedia of Industrial chemistry, "Tires", Eds. Barbara Elvers et al., VCH, vol. A27, (1996), pp. 89-90.
Ullmann's Encyclopedia of Industrial Chemistry, "Vitamins", Eds. Barbara Elvers et al., VCH, vol. A27, (1996), pp. 443-613.
Ullmann's Encyclopedia of Industrial Chemistry, "Vitamins", Eds. Barbara Elvers et al., VCH, vol. A27, (1996), pp. 521-547.
Ullmann's Encyclopedia of Industrial Chemistry, "Vitamins", Eds. Barbara Elvers et al., VCH, vol. A27, (1996), pp. 575-587.
Ullmann's Encyclopedia of Industrial Chemistry, "Vitamins", Eds. Barbara Elvers et al., VCH, vol. A27, (1996), pp. 559-566.
Umbarger, H.E., "Amino Acid Biosynthesis and its Regulation", Ann. Rev. Biochem., vol. 47, (1978), pp. 533-606.
Voet, D., et al., "Nucleic Acid Structures and Manipulation", Biochemistry, Wiley Press, Chapter 28, (1995), pp. 896-897.
Zalkin, H., et al., "De Novo Purine Nucleotide Biosynthesis", Progress in Nucleic Acid Research and Molecular Biology, vol. 42, (1992), pp. 259-287.

SEQUENCE LISTING

```
<160> NUMBER OF SEQ ID NOS: 53

<210> SEQ ID NO 1
<211> LENGTH: 164
<212> TYPE: DNA
<213> ORGANISM: Corynebacterium glutamicum

<400> SEQUENCE: 1

cggcttaaag tttggctgcc atgtgaattt ttagcaccct caacagttga gtgctggcac      60

tctcgggggt agagtgccaa ataggttgtt tgacacacag ttgttcaccc gcgacgacgg     120
```

-continued

```
ctgtgctgga aacccacaac cggcacacac aaaatttttc tcat                  164


<210> SEQ ID NO 2
<211> LENGTH: 177
<212> TYPE: DNA
<213> ORGANISM: Corynebacterium glutamicum

<400> SEQUENCE: 2

cggcttaaag tttggctgcc atgtgaattt ttagcaccct caacagttga gtgctggcac     60

tctcgggggt agagtgccaa ataggttgtt tgacacacag ttgttcaccc gcgacgacgg    120

ctgtgctgga aacccacaac cggcacacac aaaatttttc tcatggaggg attcatc       177


<210> SEQ ID NO 3
<211> LENGTH: 1365
<212> TYPE: DNA
<213> ORGANISM: Corynebacterium glutamicum

<400> SEQUENCE: 3

atgaatgatg agaatattca aagctccaac tatcagccat tcccgagttt tgacgattgg     60

aaacagatcg aggtgtcgct cttagatgtc atcgaatcct cacgccattt ttctgatttg    120

aaagatagca ctgatcgttc tgcgttagat gctgcgctag agagagcaaa aagagctgcc    180

gcagttgata ccaatgccat agaaggaatc ttccaaactg atcgcggttt tacccataca    240

gttgcaacgc aggtaggggc ttgggagcaa caaatggcga tgaaaggcaa acatgttaag    300

cctgcgtttg acgatactct agaaggcttt gagtatgttc tcgatgcagt aactggtaga    360

actccaatct ctcagcaatg gattagaaat ttgcacgccg tcattctgcg gagccaagaa    420

agccacgagg tttttacagc cgttggagtc caaaatcagg cgcttcagaa aggcgagtat    480

aaaactcagc caaatagtcc acagcgctca gatggatctg tacatgcata cgccccagtt    540

gaagatactc ctgctgaaat ggctagattt atttcagaac ttgaatctaa ggaattctta    600

gcagccgaga aggttattca agctgcctat gcccactatg ctttcgtatg tattcatcct    660

tttgcagatg ggaatggacg agttgcacga gccttggcta gtgtttttct atacaaagat    720

cctggtgtcc ctctcgtaat ctaccaagat caacgcagag attacatcca tgctctagaa    780

gcagcggaca agaataaccc gctcctgctg attagattct ttgctgaacg agtgaccgat    840

actattaact ctattatcgt tgatctcact accccgatcg cgggtaaatc tggttcggct    900

aagctttcgg atgcgctacg ccccactcgc gtattaccag aattacatga tgctgcacat    960

aggctccaag aaagtttatt tacagaaatc cgatctcgat tggatgaaga aggaaaaagg   1020

aatgggttgg agtttctact tcaacggatt tttatcggtt ccccattcaa tctgccagag   1080

ggctataacg ctttccctga tagctattgt ctgaccttag ctttcaatag caactctcca   1140

aaacaaatct tccacccgct atccatagta atagcagctc gagatgggaa aagagcgagc   1200

agcgacctcg tggcagctac ttctattgga tacaactttc acgcttacgg acgtgaagtc   1260

gagcctgttg ttactgaaag ctttcgagaa cgtgtgaaaa tttacgccga cgggattgta   1320

gatcacttct taaccgaact ggctaaaaag tttcaacaga attaa                   1365


<210> SEQ ID NO 4
<211> LENGTH: 454
<212> TYPE: PRT
<213> ORGANISM: Corynebacterium glutamicum

<400> SEQUENCE: 4

Met Asn Asp Glu Asn Ile Gln Ser Ser Asn Tyr Gln Pro Phe Pro Ser
  1               5                  10                  15
```

-continued

```
Phe Asp Asp Trp Lys Gln Ile Glu Val Ser Leu Leu Asp Val Ile Glu
            20                  25                  30

Ser Ser Arg His Phe Ser Asp Leu Lys Asp Ser Thr Asp Arg Ser Ala
        35                  40                  45

Leu Asp Ala Ala Leu Glu Arg Ala Lys Arg Ala Ala Ala Val Asp Thr
    50                  55                  60

Asn Ala Ile Glu Gly Ile Phe Gln Thr Asp Arg Gly Phe Thr His Thr
65                  70                  75                  80

Val Ala Thr Gln Val Gly Ala Trp Glu Gln Gln Met Ala Met Lys Gly
                85                  90                  95

Lys His Val Lys Pro Ala Phe Asp Asp Thr Leu Glu Gly Phe Glu Tyr
            100                 105                 110

Val Leu Asp Ala Val Thr Gly Arg Thr Pro Ile Ser Gln Gln Trp Ile
        115                 120                 125

Arg Asn Leu His Ala Val Ile Leu Arg Ser Gln Glu Ser His Glu Val
    130                 135                 140

Phe Thr Ala Val Gly Val Gln Asn Gln Ala Leu Gln Lys Gly Glu Tyr
145                 150                 155                 160

Lys Thr Gln Pro Asn Ser Pro Gln Arg Ser Asp Gly Ser Val His Ala
                165                 170                 175

Tyr Ala Pro Val Glu Asp Thr Pro Ala Glu Met Ala Arg Phe Ile Ser
            180                 185                 190

Glu Leu Glu Ser Lys Glu Phe Leu Ala Ala Glu Lys Val Ile Gln Ala
        195                 200                 205

Ala Tyr Ala His Tyr Ala Phe Val Cys Ile His Pro Phe Ala Asp Gly
    210                 215                 220

Asn Gly Arg Val Ala Arg Ala Leu Ala Ser Val Phe Leu Tyr Lys Asp
225                 230                 235                 240

Pro Gly Val Pro Leu Val Ile Tyr Gln Asp Gln Arg Arg Asp Tyr Ile
                245                 250                 255

His Ala Leu Glu Ala Ala Asp Lys Asn Asn Pro Leu Leu Leu Ile Arg
            260                 265                 270

Phe Phe Ala Glu Arg Val Thr Asp Thr Ile Asn Ser Ile Ile Val Asp
        275                 280                 285

Leu Thr Thr Pro Ile Ala Gly Lys Ser Gly Ser Ala Lys Leu Ser Asp
    290                 295                 300

Ala Leu Arg Pro Thr Arg Val Leu Pro Glu Leu His Asp Ala Ala His
305                 310                 315                 320

Arg Leu Gln Glu Ser Leu Phe Thr Glu Ile Arg Ser Arg Leu Asp Glu
                325                 330                 335

Glu Gly Lys Arg Asn Gly Leu Glu Phe Leu Leu Gln Arg Ile Phe Ile
            340                 345                 350

Gly Ser Pro Phe Asn Leu Pro Glu Gly Tyr Asn Ala Phe Pro Asp Ser
        355                 360                 365

Tyr Cys Leu Thr Leu Ala Phe Asn Ser Asn Ser Pro Lys Gln Ile Phe
    370                 375                 380

His Pro Leu Ser Ile Val Ile Ala Ala Arg Asp Gly Lys Arg Ala Ser
385                 390                 395                 400

Ser Asp Leu Val Ala Ala Thr Ser Ile Gly Tyr Asn Phe His Ala Tyr
                405                 410                 415

Gly Arg Glu Val Glu Pro Val Val Thr Glu Ser Phe Arg Glu Arg Val
            420                 425                 430

Lys Ile Tyr Ala Asp Gly Ile Val Asp His Phe Leu Thr Glu Leu Ala
```

```
            435                 440                 445
Lys Lys Phe Gln Gln Asn
    450

<210> SEQ ID NO 5
<211> LENGTH: 19
<212> TYPE: DNA
<213> ORGANISM: Corynebacterium glutamicum

<400> SEQUENCE: 5

gccgcagcaa acccagtag                                                19

<210> SEQ ID NO 6
<211> LENGTH: 31
<212> TYPE: DNA
<213> ORGANISM: Corynebacterium glutamicum

<400> SEQUENCE: 6

agtcgacacg atgaatccct ccatgagaaa a                                  31

<210> SEQ ID NO 7
<211> LENGTH: 54
<212> TYPE: DNA
<213> ORGANISM: Corynebacterium glutamicum

<400> SEQUENCE: 7

tttttctcat ggagggattc atcgtgtcga ctcacacatc ttcaacgctt ccag          54

<210> SEQ ID NO 8
<211> LENGTH: 23
<212> TYPE: DNA
<213> ORGANISM: Corynebacterium glutamicum

<400> SEQUENCE: 8

cccgcagcaa cgcacgcaag aaa                                           23

<210> SEQ ID NO 9
<211> LENGTH: 22
<212> TYPE: DNA
<213> ORGANISM: Corynebacterium glutamicum

<400> SEQUENCE: 9

gcattcgcgc cgctcgtaac ta                                            22

<210> SEQ ID NO 10
<211> LENGTH: 19
<212> TYPE: DNA
<213> ORGANISM: Corynebacterium glutamicum

<400> SEQUENCE: 10

ggttcccgcg ccctggtaa                                                19

<210> SEQ ID NO 11
<211> LENGTH: 5720
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11

ggtcgactct agaggatccc cgggtaccga gctcgaattc actggccgtc gttttacaac   60

gtcgtgactg ggaaaaccct ggcgttaccc aacttaatcg ccttgcagca catccccctt  120
```

-continued

```
tcgccagctg gcgtaatagc gaagaggccc gcaccgatcg cccttcccaa cagttgcgca    180
gcctgaatgg cgaatggcga taagctagct tcacgctgcc gcaagcactc agggcgcaag    240
ggctgctaaa ggaagcggaa cacgtagaaa gccagtccgc agaaacggtg ctgaccccgg    300
atgaatgtca gctactgggc tatctggaca agggaaaacg caagcgcaaa gagaaagcag    360
gtagcttgca gtgggcttac atggcgatag ctagactggg cggttttatg gacagcaagc    420
gaaccggaat tgccagctgg ggcgccctct ggtaaggttg ggaagccctg caaagtaaac    480
tggatggctt tcttgccgcc aaggatctga tggcgcaggg gatcaagatc tgatcaagag    540
acaggatgag gatcgtttcg catgattgaa caagatggat tgcacgcagg ttctccggcc    600
gcttgggtgg agaggctatt cggctatgac tgggcacaac agacaatcgg ctgctctgat    660
gccgccgtgt tccggctgtc agcgcagggg cgcccggttc tttttgtcaa gaccgacctg    720
tccggtgccc tgaatgaact ccaagacgag gcagcgcggc tatcgtggct ggccacgacg    780
ggcgttcctt gcgcagctgt gctcgacgtt gtcactgaag cgggaaggga ctggctgcta    840
ttgggcgaag tgccggggca ggatctcctg tcatctcacc ttgctcctgc cgagaaagta    900
tccatcatgg ctgatgcaat gcggcggctg catacgcttg atccggctac ctgcccattc    960
gaccaccaag cgaaacatcg catcgagcga gcacgtactc ggatggaagc cggtcttgtc   1020
gatcaggatg atctggacga agagcatcag gggctcgcgc cagccgaact gttcgccagg   1080
ctcaaggcgc ggatgcccga cggcgaggat ctcgtcgtga cccatggcga tgcctgcttg   1140
ccgaatatca tggtggaaaa tggccgcttt tctggattca tcgactgtgg ccggctgggt   1200
gtggcggacc gctatcagga catagcgttg gctacccgtg atattgctga agagcttggc   1260
ggcgaatggg ctgaccgctt cctcgtgctt tacggtatcg ccgctcccga ttcgcagcgc   1320
atcgccttct atcgccttct tgacgagttc ttctgagcgg gactctgggg ttcgctagag   1380
gatcgatcct ttttaaccca tcacatatac ctgccgttca ctattattta gtgaaatgag   1440
atattatgat attttctgaa ttgtgattaa aaaggcaact ttatgcccat gcaacagaaa   1500
ctataaaaaa tacagagaat gaaaagaaac agatagattt tttagttctt taggcccgta   1560
gtctgcaaat ccttttatga ttttctatca aacaaaagag gaaaatagac cagttgcaat   1620
ccaaacgaga gtctaataga atgaggtcga aaagtaaatc gcgcgggttt gttactgata   1680
aagcaggcaa gacctaaaat gtgtaaaggg caaagtgtat actttggcgt caccccttac   1740
atattttagg tctttttta ttgtgcgtaa ctaacttgcc atcttcaaac aggagggctg   1800
gaagaagcag accgctaaca cagtacataa aaaaggagac atgaacgatg aacatcaaaa   1860
agtttgcaaa acaagcaaca gtattaacct ttactaccgc actgctggca ggaggcgcaa   1920
ctcaagcgtt tgcgaaagaa acgaaccaaa agccatataa ggaaacatac ggcatttccc   1980
atattacacg ccatgatatg ctgcaaatcc ctgaacagca aaaaaatgaa aaatatcaag   2040
tttctgaatt tgattcgtcc acaattaaaa atatctcttc tgcaaaaggc ctggacgttt   2100
gggacagctg gccattacaa aacgctgacg gcactgtcgc aaactatcac ggctaccaca   2160
tcgtctttgc attagccgga gatcctaaaa atgcggatga cacatcgatt tacatgttct   2220
atcaaaaagt cggcgaaact tctattgaca gctggaaaaa cgctggccgc gtctttaaag   2280
acagcgacaa attcgatgca aatgattcta tcctaaaaga ccaaacacaa gaatggtcag   2340
gttcagccac atttacatct gacggaaaaa tccgtttatt ctacactgat ttctccggta   2400
aacattacgg caaacaaaca ctgacaactg cacaagttaa cgtatcagca tcagacagct   2460
ctttgaacat caacggtgta gaggattata aatcaatctt tgacggtgac ggaaaaacgt   2520
```

-continued

```
atcaaaatgt acagcagttc atcgatgaag gcaactacag ctcaggcgac aaccatacgc   2580
tgagagatcc tcactacgta gaagataaag gccacaaata cttagtattt gaagcaaaca   2640
ctggaactga agatggctac caaggcgaag aatctttatt taacaaagca tactatggca   2700
aaagcacatc attcttccgt caagaaagtc aaaaacttct gcaaagcgat aaaaaacgca   2760
cggctgagtt agcaaacggc gctctcggta tgattgagct aaacgatgat tacacactga   2820
aaaaagtgat gaaaccgctg attgcatcta acacagtaac agatgaaatt gaacgcgcga   2880
acgtctttaa aatgaacggc aaatggtacc tgttcactga ctcccgcgga tcaaaaatga   2940
cgattgacgg cattacgtct aacgatattt acatgcttgg ttatgtttct aattctttaa   3000
ctggcccata caagccgctg aacaaaactg gccttgtgtt aaaaatggat cttgatccta   3060
acgatgtaac ctttacttac tcacacttcg ctgtacctca agcgaaagga aacaatgtcg   3120
tgattacaag ctatatgaca aacagaggat tctacgcaga caaacaatca acgtttgcgc   3180
cgagcttcct gctgaacatc aaaggcaaga aaacatctgt tgtcaaagac agcatccttg   3240
aacaaggaca attaacagtt aacaaataaa aacgcaaaag aaaatgccga tgggtaccga   3300
gcgaaatgac cgaccaagcg acgcccaacc tgccatcacg agatttcgat tccaccgccg   3360
ccttctatga aaggttgggc ttcggaatcg ttttccggga cgccctcgcg gacgtgctca   3420
tagtccacga cgcccgtgat tttgtagccc tggccgacgg ccagcaggta ggccgacagg   3480
ctcatgccgg ccgccgccgc cttttcctca atcgctcttc gttcgtctgg aaggcagtac   3540
accttgatag gtgggctgcc cttcctggtt ggcttggttt catcagccat ccgcttgccc   3600
tcatctgtta cgccggcggt agccggccag cctcgcagag caggattccc gttgagcacc   3660
gccaggtgcg aataagggac agtgaagaag gaacacccgc tcgcgggtgg gcctacttca   3720
cctatcctgc ccggctgacg ccgttggata caccaaggaa agtctacacg aaccctttgg   3780
caaaatcctg tatatcgtgc gaaaaaggat ggatataccg aaaaaatcgc tataatgacc   3840
ccgaagcagg gttatgcagc ggaaaagcgc tgcttccctg ctgttttgtg gaatatctac   3900
cgactggaaa caggcaaatg caggaaatta ctgaactgag gggacaggcg agagacgatg   3960
ccaaagagct cctgaaaatc tcgataactc aaaaaatacg cccggtagtg atcttatttc   4020
attatggtga aagttggaac ctcttacgtg ccgatcaacg tctcattttc gccaaaagtt   4080
ggcccagggc ttcccggtat caacagggac accaggattt atttattctg cgaagtgatc   4140
ttccgtcaca ggtatttatt cggcgcaaag tgcgtcgggt gatgctgcca acttactgat   4200
ttagtgtatg atggtgtttt tgaggtgctc cagtggcttc tgtttctatc agctcctgaa   4260
aatctcgata actcaaaaaa tacgcccggt agtgatctta tttcattatg gtgaaagttg   4320
gaacctctta cgtgccgatc aacgtctcat tttcgccaaa agttggccca gggcttcccg   4380
gtatcaacag ggacaccagg atttatttat tctgcgaagt gatcttccgt cacaggtatt   4440
tattcggcgc aaagtgcgtc gggtgatgct gccaacttac tgatttagtg tatgatggtg   4500
tttttgaggt gctccagtgg cttctgtttc tatcagggct ggatgatcct ccagcgcggg   4560
gatctcatgc tggagttctt cgcccacccc aaaaggatct aggtgaagat cctttttgat   4620
aatctcatga ccaaaatccc ttaacgtgag ttttcgttcc actgagcgtc agaccccgta   4680
gaaaagatca aaggatcttc ttgagatcct ttttttctgc gcgtaatctg ctgcttgcaa   4740
acaaaaaaac caccgctacc agcggtggtt tgtttgccgg atcaagagct accaactctt   4800
tttccgaagg taactggctt cagcagagcg cagataccaa atactgttct tctagtgtag   4860
ccgtagttag gccaccactt caagaactct gtagcaccgc ctacatacct cgctctgcta   4920
```

-continued atcctgttac cagtggctgc tgccagtggc gataagtcgt gtcttaccgg gttggactca 4980
agacgatagt taccggataa ggcgcagcgg tcgggctgaa cggggggttc gtgcacacag 5040
cccagcttgg agcgaacgac ctacaccgaa ctgagatacc tacagcgtga gctatgagaa 5100
agcgccacgc ttcccgaagg gagaaaggcg gacaggtatc cggtaagcgg cagggtcgga 5160
acaggagagc gcacgaggga gcttccaggg ggaaacgcct ggtatcttta tagtcctgtc 5220
gggtttcgcc acctctgact tgagcgtcga tttttgtgat gctcgtcagg ggggcggagc 5280
ctatggaaaa acgccagcaa cgcggccttt ttacggttcc tggccttttg ctggcctttt 5340
gctcacatgt tctttcctgc gttatcccct gattctgtgg ataaccgtat taccgccttt 5400
gagtgagctg ataccgctcg ccgcagccga acgaccgagc gcagcgagtc agtgagcgag 5460
gaagcggaag agcgcccaat acgcaaaccg cctctccccg cgcgttggcc gattcattaa 5520
tgcagctggc acgacaggtt tcccgactgg aaagcgggca gtgagcgcaa cgcaattaat 5580
gtgagttagc tcactcatta ggcaccccag gctttacact ttatgcttcc ggctcgtatg 5640
ttgtgtggaa ttgtgagcgg ataacaattt cacacaggaa acagctatga ccatgattac 5700
gccaagcttg catgcctgca 5720

<210> SEQ ID NO 12
<211> LENGTH: 24
<212> TYPE: DNA
<213> ORGANISM: Corynebacterium glutamicum

<400> SEQUENCE: 12
ccggcgaagt gtctgctcgc gtga 24

<210> SEQ ID NO 13
<211> LENGTH: 18
<212> TYPE: DNA
<213> ORGANISM: Corynebacterium glutamicum

<400> SEQUENCE: 13
accccgcccc agtttttc 18

<210> SEQ ID NO 14
<211> LENGTH: 7438
<212> TYPE: DNA
<213> ORGANISM: Artificial Sequence
<220> FEATURE:
<223> OTHER INFORMATION: Description of Artificial Sequence: Synthetic
construct

<400> SEQUENCE: 14
ttatttgtta actgttaatt gtccttgttc aaggatgctg tctttgacaa cagatgtttt 60
cttgcctttg atgttcagca ggaagctcgg cgcaaacgtt gattgtttgt ctgcgtagaa 120
tcctctgttt gtcatatagc ttgtaatcac gacattgttt cctttcgctt gaggtacagc 180
gaagtgtgag taagtaaagg ttacatcgtt aggatcaaga tccattttta acacaaggcc 240
agttttgttc agcggcttgt atgggccagt taaagaatta gaaacataac caagcatgta 300
aatatcgtta gacgtaatgc cgtcaatcgt catttttgat ccgcgggagt cagtgaacag 360
gtaccatttg ccgttcattt taaagacgtt cgcgcgttca atttcatctg ttactgtgtt 420
agatgcaatc agcggtttca tcactttttt cagtgtgtaa tcatcgttta gctcaatcat 480
accgagagcg ccgtttgcta actcagccgt gcgtttttta tcgctttgca gaagtttttg 540
actttcttga cggaagaatg atgtgctttt gccatagtat gctttgttaa ataaagattc 600
ttcgccttgg tagccatctt cagttccagt gtttgcttca aatactaagt atttgtggcc 660

```
tttatcttct acgtagtgag gatctctcag cgtatggttg tcgcctgagc tgtagttgcc    720
ttcatcgatg aactgctgta cattttgata cgtttttccg tcaccgtcaa agattgattt    780
ataatcctct acaccgttga tgttcaaaga gctgtctgat gctgatacgt taacttgtgc    840
agttgtcagt gtttgtttgc cgtaatgttt accggagaaa tcagtgtaga ataaacggat    900
ttttccgtca gatgtaaatg tggctgaacc tgaccattct tgtgtttggt cttttaggat    960
agaatcattt gcatcgaatt tgtcgctgtc tttaaagacg cggccagcgt tttccagct    1020
gtcaatagaa gtttcgccga ctttttgata gaacatgtaa atcgatgtgt catccgcatt   1080
tttaggatct ccggctaatg caaagacgat gtggtagccg tgatagtttg cgacagtgcc   1140
gtcagcgttt tgtaatggcc agctgtccca aacgtccagg ccttttgcag aagagatatt   1200
tttaattgtg gacgaatcaa attcaggaac ttgatatttt tcattttttt gctgttcagg   1260
gatttgcagc atatcatggc gtgtaatatg ggaaatgccg tatgtttcct tatatggctt   1320
ttggttcgtt tctttcgcaa acgcttgagt tgcgcctcct gccagcagtg cggtagtaaa   1380
ggttaatact gttgcttgtt ttgcaaactt tttgatgttc atcgttcatg tctccttttt   1440
tatgtactgt gttagcggtc tgcttcttcc agccctcctg tttgaagatg gcaagttagt   1500
tacgcacaat aaaaaaagac ctaaaatatg taaggggtga cgccaaagta tacactttgc   1560
cctttacaca ttttaggtct tgcctgcttt atcagtaaca aacccgcgcg atttactttt   1620
cgacctcatt ctattagact ctcgtttgga ttgcaactgg tctattttcc tcttttgttt   1680
gatagaaaat cataaaagga tttgcagact acgggcctaa agaactaaaa aatctatctg   1740
tttcttttca ttctctgtat tttttatagt ttctgttgca tgggcataaa gttgcctttt   1800
taatcacaat tcagaaaata tcataatatc tcatttcact aaataatagt gaacggcagg   1860
tatatgtgat gggttaaaaa ggatcgatcc tctagcgaac cccagagtcc cgctcagaag   1920
aactcgtcaa gaaggcgata gaaggcgatg cgctgcgaat cgggagcggc gataccgtaa   1980
agcacgagga agcggtcagc ccattcgccg ccaagctctt cagcaatatc acgggtagcc   2040
aacgctatgt cctgatagcg gtccgccaca cccagccggc cacagtcgat gaatccagaa   2100
aagcggccat tttccaccat gatattcggc aagcaggcat cgccatgggt cacgacgaga   2160
tcctcgccgt cgggcatccg cgccttgagc ctggcgaaca gttcggctgg cgcgagcccc   2220
tgatgctctt cgtccagatc atcctgatcg acaagaccgg cttccatccg agtacgtgct   2280
cgctcgatgc gatgtttcgc ttggtggtcg aatgggcagg tagccggatc aagcgtatgc   2340
agccgccgca ttgcatcagc catgatggat actttctcgg caggagcaag gtgagatgac   2400
aggagatcct gccccggcac ttcgcccaat agcagccagt cccttcccgc ttcagtgaca   2460
acgtcgagca cagctgcgca aggaacgccc gtcgtggcca gccacgatag ccgcgctgcc   2520
tcgtcttgga gttcattcag ggcaccggac aggtcggtct tgacaaaaag aaccgggcgc   2580
ccctgcgctg acagccggaa cacggcggca tcagagcagc cgattgtctg ttgtgcccag   2640
tcatagccga atagcctctc cacccaagcg gccggagaac ctgcgtgcaa tccatcttgt   2700
tcaatcatgc gaaacgatcc tcatcctgtc tcttgatcag atcttgatcc cctgcgccat   2760
cagatccttg gcggcaagaa agccatccag tttactttgc agggcttccc aaccttacca   2820
gagggcgccc cagctggcaa ttccggttcg cttgctgtcc ataaaaccgc ccagtctagc   2880
tatcgccatg taagcccact gcaagctacc tgctttctct ttgcgcttgc gttttccctt   2940
gtccagatag cccagtagct gacattcatc cggggtcagc accgtttctg cggactggct   3000
ttctacgtgt tccgcttcct ttagcagccc ttgcgccctg agtgcttgcg gcagcgtgaa   3060
```

-continued

```
gctagatgca tgctcgagcg gccgccagtg tgatggatat ctgcagaatt cgcccttccg   3120
gcgaagtgtc tgctcgcgtg attgtgcttc ctttggctac taacccacgc gccaagatgc   3180
gttccctgcg ccacggtttt gtgaagctgt tctgccgccg taactctggc ctgatcatcg   3240
gtggtgtcgt ggtggcaccg accgcgtctg agctgatcct accgatcgct gtggcagtga   3300
ccaaccgtct gacagttgct gatctggctg ataccttcgc ggtgtaccca tcattgtcag   3360
gttcgattac tgaagcagca cgtcagctgg ttcaacatga tgatctaggc taatttttct   3420
gagtcttaga ttttgagaaa acccaggatt gctttgtgca ctcctgggtt ttcactttgt   3480
taagcagttt tggggaaaag tgcaaagttt gcaaagttta gaaatatttt aagaggtaag   3540
atgtctgcag gtggaagcgt ttaaatgcgt taaacttggc caaatgtggc aacctttgca   3600
aggtgaaaaa ctggggcggg gtaagggcga attccagcac actggcggcc gttactagct   3660
tatcgccatt cgccattcag gctgcgcaac tgttgggaag ggcgatcggt gcgggcctct   3720
tcgctattac gccagctggc gaaaggggga tgtgctgcaa ggcgattaag ttgggtaacg   3780
ccagggtttt cccagtcacg acgttgtaaa acgacggcca gtgaattcaa cctgtggcgc   3840
aacgctgtat ataacctgcg tacggcttaa agtttggctg ccatgtgaat ttttagcacc   3900
ctcaacagtt gagtgctggc actctcgggg gtagagtgcc aaataggttg tttgacacac   3960
agttgttcac ccgcgacgac ggctgtgctg gaaacccaca accggcacac acaaaatttt   4020
tctcatggag ggattcatcg tgtcgactca cacatcttca acgcttccag cattcaaaaa   4080
gatcttggta gcaaaccgcg gcgaaatcgc ggtccgtgct ttccgtgcag cactcgaaac   4140
cggtgcagcc acggtagcta tttacccccg tgaagatcgg ggatcattcc accgctcttt   4200
tgcttctgaa gctgtccgca ttggtaccga aggctcacca gtcaaggcgt acctggacat   4260
cgatgaaatt atcggtgcag ctaaaaaagt taaagcagat gccatttacc cgggatacgg   4320
cttcctgtct gaaaatgccc agcttgcccg cgagtgtgcg gaaaacggca ttacttttat   4380
tggcccaacc ccagaggttc ttgatctcac cggtgataag tctcgcgcgg taaccgccgc   4440
gaagaaggct ggtctgccag ttttggcgga atccaccccg agcaaaaaca tcgatgagat   4500
cgttaaaagc gctgaaggcc agacttaccc catctttgtg aaggcagttg ccggtggtgg   4560
cggacgcggt atgcgttttg ttgcttcacc tgatgagctt cgcaaattag caacagaagc   4620
atctcgtgaa gctgaagcgg ctttcggcga tggcgcggta tatgtcgaac gtgctgtgat   4680
taaccctcag catattgaag tgcagatcct tggcgatcac actggagaag ttgtacacct   4740
ttatgaacgt gactgctcac tgcagcgtcg tcaccaaaaa gttgtcgaaa ttgcgccagc   4800
acagcatttg gatccagaac tgcgtgatcg catttgtgcg gatgcagtaa agttctgccg   4860
ctccattggt taccagggcg cgggaaccaa gggcgaattc ctctggataa tcatcgcggt   4920
agttacgagc ggcgcgaatg caagggcgaa ttcgagctcg gtacccgggg atcctctaga   4980
gtcgacctgc aggcatgcaa gcttggcgta atcatggtca tagctgtttc ctgtgtgaaa   5040
ttgttatccg ctcacaattc cacacaacat acgagccgga agcataaagt gtaaagcctg   5100
gggtgcctaa tgagtgagct aactcacatt aattgcgttg cgctcactgc ccgctttcca   5160
gtcgggaaac ctgtcgtgcc agctgcatta atgaatcggc caacgcgcgg ggagaggcgg   5220
tttgcgtatt gggcgctctt ccgcttcctc gctcactgac tcgctgcgct cggtcgttcg   5280
gctgcggcga gcggtatcag ctcactcaaa ggcggtaata cggttatcca cagaatcagg   5340
ggataacgca ggaaagaaca tgtgagcaaa aggccagcaa aaggccagga accgtaaaaa   5400
ggccgcgttg ctggcgtttt tccataggct ccgcccccct gacgagcatc acaaaaatcg   5460
```

-continued

```
acgctcaagt cagaggtggc gaaacccgac aggactataa agataccagg cgtttccccc   5520

tggaagctcc ctcgtgcgct ctcctgttcc gaccctgccg cttaccggat acctgtccgc   5580

ctttctccct tcgggaagcg tggcgctttc tcatagctca cgctgtaggt atctcagttc   5640

ggtgtaggtc gttcgctcca agctgggctg tgtgcacgaa ccccccgttc agcccgaccg   5700

ctgcgcctta tccggtaact atcgtcttga gtccaacccg gtaagacacg acttatcgcc   5760

actggcagca gccactggta acaggattag cagagcgagg tatgtaggcg gtgctacaga   5820

gttcttgaag tggtggccta actacggcta cactagaaga acagtatttg gtatctgcgc   5880

tctgctgaag ccagttacct tcggaaaaag agttggtagc tcttgatccg gcaaacaaac   5940

caccgctggt agcggtggtt tttttgtttg caagcagcag attacgcgca gaaaaaaagg   6000

atctcaagaa gatcctttga tcttttctac ggggtctgac gctcagtgga acgaaaactc   6060

acgttaaggg attttggtca tgagattatc aaaaaggatc ttcacctaga tccttttggg   6120

gtgggcgaag aactccagca tgagatcccc gcgctggagg atcatccagc cctgatagaa   6180

acagaagcca ctggagcacc tcaaaaacac catcatacac taaatcagta agttggcagc   6240

atcacccgac gcactttgcg ccgaataaat acctgtgacg gaagatcact tcgcagaata   6300

aataaatcct ggtgtccctg ttgataccgg gaagccctgg gccaactttt ggcgaaaatg   6360

agacgttgat cggcacgtaa gaggttccaa ctttcaccat aatgaaataa gatcactacc   6420

gggcgtattt tttgagttat cgagattttc aggagctgat agaaacagaa gccactggag   6480

cacctcaaaa acaccatcat acactaaatc agtaagttgg cagcatcacc cgacgcactt   6540

tgcgccgaat aaatacctgt gacggaagat cacttcgcag aataaataaa tcctggtgtc   6600

cctgttgata ccgggaagcc ctgggccaac ttttggcgaa aatgagacgt tgatcggcac   6660

gtaagaggtt ccaactttca ccataatgaa ataagatcac taccgggcgt atttttttgag  6720

ttatcgagat tttcaggagc tctttggcat cgtctctcgc ctgtcccctc agttcagtaa   6780

tttcctgcat ttgcctgttt ccagtcggta gatattccac aaaacagcag ggaagcagcg   6840

cttttccgct gcataaccct gcttcggggt cattatagcg attttttcgg tatatccatc   6900

ctttttcgca cgatatacag gattttgcca aagggttcgt gtagactttc cttggtgtat   6960

ccaacggcgt cagccgggca ggataggtga agtaggccca cccgcgagcg ggtgttcctt   7020

cttcactgtc ccttattcgc acctggcggt gctcaacggg aatcctgctc tgcgaggctg   7080

gccggctacc gccggcgtaa cagatgaggg caagcggatg gctgatgaaa ccaagccaac   7140

caggaagggc agcccaccta tcaaggtgta ctgccttcca gacgaacgaa gagcgattga   7200

ggaaaaggcg gcggcggccg gcatgagcct gtcggcctac ctgctggccg tcggccaggg   7260

ctacaaaatc acgggcgtcg tggactatga gcacgtccgc gagggcgtcc cggaaaacga   7320

ttccgaagcc caacctttca tagaaggcgg cggtggaatc gaaatctcgt gatggcaggt   7380

tgggcgtcgc ttggtcggtc atttcgctcg gtacccatcg gcattttctt ttgcgttt     7438
```

```
<210> SEQ ID NO 15
<211> LENGTH: 52
<212> TYPE: DNA
<213> ORGANISM: Corynebacterium glutamicum

<400> SEQUENCE: 15

cccgggatcc gctagcggcg cgccggccgg cccggtgtga aataccgcac ag            52


<210> SEQ ID NO 16
<211> LENGTH: 53
```

<212> TYPE: DNA
<213> ORGANISM: Corynebacterium glutamicum

<400> SEQUENCE: 16
tctagactcg agcggccgcg gccggccttt aaattgaaga cgaaagggcc tcg 53

<210> SEQ ID NO 17
<211> LENGTH: 47
<212> TYPE: DNA
<213> ORGANISM: Corynebacterium glutamicum

<400> SEQUENCE: 17
gagatctaga cccggggatc cgctagcggg ctgctaaagg aagcgga 47

<210> SEQ ID NO 18
<211> LENGTH: 38
<212> TYPE: DNA
<213> ORGANISM: Corynebacterium glutamicum

<400> SEQUENCE: 18
gagaggcgcg ccgctagcgt gggcgaagaa ctccagca 38

<210> SEQ ID NO 19
<211> LENGTH: 34
<212> TYPE: DNA
<213> ORGANISM: Corynebacterium glutamicum

<400> SEQUENCE: 19
gagagggcgg ccgcgcaaag tcccgcttcg tgaa 34

<210> SEQ ID NO 20
<211> LENGTH: 34
<212> TYPE: DNA
<213> ORGANISM: Corynebacterium glutamicum

<400> SEQUENCE: 20
gagagggcgg ccgctcaagt cggtcaagcc acgc 34

<210> SEQ ID NO 21
<211> LENGTH: 140
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
tcgaatttaa atctcgagag gcctgacgtc gggcccggta ccacgcgtca tatgactagt 60
tcggacctag ggatatcgtc gacatcgatg ctcttctgcg ttaattaaca attgggatcc 120
tctagacccg ggatttaaat 140

<210> SEQ ID NO 22
<211> LENGTH: 140
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
gatcatttaa atcccgggtc tagaggatcc caattgttaa ttaacgcaga agagcatcga 60
tgtcgacgat atccctaggt ccgaactagt catatgacgc gtggtaccgg gcccgacgtc 120
aggcctctcg agatttaaat 140

<210> SEQ ID NO 23
<211> LENGTH: 5091
<212> TYPE: DNA
<213> ORGANISM: Artificial Sequence
<220> FEATURE:
<223> OTHER INFORMATION: Description of Artificial Sequence: Synthetic
construct

<400> SEQUENCE: 23
tcgatttaaa tctcgagagg cctgacgtcg ggcccggtac cacgcgtcat atgactagtt 60
cggacctagg gatatcgtcg acatcgatgc tcttctgcgt taattaacaa ttgggatcct 120
ctagacccgg gatttaaatc gctagcgggc tgctaaagga agcggaacac gtagaaagcc 180
agtccgcaga aacggtgctg accccggatg aatgtcagct actgggctat ctggacaagg 240
gaaaacgcaa gcgcaaagag aaagcaggta gcttgcagtg ggcttacatg gcgatagcta 300
gactgggcgg ttttatggac agcaagcgaa ccggaattgc cagctggggc gccctctggt 360
aaggttggga agccctgcaa agtaaactgg atggctttct tgccgccaag gatctgatgg 420
cgcaggggat caagatctga tcaagagaca ggatgaggat cgtttcgcat gattgaacaa 480
gatggattgc acgcaggttc tccggccgct tgggtggaga ggctattcgg ctatgactgg 540
gcacaacaga caatcggctg ctctgatgcc gccgtgttcc ggctgtcagc gcaggggcgc 600
ccggttcttt ttgtcaagac cgacctgtcc ggtgccctga atgaactgca ggacgaggca 660
gcgcggctat cgtggctggc cacgacgggc gttccttgcg cagctgtgct cgacgttgtc 720
actgaagcgg gaagggactg gctgctattg ggcgaagtgc cggggcagga tctcctgtca 780
tctcaccttg ctcctgccga gaaagtatcc atcatggctg atgcaatgcg gcggctgcat 840
acgcttgatc cggctacctg cccattcgac caccaagcga aacatcgcat cgagcgagca 900
cgtactcgga tggaagccgg tcttgtcgat caggatgatc tggacgaaga gcatcagggg 960
ctcgcgccag ccgaactgtt cgccaggctc aaggcgcgca tgcccgacgg cgaggatctc 1020
gtcgtgaccc atggcgatgc ctgcttgccg aatatcatgg tggaaaatgg ccgcttttct 1080
ggattcatcg actgtggccg gctgggtgtg gcggaccgct atcaggacat agcgttggct 1140
acccgtgata ttgctgaaga gcttggcggc gaatgggctg accgcttcct cgtgctttac 1200
ggtatcgccg ctcccgattc gcagcgcatc gccttctatc gccttcttga cgagttcttc 1260
tgagcgggac tctggggttc gaaatgaccg accaagcgac gcccaacctg ccatcacgag 1320
atttcgattc caccgccgcc ttctatgaaa ggttgggctt cggaatcgtt ttccgggacg 1380
ccggctggat gatcctccag cgcggggatc tcatgctgga gttcttcgcc cacgctagcg 1440
gcgcgccggc cggcccggtg tgaaataccg cacagatgcg taaggagaaa ataccgcatc 1500
aggcgctctt ccgcttcctc gctcactgac tcgctgcgct cggtcgttcg gctgcggcga 1560
gcggtatcag ctcactcaaa ggcggtaata cggttatcca cagaatcagg ggataacgca 1620
ggaaagaaca tgtgagcaaa aggccagcaa aaggccagga accgtaaaaa ggccgcgttg 1680
ctggcgtttt tccataggct ccgcccccct gacgagcatc acaaaaatcg acgctcaagt 1740
cagaggtggc gaaacccgac aggactataa agataccagg cgtttccccc tggaagctcc 1800
ctcgtgcgct ctcctgttcc gaccctgccg cttaccggat acctgtccgc ctttctccct 1860
tcgggaagcg tggcgctttc tcatagctca cgctgtaggt atctcagttc ggtgtaggtc 1920
gttcgctcca agctgggctg tgtgcacgaa ccccccgttc agcccgaccg ctgcgcctta 1980
tccggtaact atcgtcttga gtccaacccg gtaagacacg acttatcgcc actggcagca 2040

-continued gccactggta acaggattag cagagcgagg tatgtaggcg gtgctacaga gttcttgaag 2100
tggtggccta actacggcta cactagaagg acagtatttg gtatctgcgc tctgctgaag 2160
ccagttacct tcggaaaaag agttggtagc tcttgatccg gcaaacaaac caccgctggt 2220
agcggtggtt tttttgtttg caagcagcag attacgcgca gaaaaaaagg atctcaagaa 2280
gatcctttga tcttttctac ggggtctgac gctcagtgga acgaaaactc acgttaaggg 2340
attttggtca tgagattatc aaaaaggatc ttcacctaga tccttttaaa ggccggccgc 2400
ggccgcgcaa agtcccgctt cgtgaaaatt ttcgtgccgc gtgattttcc gccaaaaact 2460
ttaacgaacg ttcgttataa tggtgtcatg accttcacga cgaagtacta aaattggccc 2520
gaatcatcag ctatggatct ctctgatgtc gcgctggagt ccgacgcgct cgatgctgcc 2580
gtcgatttaa aaacggtgat cggatttttc cgagctctcg atacgacgga cgcgccagca 2640
tcacgagact gggccagtgc cgcgagcgac ctagaaactc tcgtggcgga tcttgaggag 2700
ctggctgacg agctgcgtgc tcggccagcg ccaggaggac gcacagtagt ggaggatgca 2760
atcagttgcg cctactgcgg tggcctgatt cctccccggc ctgacccgcg aggacggcgc 2820
gcaaaatatt gctcagatgc gtgtcgtgcc gcagccagcc gcgagcgcgc caacaaacgc 2880
cacgccgagg agctggaggc ggctaggtcg caaatggcgc tggaagtgcg tcccccgagc 2940
gaaattttgg ccatggtcgt cacagagctg gaagcggcag cgagaattat cgcgatcgtg 3000
gcggtgcccg caggcatgac aaacatcgta aatgccgcgt ttcgtgtgcc gtggccgccc 3060
aggacgtgtc agcgccgcca ccacctgcac cgaatcggca gcagcgtcgc gcgtcgaaaa 3120
agcgcacagg cggcaagaag cgataagctg cacgaatacc tgaaaaatgt tgaacgcccc 3180
gtgagcggta actcacaggg cgtcggctaa cccccagtcc aaacctggga gaaagcgctc 3240
aaaaatgact ctagcggatt cacgagacat tgacacaccg gcctggaaat tttccgctga 3300
tctgttcgac acccatcccg agctcgcgct gcgatcacgt ggctggacga gcgaagaccg 3360
ccgcgaattc ctcgctcacc tgggcagaga aaatttccag ggcagcaaga cccgcgactt 3420
cgccagcgct tggatcaaag acccggacac ggagaaacac agccgaagtt ataccgagtt 3480
ggttcaaaat cgcttgcccg gtgccagtat gttgctctga cgcacgcgca gcacgcagcc 3540
gtgcttgtcc tggacattga tgtgccgagc caccaggccg gcgggaaaat cgagcacgta 3600
aaccccgagg tctacgcgat tttggagcgc tgggcacgcc tggaaaaagc gccagcttgg 3660
atcggcgtga atccactgag cgggaaatgc cagctcatct ggctcattga tccggtgtat 3720
gccgcagcag gcatgagcag cccgaatatg cgcctgctgg ctgcaacgac cgaggaaatg 3780
acccgcgttt tcggcgctga ccaggctttt tcacataggc tgagccgtgg ccactgcact 3840
ctccgacgat cccagccgta ccgctggcat gcccagcaca atcgcgtgga tcgcctagct 3900
gatcttatgg aggttgctcg catgatctca ggcacagaaa aacctaaaaa acgctatgag 3960
caggagtttt ctagcggacg ggcacgtatc gaagcggcaa gaaaagccac tgcggaagca 4020
aaagcacttg ccacgcttga agcaagcctg ccgagcgccg ctgaagcgtc tggagagctg 4080
atcgacggcg tccgtgtcct ctggactgct ccagggcgtg ccgcccgtga tgagacggct 4140
tttcgccacg ctttgactgt gggataccag ttaaaagcgg ctggtgagcg cctaaaagac 4200
accaagggtc atcgagccta cgagcgtgcc tacaccgtcg ctcaggcggt cggaggaggc 4260
cgtgagcctg atctgccgcc ggactgtgac cgccagacgg attggccgcg acgtgtgcgc 4320
ggctacgtcg ctaaaggcca gccagtcgtc cctgctcgtc agacagagac gcagagccag 4380
ccgaggcgaa aagctctggc cactatggga agacgtggcg gtaaaaaggc cgcagaacgc 4440

```
tggaaagacc caaacagtga gtacgcccga gcacagcgag aaaaactagc taagtccagt   4500

caacgacaag ctaggaaagc taaaggaaat cgcttgacca ttgcaggttg gtttatgact   4560

gttgagggag agactggctc gtggccgaca atcaatgaag ctatgtctga atttagcgtg   4620

tcacgtcaga ccgtgaatag agcacttaag gtctgcgggc attgaacttc cacgaggacg   4680

ccgaaagctt cccagtaaat gtgccatctc gtaggcagaa aacggttccc ccgtagggtc   4740

tctctcttgg cctcctttct aggtcgggct gattgctctt gaagctctct aggggggctc   4800

acaccatagg cagataacgt tccccaccgg ctcgcctcgt aagcgcacaa ggactgctcc   4860

caaagatctt caaagccact gccgcgactg ccttcgcgaa gccttgcccc gcggaaattt   4920

cctccaccga gttcgtgcac accccctatgc caagcttctt tcaccctaaa ttcgagagat   4980

tggattctta ccgtggaaat tcttcgcaaa aatcgtcccc tgatcgccct tgcgacgttg   5040

gcgtcggtgc cgctggttgc gcttggcttg accgacttga tcagcggccg c           5091
```

<210> SEQ ID NO 24
<211> LENGTH: 28
<212> TYPE: DNA
<213> ORGANISM: Corynebacterium glutamicum

<400> SEQUENCE: 24

```
gcgcggtacc tagactcacc ccagtgct                                        28
```

<210> SEQ ID NO 25
<211> LENGTH: 30
<212> TYPE: DNA
<213> ORGANISM: Corynebacterium glutamicum

<400> SEQUENCE: 25

```
ctctactagt ttagatgtag aactcgatgt                                      30
```

<210> SEQ ID NO 26
<211> LENGTH: 6349
<212> TYPE: DNA
<213> ORGANISM: Artificial Sequence
<220> FEATURE:
<223> OTHER INFORMATION: Description of Artificial Sequence: Synthetic construct

<400> SEQUENCE: 26

```
tcgatttaaa tctcgagagg cctgacgtcg ggcccggtac ctagactcac cccagtgctt     60

aaagcgctgg gtttttcttt ttcagactcg tgagaatgca aactagacta gacagagctg    120

tccatataca ctggacgaag ttttagtctt gtccacccag aacaggcggt tattttcatg    180

cccaccctcg cgccttcagg tcaacttgaa atccaagcga tcggtgatgt ctccaccgaa    240

gccggagcaa tcattacaaa cgctgaaatc gcctatcacc gctggggtga ataccgcgta    300

gataaagaag gacgcagcaa tgtcgttctc atcgaacacg ccctcactgg agattccaac    360

gcagccgatt ggtgggctga cttgctcggt cccggcaaag ccatcaacac tgatatttac    420

tgcgtgatct gtaccaacgt catcggtggt tgcaacggtt ccaccggacc tggctccatg    480

catccagatg gaaatttctg ggtaatcgc ttccccgcca cgtccattcg tgatcaggta    540

aacgccgaaa aacaattcct cgacgcactc ggcatcacca cggtcgccgc agtacttggt    600

ggttccatgg gtggtgcccg caccctagag tgggccgcaa tgtacccaga aactgttggc    660

gcagctgctg ttcttgcagt ttctgcacgc gccagcgcct ggcaaatcgg cattcaatcc    720

gcccaaatta aggcgattga aaacgaccac cactggcacg aaggcaacta ctacgaatcc    780

ggctgcaacc cagccaccgg actcggcgcc gcccgacgca tcgcccacct cacctaccgt    840
```

```
ggcgaactag aaatcgacga acgcttcggc accaaagccc aaaagaacga aaacccactc    900
ggtccctacc gcaagcccga ccagcgcttc gccgtggaat cctacttgga ctaccaagca    960
gacaagctag tacagcgttt cgacgccggc tcctacgtct tgctcaccga cgccctcaac   1020
cgccacgaca ttggtcgcga ccgcggaggc ctcaacaagg cactcgaatc catcaaagtt   1080
ccagtccttg tcgcaggcgt agataccgat attttgtacc cctaccacca gcaagaacac   1140
ctctccagaa acctgggaaa tctactggca atggcaaaaa tcgtatcccc tgtcggccac   1200
gatgctttcc tcaccgaaag ccgccaaatg gatcgcatcg tgaggaactt cttcagcctc   1260
atctccccag acgaagacaa cccttcgacc tacatcgagt tctacatcta aactagttcg   1320
gacctaggga tatcgtcgac atcgatgctc ttctgcgtta attaacaatt gggatcctct   1380
agacccggga tttaaatcgc tagcgggctg ctaaaggaag cggaacacgt agaaagccag   1440
tccgcagaaa cggtgctgac cccggatgaa tgtcagctac tgggctatct ggacaaggga   1500
aaacgcaagc gcaaagagaa agcaggtagc ttgcagtggg cttacatggc gatagctaga   1560
ctgggcggtt ttatggacag caagcgaacc ggaattgcca gctggggcgc cctctggtaa   1620
ggttgggaag ccctgcaaag taaactggat ggctttcttg ccgccaagga tctgatggcg   1680
caggggatca agatctgatc aagagacagg atgaggatcg tttcgcatga ttgaacaaga   1740
tggattgcac gcaggttctc cggccgcttg ggtggagagg ctattcggct atgactgggc   1800
acaacagaca atcggctgct ctgatgccgc cgtgttccgg ctgtcagcgc aggggcgccc   1860
ggttcttttt gtcaagaccg acctgtccgg tgccctgaat gaactgcagg acgaggcagc   1920
gcggctatcg tggctggcca cgacgggcgt tccttgcgca gctgtgctcg acgttgtcac   1980
tgaagcggga agggactggc tgctattggg cgaagtgccg gggcaggatc tcctgtcatc   2040
tcaccttgct cctgccgaga aagtatccat catggctgat gcaatgcggc ggctgcatac   2100
gcttgatccg gctacctgcc cattcgacca ccaagcgaaa catcgcatcg agcgagcacg   2160
tactcggatg gaagccggtc ttgtcgatca ggatgatctg gacgaagagc atcaggggct   2220
cgcgccagcc gaactgttcg ccaggctcaa ggcgcgcatg cccgacggcg aggatctcgt   2280
cgtgacccat ggcgatgcct gcttgccgaa tatcatggtg gaaaatggcc gcttttctgg   2340
attcatcgac tgtggccggc tgggtgtggc ggaccgctat caggacatag cgttggctac   2400
ccgtgatatt gctgaagagc ttggcggcga atgggctgac cgcttcctcg tgctttacgg   2460
tatcgccgct cccgattcgc agcgcatcgc cttctatcgc cttcttgacg agttcttctg   2520
agcgggactc tggggttcga aatgaccgac caagcgacgc ccaacctgcc atcacgagat   2580
ttcgattcca ccgccgcctt ctatgaaagg ttgggcttcg gaatcgtttt ccgggacgcc   2640
ggctggatga tcctccagcg cggggatctc atgctggagt tcttcgccca cgctagcggc   2700
gcgccggccg gcccggtgtg aaataccgca cagatgcgta aggagaaaat accgcatcag   2760
gcgctcttcc gcttcctcgc tcactgactc gctgcgctcg gtcgttcggc tgcggcgagc   2820
ggtatcagct cactcaaagg cggtaatacg gttatccaca gaatcagggg ataacgcagg   2880
aaagaacatg tgagcaaaag gccagcaaaa ggccaggaac cgtaaaaagg ccgcgttgct   2940
ggcgtttttc cataggctcc gcccccctga cgagcatcac aaaaatcgac gctcaagtca   3000
gaggtggcga aacccgacag gactataaag ataccaggcg tttccccctg gaagctccct   3060
cgtgcgctct cctgttccga ccctgccgct taccggatac ctgtccgcct ttctcccttc   3120
gggaagcgtg gcgctttctc atagctcacg ctgtaggtat ctcagttcgg tgtaggtcgt   3180
tcgctccaag ctgggctgtg tgcacgaacc ccccgttcag cccgaccgct gcgccttatc   3240
```

-continued

```
cggtaactat cgtcttgagt ccaacccggt aagacacgac ttatcgccac tggcagcagc   3300
cactggtaac aggattagca gagcgaggta tgtaggcggt gctacagagt tcttgaagtg   3360
gtggcctaac tacggctaca ctagaaggac agtatttggt atctgcgctc tgctgaagcc   3420
agttaccttc ggaaaaagag ttggtagctc ttgatccggc aaacaaacca ccgctggtag   3480
cggtggtttt tttgtttgca agcagcagat tacgcgcaga aaaaaaggat ctcaagaaga   3540
tcctttgatc ttttctacgg ggtctgacgc tcagtggaac gaaaactcac gttaagggat   3600
tttggtcatg agattatcaa aaaggatctt cacctagatc cttttaaagg ccggccgcgg   3660
ccgcgcaaag tcccgcttcg tgaaaatttt cgtgccgcgt gattttccgc caaaaacttt   3720
aacgaacgtt cgttataatg gtgtcatgac cttcacgacg aagtactaaa attggcccga   3780
atcatcagct atggatctct ctgatgtcgc gctggagtcc gacgcgctcg atgctgccgt   3840
cgatttaaaa acggtgatcg gatttttccg agctctcgat acgacggacg cgccagcatc   3900
acgagactgg gccagtgccg cgagcgacct agaaactctc gtggcggatc ttgaggagct   3960
ggctgacgag ctgcgtgctc ggccagcgcc aggaggacgc acagtagtgg aggatgcaat   4020
cagttgcgcc tactgcggtg gcctgattcc tccccggcct gacccgcgag gacggcgcgc   4080
aaaatattgc tcagatgcgt gtcgtgccgc agccagccgc gagcgcgcca acaaacgcca   4140
cgccgaggag ctggaggcgg ctaggtcgca aatggcgctg gaagtgcgtc ccccgagcga   4200
aattttggcc atggtcgtca cagagctgga agcggcagcg agaattatcg cgatcgtggc   4260
ggtgcccgca ggcatgacaa acatcgtaaa tgccgcgttt cgtgtgccgt ggccgcccag   4320
gacgtgtcag cgccgccacc acctgcaccg aatcggcagc agcgtcgcgc gtcgaaaaag   4380
cgcacaggcg gcaagaagcg ataagctgca cgaatacctg aaaaatgttg aacgccccgt   4440
gagcggtaac tcacagggcg tcggctaacc cccagtccaa acctgggaga aagcgctcaa   4500
aaatgactct agcggattca cgagacattg acacaccggc ctggaaattt tccgctgatc   4560
tgttcgacac ccatcccgag ctcgcgctgc gatcacgtgg ctggacgagc gaagaccgcc   4620
gcgaattcct cgctcacctg ggcagagaaa atttccaggg cagcaagacc cgcgacttcg   4680
ccagcgcttg gatcaaagac ccggacacgg agaaacacag ccgaagttat accgagttgg   4740
ttcaaaatcg cttgcccggt gccagtatgt tgctctgacg cacgcgcagc acgcagccgt   4800
gcttgtcctg gacattgatg tgccgagcca ccaggccggc gggaaaatcg agcacgtaaa   4860
ccccgaggtc tacgcgattt tggagcgctg ggcacgcctg gaaaaagcgc cagcttggat   4920
cggcgtgaat ccactgagcg ggaaatgcca gctcatctgg ctcattgatc cggtgtatgc   4980
cgcagcaggc atgagcagcc cgaatatgcg cctgctggct gcaacgaccg aggaaatgac   5040
ccgcgttttc ggcgctgacc aggctttttc acataggctg agccgtggcc actgcactct   5100
ccgacgatcc cagccgtacc gctggcatgc ccagcacaat cgcgtggatc gcctagctga   5160
tcttatggag gttgctcgca tgatctcagg cacagaaaaa cctaaaaaac gctatgagca   5220
ggagttttct agcggacggg cacgtatcga agcggcaaga aaagccactg cggaagcaaa   5280
agcacttgcc acgcttgaag caagcctgcc gagcgccgct gaagcgtctg gagagctgat   5340
cgacggcgtc cgtgtcctct ggactgctcc agggcgtgcc gcccgtgatg agacggcttt   5400
tcgccacgct ttgactgtgg gataccagtt aaaagcggct ggtgagcgcc taaaagacac   5460
caagggtcat cgagcctacg agcgtgccta caccgtcgct caggcggtcg gaggaggccg   5520
tgagcctgat ctgccgccgg actgtgaccg ccagacggat tggccgcgac gtgtgcgcgg   5580
ctacgtcgct aaaggccagc cagtcgtccc tgctcgtcag acagagacgc agagccagcc   5640
```

gaggcgaaaa gctctggcca ctatgggaag acgtggcggt aaaaaggccg cagaacgctg 5700
gaaagaccca aacagtgagt acgcccgagc acagcgagaa aaactagcta agtccagtca 5760
acgacaagct aggaaagcta aaggaaatcg cttgaccatt gcaggttggt ttatgactgt 5820
tgagggagag actggctcgt ggccgacaat caatgaagct atgtctgaat ttagcgtgtc 5880
acgtcagacc gtgaatagag cacttaaggt ctgcgggcat tgaacttcca cgaggacgcc 5940
gaaagcttcc cagtaaatgt gccatctcgt aggcagaaaa cggttccccc gtagggtctc 6000
tctcttggcc tcctttctag gtcgggctga ttgctcttga agctctctag gggggctcac 6060
accataggca gataacgttc cccaccggct cgcctcgtaa gcgcacaagg actgctccca 6120
aagatcttca aagccactgc cgcgactgcc ttcgcgaagc cttgccccgc ggaaatttcc 6180
tccaccgagt tcgtgcacac ccctatgcca agcttctttc accctaaatt cgagagattg 6240
gattcttacc gtggaaattc ttcgcaaaaa tcgtcccctg atcgcccttg cgacgttggc 6300
gtcggtgccg ctggttgcgc ttggcttgac cgacttgatc agcggccgc 6349

<210> SEQ ID NO 27
<211> LENGTH: 30
<212> TYPE: DNA
<213> ORGANISM: Corynebacterium glutamicum

<400> SEQUENCE: 27
gagactcgag cggcttaaag tttggctgcc 30

<210> SEQ ID NO 28
<211> LENGTH: 41
<212> TYPE: DNA
<213> ORGANISM: Corynebacterium glutamicum

<400> SEQUENCE: 28
cctgaaggcg cgagggtggg catgatgaat ccctccatga g 41

<210> SEQ ID NO 29
<211> LENGTH: 19
<212> TYPE: DNA
<213> ORGANISM: Corynebacterium glutamicum

<400> SEQUENCE: 29
cccaccctcg cgccttcag 19

<210> SEQ ID NO 30
<211> LENGTH: 18
<212> TYPE: DNA
<213> ORGANISM: Corynebacterium glutamicum

<400> SEQUENCE: 30
ctgggtacat tgcggccc 18

<210> SEQ ID NO 31
<211> LENGTH: 6372
<212> TYPE: DNA
<213> ORGANISM: Artificial Sequence
<220> FEATURE:
<223> OTHER INFORMATION: Description of Artificial Sequence: Synthetic
construct

<400> SEQUENCE: 31
agcggcttaa agtttggctg ccatgtgaat ttttagcacc ctcaacagtt gagtgctggc 60
actctcgggg gtagagtgcc aaataggttg tttgacacac agttgttcac ccgcgacgac 120

-continued

```
ggctgtgctg gaaacccaca accggcacac acaaaatttt tctcatggag ggattcatca    180
tgcccaccct cgcgccttca ggtcaacttg aaatccaagc gatcggtgat gtctccaccg    240
aagccggagc aatcattaca aacgctgaaa tcgcctatca ccgctggggt gaataccgcg    300
tagataaaga aggacgcagc aatgtcgttc tcatcgaaca cgccctcact ggagattcca    360
acgcagccga ttggtgggct gacttgctcg gtcccggcaa agccatcaac actgatattt    420
actgcgtgat ctgtaccaac gtcatcggtg gttgcaacgg ttccaccgga cctggctcca    480
tgcatccaga tggaaatttc tggggtaatc gcttccccgc cacgtccatt cgtgatcagg    540
taaacgccga aaaacaattc ctcgacgcac tcggcatcac cacggtcgcc gcagtacttg    600
gtggttccat gggtggtgcc cgcaccctag agtgggccgc aatgtaccca gaaactgttg    660
gcgcagctgc tgttcttgca gtttctgcac gcgccagcgc ctggcaaatc ggcattcaat    720
ccgcccaaat taaggcgatt gaaaacgacc accactggca cgaaggcaac tactacgaat    780
ccggctgcaa cccagccacc ggactcggcg ccgcccgacg catcgcccac ctcacctacc    840
gtggcgaact agaaatcgac gaacgcttcg gcaccaaagc ccaaaagaac gaaaacccac    900
tcggtcccta ccgcaagccc gaccagcgct tcgccgtgga atcctacttg gactaccaag    960
cagacaagct agtacagcgt ttcgacgccg gctcctacgt cttgctcacc gacgccctca   1020
accgccacga cattggtcgc gaccgcggag gcctcaacaa ggcactcgaa tccatcaaag   1080
ttccagtcct tgtcgcaggc gtagataccg atattttgta cccctaccac cagcaagaac   1140
acctctccag aaacctggga aatctactgg caatggcaaa aatcgtatcc cctgtcggcc   1200
acgatgcttt cctcaccgaa agccgccaaa tggatcgcat cgtgaggaac ttcttcagcc   1260
tcatctcccc agacgaagac aacccttcga cctacatcga gttctacatc taacatatga   1320
ctagttcgga cctagggata tcgtcgacat cgatgctctt ctgcgttaat taacaattgg   1380
gatcctctag acccgggatt taaatcgcta gcgggctgct aaaggaagcg gaacacgtag   1440
aaagccagtc cgcagaaacg gtgctgaccc cggatgaatg tcagctactg ggctatctgg   1500
acaagggaaa acgcaagcgc aaagagaaag caggtagctt gcagtgggct tacatggcga   1560
tagctagact gggcggtttt atggacagca agcgaaccgg aattgccagc tggggcgccc   1620
tctggtaagg ttgggaagcc ctgcaaagta aactggatgg ctttcttgcc gccaaggatc   1680
tgatggcgca ggggatcaag atctgatcaa gagacaggat gaggatcgtt tcgcatgatt   1740
gaacaagatg gattgcacgc aggttctccg gccgcttggg tggagaggct attcggctat   1800
gactgggcac aacagacaat cggctgctct gatgccgccg tgttccggct gtcagcgcag   1860
gggcgcccgg ttctttttgt caagaccgac ctgtccggtg ccctgaatga actgcaggac   1920
gaggcagcgc ggctatcgtg gctggccacg acgggcgttc cttgcgcagc tgtgctcgac   1980
gttgtcactg aagcgggaag ggactggctg ctattgggcg aagtgccggg gcaggatctc   2040
ctgtcatctc accttgctcc tgccgagaaa gtatccatca tggctgatgc aatgcggcgg   2100
ctgcatacgc ttgatccggc tacctgccca ttcgaccacc aagcgaaaca tcgcatcgag   2160
cgagcacgta ctcggatgga agccggtctt gtcgatcagg atgatctgga cgaagagcat   2220
caggggctcg cgccagccga actgttcgcc aggctcaagg cgcgcatgcc cgacggcgag   2280
gatctcgtcg tgacccatgg cgatgcctgc ttgccgaata tcatggtgga aaatggccgc   2340
ttttctggat tcatcgactg tggccggctg ggtgtggcgg accgctatca ggacatagcg   2400
ttggctaccc gtgatattgc tgaagagctt ggcggcgaat gggctgaccg cttcctcgtg   2460
ctttacggta tcgccgctcc cgattcgcag cgcatcgcct tctatcgcct tcttgacgag   2520
```

-continued

```
ttcttctgag cgggactctg gggttcgaaa tgaccgacca agcgacgccc aacctgccat   2580
cacgagattt cgattccacc gccgccttct atgaaaggtt gggcttcgga atcgttttcc   2640
gggacgccgg ctggatgatc ctccagcgcg gggatctcat gctggagttc ttcgcccacg   2700
ctagcggcgc gccggccggc ccggtgtgaa ataccgcaca gatgcgtaag gagaaaatac   2760
cgcatcaggc gctcttccgc ttcctcgctc actgactcgc tgcgctcggt cgttcggctg   2820
cggcgagcgg tatcagctca ctcaaaggcg gtaatacggt tatccacaga atcaggggat   2880
aacgcaggaa agaacatgtg agcaaaaggc cagcaaaagg ccaggaaccg taaaaaggcc   2940
gcgttgctgg cgtttttcca taggctccgc ccccctgacg agcatcacaa aaatcgacgc   3000
tcaagtcaga ggtggcgaaa cccgacagga ctataaagat accaggcgtt tccccctgga   3060
agctccctcg tgcgctctcc tgttccgacc ctgccgctta ccggatacct gtccgccttt   3120
ctcccttcgg gaagcgtggc gctttctcat agctcacgct gtaggtatct cagttcggtg   3180
taggtcgttc gctccaagct gggctgtgtg cacgaacccc ccgttcagcc cgaccgctgc   3240
gccttatccg gtaactatcg tcttgagtcc aacccggtaa gacacgactt atcgccactg   3300
gcagcagcca ctggtaacag gattagcaga gcgaggtatg taggcggtgc tacagagttc   3360
ttgaagtggt ggcctaacta cggctacact agaaggacag tatttggtat ctgcgctctg   3420
ctgaagccag ttaccttcgg aaaaagagtt ggtagctctt gatccggcaa acaaaccacc   3480
gctggtagcg gtggtttttt tgtttgcaag cagcagatta cgcgcagaaa aaaaggatct   3540
caagaagatc ctttgatctt ttctacgggg tctgacgctc agtggaacga aaactcacgt   3600
taagggattt tggtcatgag attatcaaaa aggatcttca cctagatcct tttaaaggcc   3660
ggccgcggcc gcgcaaagtc ccgcttcgtg aaaattttcg tgccgcgtga ttttccgcca   3720
aaaactttaa cgaacgttcg ttataatggt gtcatgacct tcacgacgaa gtactaaaat   3780
tggcccgaat catcagctat ggatctctct gatgtcgcgc tggagtccga cgcgctcgat   3840
gctgccgtcg atttaaaaac ggtgatcgga tttttccgag ctctcgatac gacggacgcg   3900
ccagcatcac gagactgggc cagtgccgcg agcgacctag aaactctcgt ggcggatctt   3960
gaggagctgg ctgacgagct gcgtgctcgg ccagcgccag gaggacgcac agtagtggag   4020
gatgcaatca gttgcgccta ctgcggtggc ctgattcctc cccggcctga cccgcgagga   4080
cggcgcgcaa aatattgctc agatgcgtgt cgtgccgcag ccagccgcga gcgcgccaac   4140
aaacgccacg ccgaggagct ggaggcggct aggtcgcaaa tggcgctgga agtgcgtccc   4200
ccgagcgaaa ttttggccat ggtcgtcaca gagctggaag cggcagcgag aattatcgcg   4260
atcgtggcgg tgcccgcagg catgacaaac atcgtaaatg ccgcgtttcg tgtgccgtgg   4320
ccgcccagga cgtgtcagcg ccgccaccac ctgcaccgaa tcggcagcag cgtcgcgcgt   4380
cgaaaaagcg cacaggcggc aagaagcgat aagctgcacg aatacctgaa aaatgttgaa   4440
cgccccgtga gcggtaactc acagggcgtc ggctaacccc cagtccaaac ctgggagaaa   4500
gcgctcaaaa atgactctag cggattcacg agacattgac acaccggcct ggaaattttc   4560
cgctgatctg ttcgacaccc atcccgagct cgcgctgcga tcacgtggct ggacgagcga   4620
agaccgccgc gaattcctcg ctcacctggg cagagaaaat ttccagggca gcaagacccg   4680
cgacttcgcc agcgcttgga tcaaagaccc ggacacggag aaacacagcc gaagttatac   4740
cgagttggtt caaaatcgct tgcccggtgc cagtatgttg ctctgacgca cgcgcagcac   4800
gcagccgtgc ttgtcctgga cattgatgtg ccgagccacc aggccggcgg gaaaatcgag   4860
cacgtaaacc ccgaggtcta cgcgattttg gagcgctggg cacgcctgga aaaagcgcca   4920
```

gcttggatcg gcgtgaatcc actgagcggg aaatgccagc tcatctggct cattgatccg 4980
gtgtatgccg cagcaggcat gagcagcccg aatatgcgcc tgctggctgc aacgaccgag 5040
gaaatgaccc gcgttttcgg cgctgaccag gctttttcac ataggctgag ccgtggccac 5100
tgcactctcc gacgatccca gccgtaccgc tggcatgccc agcacaatcg cgtggatcgc 5160
ctagctgatc ttatggaggt tgctcgcatg atctcaggca cagaaaaacc taaaaaacgc 5220
tatgagcagg agttttctag cggacgggca cgtatcgaag cggcaagaaa agccactgcg 5280
gaagcaaaag cacttgccac gcttgaagca agcctgccga gcgccgctga agcgtctgga 5340
gagctgatcg acggcgtccg tgtcctctgg actgctccag ggcgtgccgc ccgtgatgag 5400
acggcttttc gccacgcttt gactgtggga taccagttaa aagcggctgg tgagcgccta 5460
aaagacacca agggtcatcg agcctacgag cgtgcctaca ccgtcgctca ggcggtcgga 5520
ggaggccgtg agcctgatct gccgccggac tgtgaccgcc agacggattg gccgcgacgt 5580
gtgcgcggct acgtcgctaa aggccagcca gtcgtccctg ctcgtcagac agagacgcag 5640
agccagccga ggcgaaaagc tctggccact atgggaagac gtggcggtaa aaaggccgca 5700
gaacgctgga aagacccaaa cagtgagtac gcccgagcac agcgagaaaa actagctaag 5760
tccagtcaac gacaagctag gaaagctaaa ggaaatcgct tgaccattgc aggttggttt 5820
atgactgttg agggagagac tggctcgtgg ccgacaatca atgaagctat gtctgaattt 5880
agcgtgtcac gtcagaccgt gaatagagca cttaaggtct gcgggcattg aacttccacg 5940
aggacgccga aagcttccca gtaaatgtgc catctcgtag gcagaaaacg gttcccccgt 6000
agggtctctc tcttggcctc ctttctaggt cgggctgatt gctcttgaag ctctctaggg 6060
gggctcacac cataggcaga taacgttccc caccggctcg cctcgtaagc gcacaaggac 6120
tgctcccaaa gatcttcaaa gccactgccg cgactgcctt cgcgaagcct tgccccgcgg 6180
aaatttcctc caccgagttc gtgcacaccc ctatgccaag cttctttcac cctaaattcg 6240
agagattgga ttcttaccgt ggaaattctt cgcaaaaatc gtcccctgat cgcccttgcg 6300
acgttggcgt cggtgccgct ggttgcgctt ggcttgaccg acttgatcag cggccgctcg 6360
atttaaatct cg 6372

<210> SEQ ID NO 32
<211> LENGTH: 29
<212> TYPE: DNA
<213> ORGANISM: Corynebacterium glutamicum

<400> SEQUENCE: 32
ggatctagag ttctgtgaaa aacaccgtg 29

<210> SEQ ID NO 33
<211> LENGTH: 29
<212> TYPE: DNA
<213> ORGANISM: Corynebacterium glutamicum

<400> SEQUENCE: 33
gcgactagtg ccccacaaat aaaaaacac 29

<210> SEQ ID NO 34
<211> LENGTH: 5156
<212> TYPE: DNA
<213> ORGANISM: Artificial Sequence
<220> FEATURE:
<223> OTHER INFORMATION: Description of Artificial Sequence: Synthetic
construct

<400> SEQUENCE: 34

-continued

```
tcgatttaaa tctcgagagg cctgacgtcg ggcccggtac cacgcgtcat atgactagtt     60
cggacctagg gatatcgtcg acatcgatgc tcttctgcgt taattaacaa ttgggatcct    120
ctagagttct gtgaaaaaca ccgtggggca gtttctgctt cgcggtgttt tttatttgtg    180
gggcactaga cccgggattt aaatcgctag cgggctgcta aaggaagcgg aacacgtaga    240
aagccagtcc gcagaaacgg tgctgacccc ggatgaatgt cagctactgg gctatctgga    300
caagggaaaa cgcaagcgca aagagaaagc aggtagcttg cagtgggctt acatggcgat    360
agctagactg ggcggtttta tggacagcaa gcgaaccgga attgccagct ggggcgccct    420
ctggtaaggt tgggaagccc tgcaaagtaa actggatggc tttcttgccg ccaaggatct    480
gatggcgcag gggatcaaga tctgatcaag agacaggatg aggatcgttt cgcatgattg    540
aacaagatgg attgcacgca ggttctccgg ccgcttgggt ggagaggcta ttcggctatg    600
actgggcaca acagacaatc ggctgctctg atgccgccgt gttccggctg tcagcgcagg    660
ggcgcccggt tctttttgtc aagaccgacc tgtccggtgc cctgaatgaa ctgcaggacg    720
aggcagcgcg gctatcgtgg ctggccacga cgggcgttcc ttgcgcagct gtgctcgacg    780
ttgtcactga agcgggaagg gactggctgc tattgggcga agtgccgggg caggatctcc    840
tgtcatctca ccttgctcct gccgagaaag tatccatcat ggctgatgca atgcggcggc    900
tgcatacgct tgatccggct acctgcccat tcgaccacca agcgaaacat cgcatcgagc    960
gagcacgtac tcggatggaa gccggtcttg tcgatcagga tgatctggac gaagagcatc   1020
aggggctcgc gccagccgaa ctgttcgcca ggctcaaggc gcgcatgccc gacggcgagg   1080
atctcgtcgt gacccatggc gatgcctgct tgccgaatat catggtggaa aatggccgct   1140
tttctggatt catcgactgt ggccggctgg gtgtggcgga ccgctatcag gacatagcgt   1200
tggctacccg tgatattgct gaagagcttg gcggcgaatg ggctgaccgc ttcctcgtgc   1260
tttacggtat cgccgctccc gattcgcagc gcatcgcctt ctatcgcctt cttgacgagt   1320
tcttctgagc gggactctgg ggttcgaaat gaccgaccaa gcgacgccca acctgccatc   1380
acgagatttc gattccaccg ccgccttcta tgaaaggttg ggcttcggaa tcgttttccg   1440
ggacgccggc tggatgatcc tccagcgcgg ggatctcatg ctggagttct tcgcccacgc   1500
tagcggcgcg ccggccggcc cggtgtgaaa taccgcacag atgcgtaagg agaaaatacc   1560
gcatcaggcg ctcttccgct tcctcgctca ctgactcgct gcgctcggtc gttcggctgc   1620
ggcgagcggt atcagctcac tcaaaggcgg taatacggtt atccacagaa tcaggggata   1680
acgcaggaaa gaacatgtga gcaaaaggcc agcaaaaggc caggaaccgt aaaaaggccg   1740
cgttgctggc gtttttccat aggctccgcc cccctgacga gcatcacaaa aatcgacgct   1800
caagtcagag gtggcgaaac ccgacaggac tataaagata ccaggcgttt ccccctggaa   1860
gctccctcgt gcgctctcct gttccgaccc tgccgcttac cggatacctg tccgcctttc   1920
tcccttcggg aagcgtggcg ctttctcata gctcacgctg taggtatctc agttcggtgt   1980
aggtcgttcg ctccaagctg ggctgtgtgc acgaaccccc cgttcagccc gaccgctgcg   2040
ccttatccgg taactatcgt cttgagtcca acccggtaag acacgactta tcgccactgg   2100
cagcagccac tggtaacagg attagcagag cgaggtatgt aggcggtgct acagagttct   2160
tgaagtggtg gcctaactac ggctacacta gaaggacagt atttggtatc tgcgctctgc   2220
tgaagccagt taccttcgga aaaagagttg gtagctcttg atccggcaaa caaaccaccg   2280
ctggtagcgg tggttttttt gtttgcaagc agcagattac gcgcagaaaa aaaggatctc   2340
aagaagatcc tttgatcttt tctacggggt ctgacgctca gtggaacgaa aactcacgtt   2400
```

-continued

```
aagggatttt ggtcatgaga ttatcaaaaa ggatcttcac ctagatcctt ttaaaggccg   2460
gccgcggccg cgcaaagtcc cgcttcgtga aaattttcgt gccgcgtgat tttccgccaa   2520
aaactttaac gaacgttcgt tataatggtg tcatgacctt cacgacgaag tactaaaatt   2580
ggcccgaatc atcagctatg gatctctctg atgtcgcgct ggagtccgac gcgctcgatg   2640
ctgccgtcga tttaaaaacg gtgatcggat ttttccgagc tctcgatacg acggacgcgc   2700
cagcatcacg agactgggcc agtgccgcga gcgacctaga aactctcgtg gcggatcttg   2760
aggagctggc tgacgagctg cgtgctcggc cagcgccagg aggacgcaca gtagtggagg   2820
atgcaatcag ttgcgcctac tgcggtggcc tgattcctcc ccggcctgac ccgcgaggac   2880
ggcgcgcaaa atattgctca gatgcgtgtc gtgccgcagc cagccgcgag cgcgccaaca   2940
aacgccacgc cgaggagctg gaggcggcta ggtcgcaaat ggcgctggaa gtgcgtcccc   3000
cgagcgaaat tttggccatg gtcgtcacag agctggaagc ggcagcgaga attatcgcga   3060
tcgtggcggt gcccgcaggc atgacaaaca tcgtaaatgc cgcgtttcgt gtgccgtggc   3120
cgcccaggac gtgtcagcgc cgccaccacc tgcaccgaat cggcagcagc gtcgcgcgtc   3180
gaaaaagcgc acaggcggca agaagcgata agctgcacga atacctgaaa aatgttgaac   3240
gccccgtgag cggtaactca cagggcgtcg gctaaccccc agtccaaacc tgggagaaag   3300
cgctcaaaaa tgactctagc ggattcacga gacattgaca caccggcctg gaaattttcc   3360
gctgatctgt tcgacaccca tcccgagctc gcgctgcgat cacgtggctg gacgagcgaa   3420
gaccgccgcg aattcctcgc tcacctgggc agagaaaatt tccagggcag caagacccgc   3480
gacttcgcca gcgcttggat caaagacccg gacacggaga aacacagccg aagttatacc   3540
gagttggttc aaaatcgctt gcccggtgcc agtatgttgc tctgacgcac gcgcagcacg   3600
cagccgtgct tgtcctggac attgatgtgc cgagccacca ggccggcggg aaaatcgagc   3660
acgtaaaccc cgaggtctac gcgattttgg agcgctgggc acgcctggaa aaagcgccag   3720
cttggatcgg cgtgaatcca ctgagcggga aatgccagct catctggctc attgatccgg   3780
tgtatgccgc agcaggcatg agcagcccga atatgcgcct gctggctgca acgaccgagg   3840
aaatgacccg cgttttcggc gctgaccagg ctttttcaca taggctgagc cgtggccact   3900
gcactctccg acgatcccag ccgtaccgct ggcatgccca gcacaatcgc gtggatcgcc   3960
tagctgatct tatggaggtt gctcgcatga tctcaggcac agaaaaacct aaaaaacgct   4020
atgagcagga gttttctagc ggacgggcac gtatcgaagc ggcaagaaaa gccactgcgg   4080
aagcaaaagc acttgccacg cttgaagcaa gcctgccgag cgccgctgaa gcgtctggag   4140
agctgatcga cggcgtccgt gtcctctgga ctgctccagg gcgtgccgcc cgtgatgaga   4200
cggcttttcg ccacgctttg actgtgggat accagttaaa agcggctggt gagcgcctaa   4260
aagacaccaa gggtcatcga gcctacgagc gtgcctacac cgtcgctcag gcggtcggag   4320
gaggccgtga gcctgatctg ccgccggact gtgaccgcca gacggattgg ccgcgacgtg   4380
tgcgcggcta cgtcgctaaa ggccagccag tcgtccctgc tcgtcagaca gagacgcaga   4440
gccagccgag gcgaaaagct ctggccacta tgggaagacg tggcggtaaa aaggccgcag   4500
aacgctggaa agacccaaac agtgagtacg cccgagcaca gcgagaaaaa ctagctaagt   4560
ccagtcaacg acaagctagg aaagctaaag gaaatcgctt gaccattgca ggttggttta   4620
tgactgttga gggagagact ggctcgtggc cgacaatcaa tgaagctatg tctgaattta   4680
gcgtgtcacg tcagaccgtg aatagagcac ttaaggtctg cgggcattga acttccacga   4740
ggacgccgaa agcttcccag taaatgtgcc atctcgtagg cagaaaacgg ttcccccgta   4800
```

gggtctctct cttggcctcc tttctaggtc gggctgattg ctcttgaagc tctctagggg 4860
ggctcacacc ataggcagat aacgttcccc accggctcgc ctcgtaagcg cacaaggact 4920
gctcccaaag atcttcaaag ccactgccgc gactgccttc gcgaagcctt gccccgcgga 4980
aatttcctcc accgagttcg tgcacacccc tatgccaagc ttctttcacc ctaaattcga 5040
gagattggat tcttaccgtg gaaattcttc gcaaaaatcg tcccctgatc gcccttgcga 5100
cgttggcgtc ggtgccgctg gttgcgcttg gcttgaccga cttgatcagc ggccgc 5156

<210> SEQ ID NO 35
<211> LENGTH: 30
<212> TYPE: DNA
<213> ORGANISM: Corynebacterium glutamicum

<400> SEQUENCE: 35
gagacatatg cccaccctcg cgccttcagg 30

<210> SEQ ID NO 36
<211> LENGTH: 30
<212> TYPE: DNA
<213> ORGANISM: Corynebacterium glutamicum

<400> SEQUENCE: 36
ctctactagt ttagatgtag aactcgatgt 30

<210> SEQ ID NO 37
<211> LENGTH: 6287
<212> TYPE: DNA
<213> ORGANISM: Artificial Sequence
<220> FEATURE:
<223> OTHER INFORMATION: Description of Artificial Sequence: Synthetic
construct

<400> SEQUENCE: 37
tcgatttaaa tctcgagagg cctgacgtcg ggcccggtac cacgcgtcat atgcccaccc 60
tcgcgccttc aggtcaactt gaaatccaag cgatcggtga tgtctccacc gaagccggag 120
caatcattac aaacgctgaa atcgcctatc accgctgggg tgaataccgc gtagataaag 180
aaggacgcag caatgtcgtt ctcatcgaac acgccctcac tggagattcc aacgcagccg 240
attggtgggc tgacttgctc ggtcccggca aagccatcaa cactgatatt tactgcgtga 300
tctgtaccaa cgtcatcggt ggttgcaacg gttccaccgg acctggctcc atgcatccag 360
atggaaattt ctggggtaat cgcttccccg ccacgtccat tcgtgatcag gtaaacgccg 420
aaaaacaatt cctcgacgca ctcggcatca ccacggtcgc cgcagtactt ggtggttcca 480
tgggtggtgc ccgcacccta gagtgggccg caatgtaccc agaaactgtt ggcgcagctg 540
ctgttcttgc agtttctgca cgcgccagcg cctggcaaat cggcattcaa tccgcccaaa 600
ttaaggcgat tgaaaacgac caccactggc acgaaggcaa ctactacgaa tccggctgca 660
acccagccac cggactcggc gccgcccgac gcatcgccca cctcacctac cgtggcgaac 720
tagaaatcga cgaacgcttc ggcaccaaag cccaaaagaa cgaaaaccca ctcggtccct 780
accgcaagcc cgaccagcgc ttcgccgtgg aatcctactt ggactaccaa gcagacaagc 840
tagtacagcg tttcgacgcc ggctcctacg tcttgctcac cgacgccctc aaccgccacg 900
acattggtcg cgaccgcgga ggcctcaaca aggcactcga atccatcaaa gttccagtcc 960
ttgtcgcagg cgtagatacc gatattttgt accoctacca ccagcaagaa cacctctcca 1020
gaaacctggg aaatctactg gcaatggcaa aaatcgtatc ccctgtcggc cacgatgctt 1080

-continued

```
tcctcaccga aagccgccaa atggatcgca tcgtgaggaa cttcttcagc ctcatctccc   1140
cagacgaaga caacccttcg acctacatcg agttctacat ctaaactagt tcggacctag   1200
ggatatcgtc gacatcgatg ctcttctgcg ttaattaaca attgggatcc tctagagttc   1260
tgtgaaaaac accgtggggc agtttctgct tcgcggtgtt ttttatttgt ggggcactag   1320
acccgggatt taaatcgcta gcgggctgct aaaggaagcg gaacacgtag aaagccagtc   1380
cgcagaaacg gtgctgaccc cggatgaatg tcagctactg ggctatctgg acaagggaaa   1440
acgcaagcgc aaagagaaag caggtagctt gcagtgggct tacatggcga tagctagact   1500
gggcggtttt atggacagca agcgaaccgg aattgccagc tggggcgccc tctggtaagg   1560
ttgggaagcc ctgcaaagta aactggatgg ctttcttgcc gccaaggatc tgatggcgca   1620
ggggatcaag atctgatcaa gagacaggat gaggatcgtt tcgcatgatt gaacaagatg   1680
gattgcacgc aggttctccg gccgcttggg tggagaggct attcggctat gactgggcac   1740
aacagacaat cggctgctct gatgccgccg tgttccggct gtcagcgcag gggcgcccgg   1800
ttctttttgt caagaccgac ctgtccggtg ccctgaatga actgcaggac gaggcagcgc   1860
ggctatcgtg gctggccacg acgggcgttc cttgcgcagc tgtgctcgac gttgtcactg   1920
aagcgggaag ggactggctg ctattgggcg aagtgccggg gcaggatctc ctgtcatctc   1980
accttgctcc tgccgagaaa gtatccatca tggctgatgc aatgcggcgg ctgcatacgc   2040
ttgatccggc tacctgccca ttcgaccacc aagcgaaaca tcgcatcgag cgagcacgta   2100
ctcggatgga agccggtctt gtcgatcagg atgatctgga cgaagagcat caggggctcg   2160
cgccagccga actgttcgcc aggctcaagg cgcgcatgcc cgacggcgag gatctcgtcg   2220
tgacccatgg cgatgcctgc ttgccgaata tcatggtgga aaatggccgc ttttctggat   2280
tcatcgactg tggccggctg ggtgtggcgg accgctatca ggacatagcg ttggctaccc   2340
gtgatattgc tgaagagctt ggcggcgaat gggctgaccg cttcctcgtg ctttacggta   2400
tcgccgctcc cgattcgcag cgcatcgcct tctatcgcct tcttgacgag ttcttctgag   2460
cgggactctg gggttcgaaa tgaccgacca agcgacgccc aacctgccat cacgagattt   2520
cgattccacc gccgccttct atgaaaggtt gggcttcgga atcgttttcc gggacgccgg   2580
ctggatgatc ctccagcgcg gggatctcat gctggagttc ttcgcccacg ctagcggcgc   2640
gccggccggc ccggtgtgaa ataccgcaca gatgcgtaag gagaaaatac cgcatcaggc   2700
gctcttccgc ttcctcgctc actgactcgc tgcgctcggt cgttcggctg cggcgagcgg   2760
tatcagctca ctcaaaggcg gtaatacggt tatccacaga atcaggggat aacgcaggaa   2820
agaacatgtg agcaaaaggc cagcaaaagg ccaggaaccg taaaaaggcc gcgttgctgg   2880
cgtttttcca taggctccgc ccccctgacg agcatcacaa aaatcgacgc tcaagtcaga   2940
ggtggcgaaa cccgacagga ctataaagat accaggcgtt tccccctgga agctccctcg   3000
tgcgctctcc tgttccgacc ctgccgctta ccggatacct gtccgccttt ctcccttcgg   3060
gaagcgtggc gctttctcat agctcacgct gtaggtatct cagttcggtg taggtcgttc   3120
gctccaagct gggctgtgtg cacgaacccc ccgttcagcc cgaccgctgc gccttatccg   3180
gtaactatcg tcttgagtcc aacccggtaa gacacgactt atcgccactg gcagcagcca   3240
ctggtaacag gattagcaga gcgaggtatg taggcggtgc tacagagttc ttgaagtggt   3300
ggcctaacta cggctacact agaaggacag tatttggtat ctgcgctctg ctgaagccag   3360
ttaccttcgg aaaaagagtt ggtagctctt gatccggcaa acaaaccacc gctggtagcg   3420
gtggtttttt tgtttgcaag cagcagatta cgcgcagaaa aaaaggatct caagaagatc   3480
```

-continued

```
ctttgatctt ttctacgggg tctgacgctc agtggaacga aaactcacgt taagggattt   3540

tggtcatgag attatcaaaa aggatcttca cctagatcct tttaaaggcc ggccgcggcc   3600

gcgcaaagtc ccgcttcgtg aaaattttcg tgccgcgtga ttttccgcca aaaactttaa   3660

cgaacgttcg ttataatggt gtcatgacct tcacgacgaa gtactaaaat tggcccgaat   3720

catcagctat ggatctctct gatgtcgcgc tggagtccga cgcgctcgat gctgccgtcg   3780

atttaaaaac ggtgatcgga tttttccgag ctctcgatac gacggacgcg ccagcatcac   3840

gagactgggc cagtgccgcg agcgacctag aaactctcgt ggcggatctt gaggagctgg   3900

ctgacgagct gcgtgctcgg ccagcgccag gaggacgcac agtagtggag gatgcaatca   3960

gttgcgccta ctgcggtggc ctgattcctc cccggcctga cccgcgagga cggcgcgcaa   4020

aatattgctc agatgcgtgt cgtgccgcag ccagccgcga gcgcgccaac aaacgccacg   4080

ccgaggagct ggaggcggct aggtcgcaaa tggcgctgga agtgcgtccc ccgagcgaaa   4140

ttttggccat ggtcgtcaca gagctggaag cggcagcgag aattatcgcg atcgtggcgg   4200

tgcccgcagg catgacaaac atcgtaaatg ccgcgtttcg tgtgccgtgg ccgcccagga   4260

cgtgtcagcg ccgccaccac ctgcaccgaa tcggcagcag cgtcgcgcgt cgaaaaagcg   4320

cacaggcggc aagaagcgat aagctgcacg aatacctgaa aaatgttgaa cgccccgtga   4380

gcggtaactc acagggcgtc ggctaacccc cagtccaaac ctgggagaaa gcgctcaaaa   4440

atgactctag cggattcacg agacattgac acaccggcct ggaaattttc cgctgatctg   4500

ttcgacaccc atcccgagct cgcgctgcga tcacgtggct ggacgagcga agaccgccgc   4560

gaattcctcg ctcacctggg cagagaaaat ttccagggca gcaagacccg cgacttcgcc   4620

agcgcttgga tcaaagaccc ggacacggag aaacacagcc gaagttatac cgagttggtt   4680

caaaatcgct tgcccggtgc cagtatgttg ctctgacgca cgcgcagcac gcagccgtgc   4740

ttgtcctgga cattgatgtg ccgagccacc aggccggcgg gaaaatcgag cacgtaaacc   4800

ccgaggtcta cgcgattttg gagcgctggg cacgcctgga aaaagcgcca gcttggatcg   4860

gcgtgaatcc actgagcggg aaatgccagc tcatctggct cattgatccg gtgtatgccg   4920

cagcaggcat gagcagcccg aatatgcgcc tgctggctgc aacgaccgag gaaatgaccc   4980

gcgttttcgg cgctgaccag gctttttcac ataggctgag ccgtggccac tgcactctcc   5040

gacgatccca gccgtaccgc tggcatgccc agcacaatcg cgtggatcgc ctagctgatc   5100

ttatggaggt tgctcgcatg atctcaggca cagaaaaacc taaaaaacgc tatgagcagg   5160

agttttctag cggacgggca cgtatcgaag cggcaagaaa agccactgcg gaagcaaaag   5220

cacttgccac gcttgaagca agcctgccga gcgccgctga agcgtctgga gagctgatcg   5280

acggcgtccg tgtcctctgg actgctccag ggcgtgccgc ccgtgatgag acggcttttc   5340

gccacgcttt gactgtggga taccagttaa aagcggctgg tgagcgccta aaagacacca   5400

agggtcatcg agcctacgag cgtgcctaca ccgtcgctca ggcggtcgga ggaggccgtg   5460

agcctgatct gccgccggac tgtgaccgcc agacggattg gccgcgacgt gtgcgcggct   5520

acgtcgctaa aggccagcca gtcgtccctg ctcgtcagac agagacgcag agccagccga   5580

ggcgaaaagc tctggccact atgggaagac gtggcggtaa aaaggccgca gaacgctgga   5640

aagacccaaa cagtgagtac gcccgagcac agcgagaaaa actagctaag tccagtcaac   5700

gacaagctag gaaagctaaa ggaaatcgct tgaccattgc aggttggttt atgactgttg   5760

agggagagac tggctcgtgg ccgacaatca atgaagctat gtctgaattt agcgtgtcac   5820

gtcagaccgt gaatagagca cttaaggtct gcgggcattg aacttccacg aggacgccga   5880
```

aagcttccca gtaaatgtgc catctcgtag gcagaaaacg gttcccccgt agggtctctc 5940
tcttggcctc ctttctaggt cgggctgatt gctcttgaag ctctctaggg gggctcacac 6000
cataggcaga taacgttccc caccggctcg cctcgtaagc gcacaaggac tgctcccaaa 6060
gatcttcaaa gccactgccg cgactgcctt cgcgaagcct tgccccgcgg aaatttcctc 6120
caccgagttc gtgcacaccc ctatgccaag cttctttcac cctaaattcg agagattgga 6180
ttcttaccgt ggaaattctt cgcaaaaatc gtcccctgat cgcccttgcg acgttggcgt 6240
cggtgccgct ggttgcgctt ggcttgaccg acttgatcag cggccgc 6287

<210> SEQ ID NO 38
<211> LENGTH: 30
<212> TYPE: DNA
<213> ORGANISM: Corynebacterium glutamicum

<400> SEQUENCE: 38
gagactcgag cggcttaaag tttggctgcc 30

<210> SEQ ID NO 39
<211> LENGTH: 32
<212> TYPE: DNA
<213> ORGANISM: Corynebacterium glutamicum

<400> SEQUENCE: 39
ctctcatatg caatccctcc atgagaaaaa tt 32

<210> SEQ ID NO 40
<211> LENGTH: 40
<212> TYPE: DNA
<213> ORGANISM: Corynebacterium glutamicum

<400> SEQUENCE: 40
ctctcatatg cgcggccgca atccctccat gagaaaaatt 40

<210> SEQ ID NO 41
<211> LENGTH: 39
<212> TYPE: DNA
<213> ORGANISM: Corynebacterium glutamicum

<400> SEQUENCE: 41
ctctcatatg caatctctcc atgagaaaaa ttttgtgtg 39

<210> SEQ ID NO 42
<211> LENGTH: 39
<212> TYPE: DNA
<213> ORGANISM: Corynebacterium glutamicum

<400> SEQUENCE: 42
ctctcatatg caatctcctc atgagaaaaa ttttgtgtg 39

<210> SEQ ID NO 43
<211> LENGTH: 39
<212> TYPE: DNA
<213> ORGANISM: Corynebacterium glutamicum

<400> SEQUENCE: 43
ctctcatatg caatcccttc atgagaaaaa ttttgtgtg 39

<210> SEQ ID NO 44
<211> LENGTH: 2961
<212> TYPE: DNA
<213> ORGANISM: Artificial Sequence
<220> FEATURE:

<223> OTHER INFORMATION: Description of Artificial Sequence: Synthetic
construct

<400> SEQUENCE: 44
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgcgtaata cgactcacta tagggcgaat tggagctcca 660
ccgcggtggc ggccgctcta gaactagtgg atcccccggg ctgcaggaat tcgatatcaa 720
gcttatcgat accgtcgacc tcgagggggg gcccggtacc cagcttttgt tccctttagt 780
gagggttaat tgcgcgcttg gcgtaatcat ggtcatagct gtttcctgtg tgaaattgtt 840
atccgctcac aattccacac aacatacgag ccggaagcat aaagtgtaaa gcctggggtg 900
cctaatgagt gagctaactc acattaattg cgttgcgctc actgcccgct ttccagtcgg 960
gaaacctgtc gtgccagctg cattaatgaa tcggccaacg cgcggggaga ggcggtttgc 1020
gtattgggcg ctcttccgct tcctcgctca ctgactcgct gcgctcggtc gttcggctgc 1080
ggcgagcggt atcagctcac tcaaaggcgg taatacggtt atccacagaa tcaggggata 1140
acgcaggaaa gaacatgtga gcaaaaggcc agcaaaaggc caggaaccgt aaaaaggccg 1200
cgttgctggc gtttttccat aggctccgcc cccctgacga gcatcacaaa aatcgacgct 1260
caagtcagag gtggcgaaac ccgacaggac tataaagata ccaggcgttt ccccctggaa 1320
gctccctcgt gcgctctcct gttccgaccc tgccgcttac cggatacctg tccgcctttc 1380
tcccttcggg aagcgtggcg ctttctcata gctcacgctg taggtatctc agttcggtgt 1440
aggtcgttcg ctccaagctg ggctgtgtgc acgaaccccc cgttcagccc gaccgctgcg 1500
ccttatccgg taactatcgt cttgagtcca acccggtaag acacgactta tcgccactgg 1560
cagcagccac tggtaacagg attagcagag cgaggtatgt aggcggtgct acagagttct 1620
tgaagtggtg gcctaactac ggctacacta gaaggacagt atttggtatc tgcgctctgc 1680
tgaagccagt taccttcgga aaaagagttg gtagctcttg atccggcaaa caaaccaccg 1740
ctggtagcgg tggttttttt gtttgcaagc agcagattac gcgcagaaaa aaaggatctc 1800
aagaagatcc tttgatcttt tctacggggt ctgacgctca gtggaacgaa aactcacgtt 1860
aagggatttt ggtcatgaga ttatcaaaaa ggatcttcac ctagatcctt ttaaattaaa 1920
aatgaagttt taaatcaatc taaagtatat atgagtaaac ttggtctgac agttaccaat 1980
gcttaatcag tgaggcacct atctcagcga tctgtctatt tcgttcatcc atagttgcct 2040
gactccccgt cgtgtagata actacgatac gggagggctt accatctggc cccagtgctg 2100
caatgatacc gcgagaccca cgctcaccgg ctccagattt atcagcaata aaccagccag 2160
ccggaagggc cgagcgcaga agtggtcctg caactttatc cgcctccatc cagtctatta 2220
attgttgccg ggaagctaga gtaagtagtt cgccagttaa tagtttgcgc aacgttgttg 2280

```
ccattgctac aggcatcgtg gtgtcacgct cgtcgtttgg tatggcttca ttcagctccg   2340

gttcccaacg atcaaggcga gttacatgat cccccatgtt gtgcaaaaaa gcggttagct   2400

ccttcggtcc tccgatcgtt gtcagaagta agttggccgc agtgttatca ctcatggtta   2460

tggcagcact gcataattct cttactgtca tgccatccgt aagatgcttt tctgtgactg   2520

gtgagtactc aaccaagtca ttctgagaat agtgtatgcg gcgaccgagt tgctcttgcc   2580

cggcgtcaat acgggataat accgcgccac atagcagaac tttaaaagtg ctcatcattg   2640

gaaaacgttc ttcggggcga aaactctcaa ggatcttacc gctgttgaga tccagttcga   2700

tgtaacccac tcgtgcaccc aactgatctt cagcatcttt tactttcacc agcgtttctg   2760

ggtgagcaaa aacaggaagg caaaatgccg caaaaaaggg aataagggcg acacggaaat   2820

gttgaatact catactcttc ctttttcaat attattgaag catttatcag ggttattgtc   2880

tcatgagcgg atacatattt gaatgtattt agaaaaataa acaaataggg gttccgcgca   2940

catttccccg aaaagtgcca c                                            2961


<210> SEQ ID NO 45
<211> LENGTH: 6431
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 45

aggcgaaaag ctctggccac tatgggaaga cgtggcggta aaaaggccgc agaacgctgg     60

aaagacccaa acagtgagta cgcccgagca cagcgagaaa aactagctaa gtccagtcaa    120

cgacaagcta ggaaagctaa aggaaatcgc ttgaccattg caggttggtt tatgactgtt    180

gagggagaga ctggctcgtg gccgacaatc aatgaagcta tgtctgaatt tagcgtgtca    240

cgtcagaccg tgaatagagc acttaaggtc tgcgggcatt gaacttccac gaggacgccg    300

aaagcttccc agtaaatgtg ccatctcgta ggcagaaaac ggttcccccg tagggtctct    360

ctcttggcct cctttctagg tcgggctgat tgctcttgaa gctctctagg ggggctcaca    420

ccataggcag ataacgttcc ccaccggctc gcctcgtaag cgcacaagga ctgctcccaa    480

agatcttcaa agccactgcc gcgactgcct tcgcgaagcc ttgccccgcg gaaatttcct    540

ccaccgagtt cgtgcacacc cctatgccaa gcttctttca ccctaaattc gagagattgg    600

attcttaccg tggaaattct tcgcaaaaat cgtcccctga tcgcccttgc gacgttggcg    660

tcggtgccgc tggttgcgct tggcttgacc gacttgatca gcggccgctc gatttaaatc    720

tcgagcggct taaagtttgg ctgccatgtg aatttttagc accctcaaca gttgagtgct    780

ggcactctcg gggtagagt gccaaatagg ttgtttgaca cacagttgtt cacccgcgac    840

gacggctgtg ctggaaaccc acaaccggca cacacaaaat ttttctcatg gagggattgc    900

atatgcccac cctcgcgcct tcaggtcaac ttgaaatcca agcgatcggt gatgtctcca    960

ccgaagccgg agcaatcatt acaaacgctg aaatcgccta tcaccgctgg ggtgaatacc   1020

gcgtagataa agaaggacgc agcaatgtcg ttctcatcga acacgccctc actggagatt   1080

ccaacgcagc cgattggtgg gctgacttgc tcggtcccgg caaagccatc aacactgata   1140

tttactgcgt gatctgtacc aacgtcatcg gtggttgcaa cggttccacc ggacctggct   1200

ccatgcatcc agatggaaat ttctggggta atcgcttccc cgccacgtcc attcgtgatc   1260

aggtaaacgc cgaaaaacaa ttcctcgacg cactcggcat caccacggtc gccgcagtac   1320
```

-continued

```
ttggtggttc catgggtggt gcccgcaccc tagagtgggc cgcaatgtac ccagaaactg   1380
ttggcgcagc tgctgttctt gcagtttctg cacgcgccag cgcctggcaa atcggcattc   1440
aatccgccca aattaaggcg attgaaaacg accaccactg gcacgaaggc aactactacg   1500
aatccggctg caacccagcc accggactcg gcgccgcccg acgcatcgcc cacctcacct   1560
accgtggcga actagaaatc gacgaacgct tcggcaccaa agcccaaaag aacgaaaacc   1620
cactcggtcc ctaccgcaag cccgaccagc gcttcgccgt ggaatcctac ttggactacc   1680
aagcagacaa gctagtacag cgtttcgacg ccggctccta cgtcttgctc accgacgccc   1740
tcaaccgcca cgacattggt cgcgaccgcg gaggcctcaa caaggcactc gaatccatca   1800
aagttccagt ccttgtcgca ggcgtagata ccgatatttt gtacccctac caccagcaag   1860
aacacctctc cagaaacctg ggaaatctac tggcaatggc aaaaatcgta tcccctgtcg   1920
gccacgatgc tttcctcacc gaaagccgcc aaatggatcg catcgtgagg aacttcttca   1980
gcctcatctc cccagacgaa gacaaccctt cgacctacat cgagttctac atctaaacta   2040
gttcggacct agggatatcg tcgacatcga tgctcttctg cgttaattaa caattgggat   2100
cctctagagt tctgtgaaaa acaccgtggg gcagtttctg cttcgcggtg tttttttattt   2160
gtggggcact agacccggga tttaaatcgc tagcgggctg ctaaaggaag cggaacacgt   2220
agaaagccag tccgcagaaa cggtgctgac cccggatgaa tgtcagctac tgggctatct   2280
ggacaaggga aaacgcaagc gcaaagagaa agcaggtagc ttgcagtggg cttacatggc   2340
gatagctaga ctgggcggtt ttatggacag caagcgaacc ggaattgcca gctggggcgc   2400
cctctggtaa ggttgggaag ccctgcaaag taaactggat ggctttcttg ccgccaagga   2460
tctgatggcg caggggatca agatctgatc aagagacagg atgaggatcg tttcgcatga   2520
ttgaacaaga tggattgcac gcaggttctc cggccgcttg ggtggagagg ctattcggct   2580
atgactgggc acaacagaca atcggctgct ctgatgccgc cgtgttccgg ctgtcagcgc   2640
aggggcgccc ggttcttttt gtcaagaccg acctgtccgg tgccctgaat gaactgcagg   2700
acgaggcagc gcggctatcg tggctggcca cgacgggcgt tccttgcgca gctgtgctcg   2760
acgttgtcac tgaagcggga agggactggc tgctattggg cgaagtgccg gggcaggatc   2820
tcctgtcatc tcaccttgct cctgccgaga aagtatccat catggctgat gcaatgcggc   2880
ggctgcatac gcttgatccg gctacctgcc cattcgacca ccaagcgaaa catcgcatcg   2940
agcgagcacg tactcggatg gaagccggtc ttgtcgatca ggatgatctg gacgaagagc   3000
atcaggggct cgcgccagcc gaactgttcg ccaggctcaa ggcgcgcatg cccgacggcg   3060
aggatctcgt cgtgacccat ggcgatgcct gcttgccgaa tatcatggtg gaaaatggcc   3120
gcttttctgg attcatcgac tgtggccggc tgggtgtggc ggaccgctat caggacatag   3180
cgttggctac ccgtgatatt gctgaagagc ttggcggcga atgggctgac cgcttcctcg   3240
tgctttacgg tatcgccgct cccgattcgc agcgcatcgc cttctatcgc cttcttgacg   3300
agttcttctg agcgggactc tggggttcga aatgaccgac caagcgacgc ccaacctgcc   3360
atcacgagat ttcgattcca ccgccgcctt ctatgaaagg ttgggcttcg gaatcgtttt   3420
ccgggacgcc ggctggatga tcctccagcg cggggatctc atgctggagt tcttcgccca   3480
cgctagcggc gcgccggccg gcccggtgtg aaataccgca cagatgcgta aggagaaaat   3540
accgcatcag gcgctcttcc gcttcctcgc tcactgactc gctgcgctcg gtcgttcggc   3600
tgcggcgagc ggtatcagct cactcaaagg cggtaatacg gttatccaca gaatcagggg   3660
ataacgcagg aaagaacatg tgagcaaaag gccagcaaaa ggccaggaac cgtaaaaagg   3720
```

-continued

```
ccgcgttgct ggcgtttttc cataggctcc gcccccctga cgagcatcac aaaaatcgac   3780
gctcaagtca gaggtggcga aacccgacag gactataaag ataccaggcg tttccccctg   3840
gaagctccct cgtgcgctct cctgttccga ccctgccgct taccggatac ctgtccgcct   3900
ttctcccttc gggaagcgtg gcgctttctc atagctcacg ctgtaggtat ctcagttcgg   3960
tgtaggtcgt tcgctccaag ctgggctgtg tgcacgaacc ccccgttcag cccgaccgct   4020
gcgccttatc cggtaactat cgtcttgagt ccaacccggt aagacacgac ttatcgccac   4080
tggcagcagc cactggtaac aggattagca gagcgaggta tgtaggcggt gctacagagt   4140
tcttgaagtg gtggcctaac tacggctaca ctagaaggac agtatttggt atctgcgctc   4200
tgctgaagcc agttaccttc ggaaaaagag ttggtagctc ttgatccggc aaacaaacca   4260
ccgctggtag cggtggtttt tttgtttgca agcagcagat tacgcgcaga aaaaaaggat   4320
ctcaagaaga tcctttgatc ttttctacgg ggtctgacgc tcagtggaac gaaaactcac   4380
gttaagggat tttggtcatg agattatcaa aaaggatctt cacctagatc cttttaaagg   4440
ccggccgcgg ccgcgcaaag tcccgcttcg tgaaaatttt cgtgccgcgt gattttccgc   4500
caaaaacttt aacgaacgtt cgttataatg gtgtcatgac cttcacgacg aagtactaaa   4560
attggcccga atcatcagct atggatctct ctgatgtcgc gctggagtcc gacgcgctcg   4620
atgctgccgt cgatttaaaa acggtgatcg gatttttccg agctctcgat acgacggacg   4680
cgccagcatc acgagactgg gccagtgccg cgagcgacct agaaactctc gtggcggatc   4740
ttgaggagct ggctgacgag ctgcgtgctc ggccagcgcc aggaggacgc acagtagtgg   4800
aggatgcaat cagttgcgcc tactgcggtg gcctgattcc tccccggcct gacccgcgag   4860
gacggcgcgc aaaatattgc tcagatgcgt gtcgtgccgc agccagccgc gagcgcgcca   4920
acaaacgcca cgccgaggag ctggaggcgg ctaggtcgca aatggcgctg gaagtgcgtc   4980
ccccgagcga aattttggcc atggtcgtca cagagctgga agcggcagcg agaattatcg   5040
cgatcgtggc ggtgcccgca ggcatgacaa acatcgtaaa tgccgcgttt cgtgtgccgt   5100
ggccgcccag gacgtgtcag cgccgccacc acctgcaccg aatcggcagc agcgtcgcgc   5160
gtcgaaaaag cgcacaggcg gcaagaagcg ataagctgca cgaatacctg aaaaatgttg   5220
aacgccccgt gagcggtaac tcacagggcg tcggctaacc cccagtccaa acctgggaga   5280
aagcgctcaa aaatgactct agcggattca cgagacattg acacaccggc ctggaaattt   5340
tccgctgatc tgttcgacac ccatcccgag ctcgcgctgc gatcacgtgg ctggacgagc   5400
gaagaccgcc gcgaattcct cgctcacctg ggcagagaaa atttccaggg cagcaagacc   5460
cgcgacttcg ccagcgcttg gatcaaagac ccggacacgg agaaacacag ccgaagttat   5520
accgagttgg ttcaaaatcg cttgcccggt gccagtatgt tgctctgacg cacgcgcagc   5580
acgcagccgt gcttgtcctg gacattgatg tgccgagcca ccaggccggc gggaaaatcg   5640
agcacgtaaa ccccgaggtc tacgcgattt tggagcgctg ggcacgcctg gaaaaagcgc   5700
cagcttggat cggcgtgaat ccactgagcg ggaaatgcca gctcatctgg ctcattgatc   5760
cggtgtatgc cgcagcaggc atgagcagcc cgaatatgcg cctgctggct gcaacgaccg   5820
aggaaatgac ccgcgttttc ggcgctgacc aggctttttc acataggctg agccgtggcc   5880
actgcactct ccgacgatcc cagccgtacc gctggcatgc ccagcacaat cgcgtggatc   5940
gcctagctga tcttatggag gttgctcgca tgatctcagg cacagaaaaa cctaaaaaac   6000
gctatgagca ggagttttct agcggacggg cacgtatcga agcggcaaga aaagccactg   6060
cggaagcaaa agcacttgcc acgcttgaag caagcctgcc gagcgccgct gaagcgtctg   6120
```

```
gagagctgat cgacggcgtc cgtgtcctct ggactgctcc agggcgtgcc gcccgtgatg   6180

agacggcttt tcgccacgct ttgactgtgg gataccagtt aaaagcggct ggtgagcgcc   6240

taaaagacac caagggtcat cgagcctacg agcgtgccta caccgtcgct caggcggtcg   6300

gaggaggccg tgagcctgat ctgccgccgg actgtgaccg ccagacggat tggccgcgac   6360

gtgtgcgcgg ctacgtcgct aaaggccagc cagtcgtccc tgctcgtcag acagagacgc   6420

agagccagcc g                                                        6431
```

```
<210> SEQ ID NO 46
<211> LENGTH: 6439
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 46

aaatctcgag cggcttaaag tttggctgcc atgtgaattt ttagcaccct caacagttga     60

gtgctggcac tctcgggggt agagtgccaa ataggttgtt tgacacacag ttgttcaccc    120

gcgacgacgg ctgtgctgga aacccacaac cggcacacac aaaatttttc tcatggaggg    180

attgcggccg cgcatatgcc caccctcgcg ccttcaggtc aacttgaaat ccaagcgatc    240

ggtgatgtct ccaccgaagc cggagcaatc attacaaacg ctgaaatcgc ctatcaccgc    300

tggggtgaat accgcgtaga taaagaagga cgcagcaatg tcgttctcat cgaacacgcc    360

ctcactggag attccaacgc agccgattgg tgggctgact tgctcggtcc cggcaaagcc    420

atcaacactg atatttactg cgtgatctgt accaacgtca tcggtggttg caacggttcc    480

accggacctg gctccatgca tccagatgga aatttctggg gtaatcgctt ccccgccacg    540

tccattcgtg atcaggtaaa cgccgaaaaa caattcctcg acgcactcgg catcaccacg    600

gtcgccgcag tacttggtgg ttccatgggt ggtgcccgca ccctagagtg ggccgcaatg    660

tacccagaaa ctgttggcgc agctgctgtt cttgcagttt ctgcacgcgc cagcgcctgg    720

caaatcggca ttcaatccgc ccaaattaag gcgattgaaa acgaccacca ctggcacgaa    780

ggcaactact acgaatccgg ctgcaaccca gccaccggac tcggcgccgc ccgacgcatc    840

gcccacctca cctaccgtgg cgaactagaa atcgacgaac gcttcggcac caaagcccaa    900

aagaacgaaa acccactcgg tccctaccgc aagcccgacc agcgcttcgc cgtggaatcc    960

tacttggact accaagcaga caagctagta cagcgtttcg acgccggctc ctacgtcttg   1020

ctcaccgacg ccctcaaccg ccacgacatt ggtcgcgacc gcggaggcct caacaaggca   1080

ctcgaatcca tcaaagttcc agtccttgtc gcaggcgtag ataccgatat tttgtacccc   1140

taccaccagc aagaacacct ctccagaaac ctgggaaatc tactggcaat ggcaaaaatc   1200

gtatcccctg tcggccacga tgctttcctc accgaaagcc gccaaatgga tcgcatcgtg   1260

aggaacttct tcagcctcat ctccccagac gaagacaacc cttcgaccta catcgagttc   1320

tacatctaaa ctagttcgga cctagggata tcgtcgacat cgatgctctt ctgcgttaat   1380

taacaattgg gatcctctag agttctgtga aaaacaccgt ggggcagttt ctgcttcgcg   1440

gtgtttttta tttgtggggc actagacccg ggatttaaat cgctagcggg ctgctaaagg   1500

aagcggaaca cgtagaaagc cagtccgcag aaacggtgct gaccccggat gaatgtcagc   1560

tactgggcta tctggacaag ggaaaacgca agcgcaaaga gaaagcaggt agcttgcagt   1620

gggcttacat ggcgatagct agactgggcg gttttatgga cagcaagcga accggaattg   1680

ccagctgggg cgccctctgg taaggttggg aagccctgca aagtaaactg gatggctttc   1740
```

```
ttgccgccaa ggatctgatg gcgcagggga tcaagatctg atcaagagac aggatgagga   1800
tcgtttcgca tgattgaaca agatggattg cacgcaggtt ctccggccgc ttgggtggag   1860
aggctattcg gctatgactg ggcacaacag acaatcggct gctctgatgc cgccgtgttc   1920
cggctgtcag cgcaggggcg cccggttctt tttgtcaaga ccgacctgtc cggtgccctg   1980
aatgaactgc aggacgaggc agcgcggcta tcgtggctgg ccacgacggg cgttccttgc   2040
gcagctgtgc tcgacgttgt cactgaagcg ggaagggact ggctgctatt gggcgaagtg   2100
ccggggcagg atctcctgtc atctcacctt gctcctgccg agaaagtatc catcatggct   2160
gatgcaatgc ggcggctgca tacgcttgat ccggctacct gcccattcga ccaccaagcg   2220
aaacatcgca tcgagcgagc acgtactcgg atggaagccg gtcttgtcga tcaggatgat   2280
ctggacgaag agcatcaggg gctcgcgcca gccgaactgt tcgccaggct caaggcgcgc   2340
atgcccgacg gcgaggatct cgtcgtgacc catggcgatg cctgcttgcc gaatatcatg   2400
gtggaaaatg gccgcttttc tggattcatc gactgtggcc ggctgggtgt ggcggaccgc   2460
tatcaggaca tagcgttggc tacccgtgat attgctgaag agcttggcgg cgaatgggct   2520
gaccgcttcc tcgtgcttta cggtatcgcc gctcccgatt cgcagcgcat cgccttctat   2580
cgccttcttg acgagttctt ctgagcggga ctctggggtt cgaaatgacc gaccaagcga   2640
cgcccaacct gccatcacga gatttcgatt ccaccgccgc cttctatgaa aggttgggct   2700
tcggaatcgt tttccgggac gccggctgga tgatcctcca gcgcggggat ctcatgctgg   2760
agttcttcgc ccacgctagc ggcgcgccgg ccggcccggt gtgaaatacc gcacagatgc   2820
gtaaggagaa aataccgcat caggcgctct tccgcttcct cgctcactga ctcgctgcgc   2880
tcggtcgttc ggctgcggcg agcggtatca gctcactcaa aggcggtaat acggttatcc   2940
acagaatcag gggataacgc aggaaagaac atgtgagcaa aaggccagca aaaggccagg   3000
aaccgtaaaa aggccgcgtt gctggcgttt ttccataggc tccgcccccc tgacgagcat   3060
cacaaaaatc gacgctcaag tcagaggtgg cgaaacccga caggactata aagataccag   3120
gcgtttcccc ctggaagctc cctcgtgcgc tctcctgttc cgaccctgcc gcttaccgga   3180
tacctgtccg cctttctccc ttcgggaagc gtggcgcttt ctcatagctc acgctgtagg   3240
tatctcagtt cggtgtaggt cgttcgctcc aagctgggct gtgtgcacga accccccgtt   3300
cagcccgacc gctgcgcctt atccggtaac tatcgtcttg agtccaaccc ggtaagacac   3360
gacttatcgc cactggcagc agccactggt aacaggatta gcagagcgag gtatgtaggc   3420
ggtgctacag agttcttgaa gtggtggcct aactacggct acactagaag gacagtattt   3480
ggtatctgcg ctctgctgaa gccagttacc ttcggaaaaa gagttggtag ctcttgatcc   3540
ggcaaacaaa ccaccgctgg tagcggtggt ttttttgttt gcaagcagca gattacgcgc   3600
agaaaaaaag gatctcaaga agatcctttg atcttttcta cggggtctga cgctcagtgg   3660
aacgaaaact cacgttaagg gattttggtc atgagattat caaaaaggat cttcacctag   3720
atccttttaa aggccggccg cggccgcgca aagtcccgct tcgtgaaaat tttcgtgccg   3780
cgtgattttc cgccaaaaac tttaacgaac gttcgttata atggtgtcat gaccttcacg   3840
acgaagtact aaaattggcc cgaatcatca gctatggatc tctctgatgt cgcgctggag   3900
tccgacgcgc tcgatgctgc cgtcgattta aaaacggtga tcggattttt ccgagctctc   3960
gatacgacgg acgcgccagc atcacgagac tgggccagtg ccgcgagcga cctagaaact   4020
ctcgtggcgg atcttgagga gctggctgac gagctgcgtg ctcggccagc gccaggagga   4080
cgcacagtag tggaggatgc aatcagttgc gcctactgcg gtggcctgat tcctccccgg   4140
```

```
cctgacccgc gaggacggcg cgcaaaatat tgctcagatg cgtgtcgtgc cgcagccagc   4200
cgcgagcgcg ccaacaaacg ccacgccgag gagctggagg cggctaggtc gcaaatggcg   4260
ctggaagtgc gtcccccgag cgaaattttg gccatggtcg tcacagagct ggaagcggca   4320
gcgagaatta tcgcgatcgt ggcggtgccc gcaggcatga caaacatcgt aaatgccgcg   4380
tttcgtgtgc cgtggccgcc caggacgtgt cagcgccgcc accacctgca ccgaatcggc   4440
agcagcgtcg cgcgtcgaaa aagcgcacag gcggcaagaa gcgataagct gcacgaatac   4500
ctgaaaaatg ttgaacgccc cgtgagcggt aactcacagg gcgtcggcta acccccagtc   4560
caaacctggg agaaagcgct caaaaatgac tctagcggat tcacgagaca ttgacacacc   4620
ggcctggaaa ttttccgctg atctgttcga cacccatccc gagctcgcgc tgcgatcacg   4680
tggctggacg agcgaagacc gccgcgaatt cctcgctcac ctgggcagag aaaatttcca   4740
gggcagcaag acccgcgact tcgccagcgc ttggatcaaa gacccggaca cggagaaaca   4800
cagccgaagt tataccgagt tggttcaaaa tcgcttgccc ggtgccagta tgttgctctg   4860
acgcacgcgc agcacgcagc cgtgcttgtc ctggacattg atgtgccgag ccaccaggcc   4920
ggcgggaaaa tcgagcacgt aaaccccgag gtctacgcga ttttggagcg ctgggcacgc   4980
ctggaaaaag cgccagcttg gatcggcgtg aatccactga gcgggaaatg ccagctcatc   5040
tggctcattg atccggtgta tgccgcagca ggcatgagca gcccgaatat gcgcctgctg   5100
gctgcaacga ccgaggaaat gacccgcgtt ttcggcgctg accaggcttt ttcacatagg   5160
ctgagccgtg gccactgcac tctccgacga tcccagccgt accgctggca tgcccagcac   5220
aatcgcgtgg atcgcctagc tgatcttatg gaggttgctc gcatgatctc aggcacagaa   5280
aaacctaaaa aacgctatga gcaggagttt tctagcggac gggcacgtat cgaagcggca   5340
agaaaagcca ctgcggaagc aaaagcactt gccacgcttg aagcaagcct gccgagcgcc   5400
gctgaagcgt ctggagagct gatcgacggc gtccgtgtcc tctggactgc tccagggcgt   5460
gccgcccgtg atgagacggc ttttcgccac gctttgactg tgggatacca gttaaaagcg   5520
gctggtgagc gcctaaaaga caccaagggt catcgagcct acgagcgtgc ctacaccgtc   5580
gctcaggcgg tcggaggagg ccgtgagcct gatctgccgc cggactgtga ccgccagacg   5640
gattggccgc gacgtgtgcg cggctacgtc gctaaaggcc agccagtcgt ccctgctcgt   5700
cagacagaga cgcagagcca gccgaggcga aaagctctgg ccactatggg aagacgtggc   5760
ggtaaaaagg ccgcagaacg ctggaaagac ccaaacagtg agtacgcccg agcacagcga   5820
gaaaaactag ctaagtccag tcaacgacaa gctaggaaag ctaaaggaaa tcgcttgacc   5880
attgcaggtt ggtttatgac tgttgaggga gagactggct cgtggccgac aatcaatgaa   5940
gctatgtctg aatttagcgt gtcacgtcag accgtgaata gagcacttaa ggtctgcggg   6000
cattgaactt ccacgaggac gccgaaagct tcccagtaaa tgtgccatct cgtaggcaga   6060
aaacggttcc cccgtagggt ctctctcttg gcctcctttc taggtcgggc tgattgctct   6120
tgaagctctc taggggggct cacaccatag gcagataacg ttccccaccg gctcgcctcg   6180
taagcgcaca aggactgctc ccaaagatct tcaaagccac tgccgcgact gccttcgcga   6240
agccttgccc cgcggaaatt tcctccaccg agttcgtgca cacccctatg ccaagcttct   6300
ttcaccctaa attcgagaga ttggattctt accgtggaaa ttcttcgcaa aaatcgtccc   6360
ctgatcgccc ttgcgacgtt ggcgtcggtg ccgctggttg cgcttggctt gaccgacttg   6420
atcagcggcc gctcgatttt                                                6439
```

<210> SEQ ID NO 47
<211> LENGTH: 6431
<212> TYPE: DNA
<213> ORGANISM: Artificial Sequence
<220> FEATURE:
<223> OTHER INFORMATION: Description of Artificial Sequence: Synthetic construct

<400> SEQUENCE: 47
aggcgaaaag ctctggccac tatgggaaga cgtggcggta aaaaggccgc agaacgctgg 60
aaagacccaa acagtgagta cgcccgagca cagcgagaaa aactagctaa gtccagtcaa 120
cgacaagcta ggaaagctaa aggaaatcgc ttgaccattg caggttggtt tatgactgtt 180
gagggagaga ctggctcgtg gccgacaatc aatgaagcta tgtctgaatt tagcgtgtca 240
cgtcagaccg tgaatagagc acttaaggtc tgcgggcatt gaacttccac gaggacgccg 300
aaagcttccc agtaaatgtg ccatctcgta ggcagaaaac ggttcccccg tagggtctct 360
ctcttggcct cctttctagg tcgggctgat tgctcttgaa gctctctagg ggggctcaca 420
ccataggcag ataacgttcc ccaccggctc gcctcgtaag cgcacaagga ctgctcccaa 480
agatcttcaa agccactgcc gcgactgcct tcgcgaagcc ttgccccgcg gaaatttcct 540
ccaccgagtt cgtgcacacc cctatgccaa gcttctttca ccctaaattc gagagattgg 600
attcttaccg tggaaattct tcgcaaaaat cgtcccctga tcgcccttgc gacgttggcg 660
tcggtgccgc tggttgcgct tggcttgacc gacttgatca gcggccgctc gatttaaatc 720
tcgagcggct taaagtttgg ctgccatgtg aatttttagc accctcaaca gttgagtgct 780
ggcactctcg gggtagagt gccaaatagg ttgtttgaca cacagttgtt cacccgcgac 840
gacggctgtg ctggaaaccc acaaccggca cacacaaaat tttctcatgg gagagattgc 900
atatgcccac cctcgcgcct tcaggtcaac ttgaaatcca agcgatcggt gatgtctcca 960
ccgaagccgg agcaatcatt acaaacgctg aaatcgccta tcaccgctgg ggtgaatacc 1020
gcgtagataa agaaggacgc agcaatgtcg ttctcatcga acacgccctc actggagatt 1080
ccaacgcagc cgattggtgg gctgacttgc tcggtcccgg caaagccatc aacactgata 1140
tttactgcgt gatctgtacc aacgtcatcg gtggttgcaa cggttccacc ggacctggct 1200
ccatgcatcc agatggaaat ttctggggta atcgcttccc cgccacgtcc attcgtgatc 1260
aggtaaacgc cgaaaaacaa ttcctcgacg cactcggcat caccacggtc gccgcagtac 1320
ttggtggttc catgggtggt gcccgcaccc tagagtgggc cgcaatgtac ccagaaactg 1380
ttggcgcagc tgctgttctt gcagtttctg cacgcgccag cgcctggcaa atcggcattc 1440
aatccgccca aattaaggcg attgaaaacg accaccactg gcacgaaggc aactactacg 1500
aatccggctg caacccagcc accggactcg gcgccgcccg acgcatcgcc cacctcacct 1560
accgtggcga actagaaatc gacgaacgct tcggcaccaa agcccaaaag aacgaaaacc 1620
cactcggtcc ctaccgcaag cccgaccagc gcttcgccgt ggaatcctac ttggactacc 1680
aagcagacaa gctagtacag cgtttcgacg ccggctccta cgtcttgctc accgacgccc 1740
tcaaccgcca cgacattggt cgcgaccgcg gaggcctcaa caaggcactc gaatccatca 1800
aagttccagt ccttgtcgca ggcgtagata ccgatatttt gtacccctac caccagcaag 1860
aacacctctc cagaaacctg ggaaatctac tggcaatggc aaaaatcgta tcccctgtcg 1920
gccacgatgc tttcctcacc gaaagccgcc aaatggatcg catcgtgagg aacttcttca 1980
gcctcatctc cccagacgaa gacaaccctt cgacctacat cgagttctac atctaaacta 2040
gttcggacct agggatatcg tcgacatcga tgctcttctg cgttaattaa caattgggat 2100

-continued

```
cctctagagt tctgtgaaaa acaccgtggg gcagtttctg cttcgcggtg tttttttattt   2160
gtggggcact agacccggga tttaaatcgc tagcgggctg ctaaaggaag cggaacacgt   2220
agaaagccag tccgcagaaa cggtgctgac cccggatgaa tgtcagctac tgggctatct   2280
ggacaaggga aaacgcaagc gcaaagagaa agcaggtagc ttgcagtggg cttacatggc   2340
gatagctaga ctgggcggtt ttatggacag caagcgaacc ggaattgcca gctggggcgc   2400
cctctggtaa ggttgggaag ccctgcaaag taaactggat ggctttcttg ccgccaagga   2460
tctgatggcg caggggatca agatctgatc aagagacagg atgaggatcg tttcgcatga   2520
ttgaacaaga tggattgcac gcaggttctc cggccgcttg ggtggagagg ctattcggct   2580
atgactgggc acaacagaca atcggctgct ctgatgccgc cgtgttccgg ctgtcagcgc   2640
aggggcgccc ggttcttttt gtcaagaccg acctgtccgg tgccctgaat gaactgcagg   2700
acgaggcagc gcggctatcg tggctggcca cgacgggcgt tccttgcgca gctgtgctcg   2760
acgttgtcac tgaagcggga agggactggc tgctattggg cgaagtgccg gggcaggatc   2820
tcctgtcatc tcaccttgct cctgccgaga aagtatccat catggctgat gcaatgcggc   2880
ggctgcatac gcttgatccg gctacctgcc cattcgacca ccaagcgaaa catcgcatcg   2940
agcgagcacg tactcggatg gaagccggtc ttgtcgatca ggatgatctg gacgaagagc   3000
atcaggggct cgcgccagcc gaactgttcg ccaggctcaa ggcgcgcatg cccgacggcg   3060
aggatctcgt cgtgacccat ggcgatgcct gcttgccgaa tatcatggtg gaaaatggcc   3120
gcttttctgg attcatcgac tgtggccggc tgggtgtggc ggaccgctat caggacatag   3180
cgttggctac ccgtgatatt gctgaagagc ttggcggcga atgggctgac cgcttcctcg   3240
tgctttacgg tatcgccgct cccgattcgc agcgcatcgc cttctatcgc cttcttgacg   3300
agttcttctg agcgggactc tggggttcga aatgaccgac caagcgacgc ccaacctgcc   3360
atcacgagat ttcgattcca ccgccgcctt ctatgaaagg ttgggcttcg gaatcgtttt   3420
ccgggacgcc ggctggatga tcctccagcg cggggatctc atgctggagt tcttcgccca   3480
cgctagcggc gcgccggccg gcccggtgtg aaataccgca cagatgcgta aggagaaaat   3540
accgcatcag gcgctcttcc gcttcctcgc tcactgactc gctgcgctcg gtcgttcggc   3600
tgcggcgagc ggtatcagct cactcaaagg cggtaatacg gttatccaca gaatcagggg   3660
ataacgcagg aaagaacatg tgagcaaaag gccagcaaaa ggccaggaac cgtaaaaagg   3720
ccgcgttgct ggcgtttttc cataggctcc gcccccctga cgagcatcac aaaaatcgac   3780
gctcaagtca gaggtggcga aacccgacag gactataaag ataccaggcg tttccccctg   3840
gaagctccct cgtgcgctct cctgttccga ccctgccgct taccggatac ctgtccgcct   3900
ttctcccttc gggaagcgtg gcgctttctc atagctcacg ctgtaggtat ctcagttcgg   3960
tgtaggtcgt tcgctccaag ctgggctgtg tgcacgaacc ccccgttcag cccgaccgct   4020
gcgccttatc cggtaactat cgtcttgagt ccaacccggt aagacacgac ttatcgccac   4080
tggcagcagc cactggtaac aggattagca gagcgaggta tgtaggcggt gctacagagt   4140
tcttgaagtg gtggcctaac tacggctaca ctagaaggac agtatttggt atctgcgctc   4200
tgctgaagcc agttaccttc ggaaaaagag ttggtagctc ttgatccggc aaacaaacca   4260
ccgctggtag cggtggtttt tttgtttgca agcagcagat tacgcgcaga aaaaaaggat   4320
ctcaagaaga tcctttgatc ttttctacgg ggtctgacgc tcagtggaac gaaaactcac   4380
gttaagggat tttggtcatg agattatcaa aaaggatctt cacctagatc cttttaaagg   4440
ccggccgcgg ccgcgcaaag tcccgcttcg tgaaaatttt cgtgccgcgt gattttccgc   4500
```

-continued

```
caaaaacttt aacgaacgtt cgttataatg gtgtcatgac cttcacgacg aagtactaaa   4560

attggcccga atcatcagct atggatctct ctgatgtcgc gctggagtcc gacgcgctcg   4620

atgctgccgt cgatttaaaa acggtgatcg gatttttccg agctctcgat acgacggacg   4680

cgccagcatc acgagactgg gccagtgccg cgagcgacct agaaactctc gtggcggatc   4740

ttgaggagct ggctgacgag ctgcgtgctc ggccagcgcc aggaggacgc acagtagtgg   4800

aggatgcaat cagttgcgcc tactgcggtg gcctgattcc tccccggcct gacccgcgag   4860

gacggcgcgc aaaatattgc tcagatgcgt gtcgtgccgc agccagccgc gagcgcgcca   4920

acaaacgcca cgccgaggag ctggaggcgg ctaggtcgca aatggcgctg gaagtgcgtc   4980

ccccgagcga aattttggcc atggtcgtca cagagctgga agcggcagcg agaattatcg   5040

cgatcgtggc ggtgcccgca ggcatgacaa acatcgtaaa tgccgcgttt cgtgtgccgt   5100

ggccgcccag gacgtgtcag cgccgccacc acctgcaccg aatcggcagc agcgtcgcgc   5160

gtcgaaaaag cgcacaggcg gcaagaagcg ataagctgca cgaatacctg aaaaatgttg   5220

aacgccccgt gagcggtaac tcacagggcg tcggctaacc cccagtccaa acctgggaga   5280

aagcgctcaa aaatgactct agcggattca cgagacattg acacaccggc ctggaaattt   5340

tccgctgatc tgttcgacac ccatcccgag ctcgcgctgc gatcacgtgg ctggacgagc   5400

gaagaccgcc gcgaattcct cgctcacctg ggcagagaaa atttccaggg cagcaagacc   5460

cgcgacttcg ccagcgcttg gatcaaagac ccggacacgg agaaacacag ccgaagttat   5520

accgagttgg ttcaaaatcg cttgcccggt gccagtatgt tgctctgacg cacgcgcagc   5580

acgcagccgt gcttgtcctg gacattgatg tgccgagcca ccaggccggc gggaaaatcg   5640

agcacgtaaa ccccgaggtc tacgcgattt tggagcgctg ggcacgcctg gaaaaagcgc   5700

cagcttggat cggcgtgaat ccactgagcg ggaaatgcca gctcatctgg ctcattgatc   5760

cggtgtatgc cgcagcaggc atgagcagcc cgaatatgcg cctgctggct gcaacgaccg   5820

aggaaatgac ccgcgttttc ggcgctgacc aggctttttc acataggctg agccgtggcc   5880

actgcactct ccgacgatcc cagccgtacc gctggcatgc ccagcacaat cgcgtggatc   5940

gcctagctga tcttatggag gttgctcgca tgatctcagg cacagaaaaa cctaaaaaac   6000

gctatgagca ggagttttct agcggacggg cacgtatcga agcggcaaga aaagccactg   6060

cggaagcaaa agcacttgcc acgcttgaag caagcctgcc gagcgccgct gaagcgtctg   6120

gagagctgat cgacggcgtc cgtgtcctct ggactgctcc agggcgtgcc gcccgtgatg   6180

agacggcttt tcgccacgct ttgactgtgg gataccagtt aaaagcggct ggtgagcgcc   6240

taaaagacac caagggtcat cgagcctacg agcgtgccta caccgtcgct caggcggtcg   6300

gaggaggccg tgagcctgat ctgccgccgg actgtgaccg ccagacggat tggccgcgac   6360

gtgtgcgcgg ctacgtcgct aaaggccagc cagtcgtccc tgctcgtcag acagagacgc   6420

agagccagcc g                                                        6431
```

<210> SEQ ID NO 48
<211> LENGTH: 6431
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 48

```
aggcgaaaag ctctggccac tatgggaaga cgtggcggta aaaaggccgc agaacgctgg     60

aaagacccaa acagtgagta cgcccgagca cagcgagaaa aactagctaa gtccagtcaa    120
```

```
cgacaagcta ggaaagctaa aggaaatcgc ttgaccattg caggttggtt tatgactgtt    180
gagggagaga ctggctcgtg gccgacaatc aatgaagcta tgtctgaatt tagcgtgtca    240
cgtcagaccg tgaatagagc acttaaggtc tgcgggcatt gaacttccac gaggacgccg    300
aaagcttccc agtaaatgtg ccatctcgta ggcagaaaac ggttcccccg tagggtctct    360
ctcttggcct cctttctagg tcgggctgat tgctcttgaa gctctctagg ggggctcaca    420
ccataggcag ataacgttcc ccaccggctc gcctcgtaag cgcacaagga ctgctcccaa    480
agatcttcaa agccactgcc gcgactgcct tcgcgaagcc ttgccccgcg gaaatttcct    540
ccaccgagtt cgtgcacacc cctatgccaa gcttctttca ccctaaattc gagagattgg    600
attcttaccg tggaaattct tcgcaaaaat cgtcccctga tcgcccttgc gacgttggcg    660
tcggtgccgc tggttgcgct tggcttgacc gacttgatca gcggccgctc gatttaaatc    720
tcgagcggct taaagtttgg ctgccatgtg aatttttagc accctcaaca gttgagtgct    780
ggcactctcg gggtagagt gccaaatagg ttgtttgaca cacagttgtt cacccgcgac    840
gacggctgtg ctggaaaccc acaaccggca cacacaaaat ttttctcatg aggagattgc    900
atatgcccac cctcgcgcct tcaggtcaac ttgaaatcca agcgatcggt gatgtctcca    960
ccgaagccgg agcaatcatt acaaacgctg aaatcgccta tcaccgctgg ggtgaatacc   1020
gcgtagataa agaaggacgc agcaatgtcg ttctcatcga acacgccctc actggagatt   1080
ccaacgcagc cgattggtgg gctgacttgc tcggtcccgg caaagccatc aacactgata   1140
tttactgcgt gatctgtacc aacgtcatcg gtggttgcaa cggttccacc ggacctggct   1200
ccatgcatcc agatggaaat ttctggggta atcgcttccc cgccacgtcc attcgtgatc   1260
aggtaaacgc cgaaaaacaa ttcctcgacg cactcggcat caccacggtc gccgcagtac   1320
ttggtggttc catgggtggt gcccgcaccc tagagtgggc cgcaatgtac ccagaaactg   1380
ttggcgcagc tgctgttctt gcagtttctg cacgcgccag cgcctggcaa atcggcattc   1440
aatccgccca aattaaggcg attgaaaacg accaccactg gcacgaaggc aactactacg   1500
aatccggctg caacccagcc accggactcg gcgccgcccg acgcatcgcc cacctcacct   1560
accgtggcga actagaaatc gacgaacgct tcggcaccaa agcccaaaag aacgaaaacc   1620
cactcggtcc ctaccgcaag cccgaccagc gcttcgccgt ggaatcctac ttggactacc   1680
aagcagacaa gctagtacag cgtttcgacg ccggctccta cgtcttgctc accgacgccc   1740
tcaaccgcca cgacattggt cgcgaccgcg gaggcctcaa caaggcactc gaatccatca   1800
aagttccagt ccttgtcgca ggcgtagata ccgatatttt gtacccctac caccagcaag   1860
aacacctctc cagaaacctg ggaaatctac tggcaatggc aaaaatcgta tcccctgtcg   1920
gccacgatgc tttcctcacc gaaagccgcc aaatggatcg catcgtgagg aacttcttca   1980
gcctcatctc cccagacgaa gacaaccctt cgacctacat cgagttctac atctaaacta   2040
gttcggacct agggatatcg tcgacatcga tgctcttctg cgttaattaa caattgggat   2100
cctctagagt tctgtgaaaa acaccgtggg gcagtttctg cttcgcggtg tttttttattt   2160
gtggggcact agacccggga tttaaatcgc tagcgggctg ctaaaggaag cggaacacgt   2220
agaaagccag tccgcagaaa cggtgctgac cccggatgaa tgtcagctac tgggctatct   2280
ggacaaggga aaacgcaagc gcaaagagaa agcaggtagc ttgcagtggg cttacatggc   2340
gatagctaga ctgggcggtt ttatggacag caagcgaacc ggaattgcca gctggggcgc   2400
cctctggtaa ggttgggaag ccctgcaaag taaactggat ggctttcttg ccgccaagga   2460
tctgatggcg caggggatca agatctgatc aagagacagg atgaggatcg tttcgcatga   2520
```

-continued ttgaacaaga tggattgcac gcaggttctc cggccgcttg ggtggagagg ctattcggct 2580
atgactgggc acaacagaca atcggctgct ctgatgccgc cgtgttccgg ctgtcagcgc 2640
aggggcgccc ggttcttttt gtcaagaccg acctgtccgg tgccctgaat gaactgcagg 2700
acgaggcagc gcggctatcg tggctggcca cgacgggcgt tccttgcgca gctgtgctcg 2760
acgttgtcac tgaagcggga agggactggc tgctattggg cgaagtgccg gggcaggatc 2820
tcctgtcatc tcaccttgct cctgccgaga aagtatccat catggctgat gcaatgcggc 2880
ggctgcatac gcttgatccg gctacctgcc cattcgacca ccaagcgaaa catcgcatcg 2940
agcgagcacg tactcggatg gaagccggtc ttgtcgatca ggatgatctg gacgaagagc 3000
atcaggggct cgcgccagcc gaactgttcg ccaggctcaa ggcgcgcatg cccgacggcg 3060
aggatctcgt cgtgacccat ggcgatgcct gcttgccgaa tatcatggtg gaaaatggcc 3120
gcttttctgg attcatcgac tgtggccggc tgggtgtggc ggaccgctat caggacatag 3180
cgttggctac ccgtgatatt gctgaagagc ttggcggcga atgggctgac cgcttcctcg 3240
tgctttacgg tatcgccgct cccgattcgc agcgcatcgc cttctatcgc cttcttgacg 3300
agttcttctg agcgggactc tggggttcga aatgaccgac caagcgacgc ccaacctgcc 3360
atcacgagat ttcgattcca ccgccgcctt ctatgaaagg ttgggcttcg gaatcgtttt 3420
ccgggacgcc ggctggatga tcctccagcg cggggatctc atgctggagt tcttcgccca 3480
cgctagcggc gcgccggccg gcccggtgtg aaataccgca cagatgcgta aggagaaaat 3540
accgcatcag gcgctcttcc gcttcctcgc tcactgactc gctgcgctcg gtcgttcggc 3600
tgcggcgagc ggtatcagct cactcaaagg cggtaatacg gttatccaca gaatcagggg 3660
ataacgcagg aaagaacatg tgagcaaaag gccagcaaaa ggccaggaac cgtaaaaagg 3720
ccgcgttgct ggcgtttttc cataggctcc gcccccctga cgagcatcac aaaaatcgac 3780
gctcaagtca gaggtggcga aacccgacag gactataaag ataccaggcg tttccccctg 3840
gaagctccct cgtgcgctct cctgttccga ccctgccgct taccggatac ctgtccgcct 3900
ttctcccttc gggaagcgtg gcgctttctc atagctcacg ctgtaggtat ctcagttcgg 3960
tgtaggtcgt tcgctccaag ctgggctgtg tgcacgaacc ccccgttcag cccgaccgct 4020
gcgccttatc cggtaactat cgtcttgagt ccaacccggt aagacacgac ttatcgccac 4080
tggcagcagc cactggtaac aggattagca gagcgaggta tgtaggcggt gctacagagt 4140
tcttgaagtg gtggcctaac tacggctaca ctagaaggac agtatttggt atctgcgctc 4200
tgctgaagcc agttaccttc ggaaaaagag ttggtagctc ttgatccggc aaacaaacca 4260
ccgctggtag cggtggtttt tttgtttgca agcagcagat tacgcgcaga aaaaaaggat 4320
ctcaagaaga tcctttgatc ttttctacgg ggtctgacgc tcagtggaac gaaaactcac 4380
gttaagggat tttggtcatg agattatcaa aaaggatctt cacctagatc cttttaaagg 4440
ccggccgcgg ccgcgcaaag tcccgcttcg tgaaaatttt cgtgccgcgt gattttccgc 4500
caaaaacttt aacgaacgtt cgttataatg gtgtcatgac cttcacgacg aagtactaaa 4560
attggcccga atcatcagct atggatctct ctgatgtcgc gctggagtcc gacgcgctcg 4620
atgctgccgt cgatttaaaa acggtgatcg gatttttccg agctctcgat acgacggacg 4680
cgccagcatc acgagactgg gccagtgccg cgagcgacct agaaactctc gtggcggatc 4740
ttgaggagct ggctgacgag ctgcgtgctc ggccagcgcc aggaggacgc acagtagtgg 4800
aggatgcaat cagttgcgcc tactgcggtg gcctgattcc tccccggcct gacccgcgag 4860
gacggcgcgc aaaatattgc tcagatgcgt gtcgtgccgc agccagccgc gagcgcgcca 4920
acaaacgcca cgccgaggag ctggaggcgg ctaggtcgca aatggcgctg gaagtgcgtc 4980
ccccgagcga aattttggcc atggtcgtca cagagctgga agcggcagcg agaattatcg 5040
cgatcgtggc ggtgcccgca ggcatgacaa acatcgtaaa tgccgcgttt cgtgtgccgt 5100
ggccgcccag gacgtgtcag cgccgccacc acctgcaccg aatcggcagc agcgtcgcgc 5160
gtcgaaaaag cgcacaggcg gcaagaagcg ataagctgca cgaatacctg aaaaatgttg 5220
aacgccccgt gagcggtaac tcacagggcg tcggctaacc cccagtccaa acctgggaga 5280
aagcgctcaa aaatgactct agcggattca cgagacattg acacaccggc ctggaaattt 5340
tccgctgatc tgttcgacac ccatcccgag ctcgcgctgc gatcacgtgg ctggacgagc 5400
gaagaccgcc gcgaattcct cgctcacctg ggcagagaaa atttccaggg cagcaagacc 5460
cgcgacttcg ccagcgcttg gatcaaagac ccggacacgg agaaacacag ccgaagttat 5520
accgagttgg ttcaaaatcg cttgcccggt gccagtatgt tgctctgacg cacgcgcagc 5580
acgcagccgt gcttgtcctg gacattgatg tgccgagcca ccaggccggc gggaaaatcg 5640
agcacgtaaa ccccgaggtc tacgcgattt tggagcgctg ggcacgcctg gaaaaagcgc 5700
cagcttggat cggcgtgaat ccactgagcg ggaaatgcca gctcatctgg ctcattgatc 5760
cggtgtatgc cgcagcaggc atgagcagcc cgaatatgcg cctgctggct gcaacgaccg 5820
aggaaatgac ccgcgttttc ggcgctgacc aggctttttc acataggctg agccgtggcc 5880
actgcactct ccgacgatcc cagccgtacc gctggcatgc ccagcacaat cgcgtggatc 5940
gcctagctga tcttatggag gttgctcgca tgatctcagg cacagaaaaa cctaaaaaac 6000
gctatgagca ggagttttct agcggacggg cacgtatcga agcggcaaga aaagccactg 6060
cggaagcaaa agcacttgcc acgcttgaag caagcctgcc gagcgccgct gaagcgtctg 6120
gagagctgat cgacggcgtc cgtgtcctct ggactgctcc agggcgtgcc gcccgtgatg 6180
agacggcttt tcgccacgct ttgactgtgg gataccagtt aaaagcggct ggtgagcgcc 6240
taaaagacac caagggtcat cgagcctacg agcgtgccta caccgtcgct caggcggtcg 6300
gaggaggccg tgagcctgat ctgccgccgg actgtgaccg ccagacggat tggccgcgac 6360
gtgtgcgcgg ctacgtcgct aaaggccagc cagtcgtccc tgctcgtcag acagagacgc 6420
agagccagcc g 6431

<210> SEQ ID NO 49
<211> LENGTH: 6431
<212> TYPE: DNA
<213> ORGANISM: Artificial Sequence
<220> FEATURE:
<223> OTHER INFORMATION: Description of Artificial Sequence: Synthetic construct

<400> SEQUENCE: 49
aggcgaaaag ctctggccac tatgggaaga cgtggcggta aaaaggccgc agaacgctgg 60
aaagacccaa acagtgagta cgcccgagca cagcgagaaa aactagctaa gtccagtcaa 120
cgacaagcta ggaaagctaa aggaaatcgc ttgaccattg caggttggtt tatgactgtt 180
gagggagaga ctggctcgtg gccgacaatc aatgaagcta tgtctgaatt tagcgtgtca 240
cgtcagaccg tgaatagagc acttaaggtc tgcgggcatt gaacttccac gaggacgccg 300
aaagcttccc agtaaatgtg ccatctcgta ggcagaaaac ggttccccccg tagggtctct 360 ctcttggcct cctttctagg tcgggctgat tgctcttgaa gctctctagg ggggctcaca 420
ccataggcag ataacgttcc ccaccggctc gcctcgtaag cgcacaagga ctgctcccaa 480

-continued

```
agatcttcaa agccactgcc gcgactgcct tcgcgaagcc ttgccccgcg gaaatttcct    540
ccaccgagtt cgtgcacacc cctatgccaa gcttctttca ccctaaattc gagagattgg    600
attcttaccg tggaaattct tcgcaaaaat cgtcccctga tcgcccttgc gacgttggcg    660
tcggtgccgc tggttgcgct tggcttgacc gacttgatca gcggccgctc gatttaaatc    720
tcgagcggct taaagtttgg ctgccatgtg aatttttagc accctcaaca gttgagtgct    780
ggcactctcg gggtagagt gccaaatagg ttgtttgaca cacagttgtt cacccgcgac    840
gacggctgtg ctggaaaccc acaaccggca cacacaaaat tttctcatg aagggattgc    900
atatgcccac cctcgcgcct tcaggtcaac ttgaaatcca agcgatcggt gatgtctcca    960
ccgaagccgg agcaatcatt acaaacgctg aaatcgccta tcaccgctgg ggtgaatacc   1020
gcgtagataa agaaggacgc agcaatgtcg ttctcatcga acacgccctc actggagatt   1080
ccaacgcagc cgattggtgg gctgacttgc tcggtcccgg caaagccatc aacactgata   1140
tttactgcgt gatctgtacc aacgtcatcg gtggttgcaa cggttccacc ggacctggct   1200
ccatgcatcc agatggaaat ttctggggta atcgcttccc cgccacgtcc attcgtgatc   1260
aggtaaacgc cgaaaaacaa ttcctcgacg cactcggcat caccacggtc gccgcagtac   1320
ttggtggttc catgggtggt gcccgcaccc tagagtgggc cgcaatgtac ccagaaactg   1380
ttggcgcagc tgctgttctt gcagtttctg cacgcgccag cgcctggcaa atcggcattc   1440
aatccgccca aattaaggcg attgaaaacg accaccactg gcacgaaggc aactactacg   1500
aatccggctg caacccagcc accggactcg gcgccgcccg acgcatcgcc cacctcacct   1560
accgtggcga actagaaatc gacgaacgct tcggcaccaa agcccaaaag aacgaaaacc   1620
cactcggtcc ctaccgcaag cccgaccagc gcttcgccgt ggaatcctac ttggactacc   1680
aagcagacaa gctagtacag cgtttcgacg ccggctccta cgtcttgctc accgacgccc   1740
tcaaccgcca cgacattggt cgcgaccgcg gaggcctcaa caaggcactc gaatccatca   1800
aagttccagt ccttgtcgca ggcgtagata ccgatatttt gtacccctac caccagcaag   1860
aacacctctc cagaaacctg ggaaatctac tggcaatggc aaaaatcgta tcccctgtcg   1920
gccacgatgc tttcctcacc gaaagccgcc aaatggatcg catcgtgagg aacttcttca   1980
gcctcatctc cccagacgaa gacaaccctt cgacctacat cgagttctac atctaaacta   2040
gttcggacct agggatatcg tcgacatcga tgctcttctg cgttaattaa caattgggat   2100
cctctagagt tctgtgaaaa acaccgtggg gcagtttctg cttcgcggtg tttttattt    2160
gtggggcact agacccggga tttaaatcgc tagcgggctg ctaaaggaag cggaacacgt   2220
agaaagccag tccgcagaaa cggtgctgac cccggatgaa tgtcagctac tgggctatct   2280
ggacaaggga aaacgcaagc gcaaagagaa agcaggtagc ttgcagtggg cttacatggc   2340
gatagctaga ctgggcggtt ttatggacag caagcgaacc ggaattgcca gctggggcgc   2400
cctctggtaa ggttgggaag ccctgcaaag taaactggat ggctttcttg ccgccaagga   2460
tctgatggcg caggggatca agatctgatc aagagacagg atgaggatcg tttcgcatga   2520
ttgaacaaga tggattgcac gcaggttctc cggccgcttg ggtggagagg ctattcggct   2580
atgactgggc acaacagaca atcggctgct ctgatgccgc cgtgttccgg ctgtcagcgc   2640
aggggcgccc ggttcttttt gtcaagaccg acctgtccgg tgccctgaat gaactgcagg   2700
acgaggcagc gcggctatcg tggctggcca cgacgggcgt tccttgcgca gctgtgctcg   2760
acgttgtcac tgaagcggga agggactggc tgctattggg cgaagtgccg gggcaggatc   2820
tcctgtcatc tcaccttgct cctgccgaga aagtatccat catggctgat gcaatgcggc   2880
```

-continued

```
ggctgcatac gcttgatccg gctacctgcc cattcgacca ccaagcgaaa catcgcatcg   2940

agcgagcacg tactcggatg gaagccggtc ttgtcgatca ggatgatctg gacgaagagc   3000

atcaggggct cgcgccagcc gaactgttcg ccaggctcaa ggcgcgcatg cccgacggcg   3060

aggatctcgt cgtgacccat ggcgatgcct gcttgccgaa tatcatggtg gaaaatggcc   3120

gcttttctgg attcatcgac tgtggccggc tgggtgtggc ggaccgctat caggacatag   3180

cgttggctac ccgtgatatt gctgaagagc ttggcggcga atgggctgac cgcttcctcg   3240

tgctttacgg tatcgccgct cccgattcgc agcgcatcgc cttctatcgc cttcttgacg   3300

agttcttctg agcgggactc tggggttcga aatgaccgac caagcgacgc ccaacctgcc   3360

atcacgagat ttcgattcca ccgccgcctt ctatgaaagg ttgggcttcg gaatcgtttt   3420

ccgggacgcc ggctggatga tcctccagcg cggggatctc atgctggagt tcttcgccca   3480

cgctagcggc gcgccggccg gcccggtgtg aaataccgca cagatgcgta aggagaaaat   3540

accgcatcag gcgctcttcc gcttcctcgc tcactgactc gctgcgctcg gtcgttcggc   3600

tgcggcgagc ggtatcagct cactcaaagg cggtaatacg gttatccaca gaatcagggg   3660

ataacgcagg aaagaacatg tgagcaaaag gccagcaaaa ggccaggaac cgtaaaaagg   3720

ccgcgttgct ggcgtttttc cataggctcc gcccccctga cgagcatcac aaaaatcgac   3780

gctcaagtca gaggtggcga aacccgacag gactataaag ataccaggcg tttccccctg   3840

gaagctccct cgtgcgctct cctgttccga ccctgccgct taccggatac ctgtccgcct   3900

ttctcccttc gggaagcgtg gcgctttctc atagctcacg ctgtaggtat ctcagttcgg   3960

tgtaggtcgt tcgctccaag ctgggctgtg tgcacgaacc ccccgttcag cccgaccgct   4020

gcgccttatc cggtaactat cgtcttgagt ccaacccggt aagacacgac ttatcgccac   4080

tggcagcagc cactggtaac aggattagca gagcgaggta tgtaggcggt gctacagagt   4140

tcttgaagtg gtggcctaac tacggctaca ctagaaggac agtatttggt atctgcgctc   4200

tgctgaagcc agttaccttc ggaaaaagag ttggtagctc ttgatccggc aaacaaacca   4260

ccgctggtag cggtggtttt tttgtttgca agcagcagat tacgcgcaga aaaaaaggat   4320

ctcaagaaga tcctttgatc ttttctacgg ggtctgacgc tcagtggaac gaaaactcac   4380

gttaagggat tttggtcatg agattatcaa aaaggatctt cacctagatc cttttaaagg   4440

ccggccgcgg ccgcgcaaag tcccgcttcg tgaaaatttt cgtgccgcgt gattttccgc   4500

caaaaacttt aacgaacgtt cgttataatg gtgtcatgac cttcacgacg aagtactaaa   4560

attggcccga atcatcagct atggatctct ctgatgtcgc gctggagtcc gacgcgctcg   4620

atgctgccgt cgatttaaaa acggtgatcg gatttttccg agctctcgat acgacggacg   4680

cgccagcatc acgagactgg gccagtgccg cgagcgacct agaaactctc gtggcggatc   4740

ttgaggagct ggctgacgag ctgcgtgctc ggccagcgcc aggaggacgc acagtagtgg   4800

aggatgcaat cagttgcgcc tactgcggtg gcctgattcc tccccggcct gacccgcgag   4860

gacggcgcgc aaaatattgc tcagatgcgt gtcgtgccgc agccagccgc gagcgcgcca   4920

acaaacgcca cgccgaggag ctggaggcgg ctaggtcgca aatggcgctg gaagtgcgtc   4980

ccccgagcga aattttggcc atggtcgtca cagagctgga agcggcagcg agaattatcg   5040

cgatcgtggc ggtgcccgca ggcatgacaa acatcgtaaa tgccgcgttt cgtgtgccgt   5100

ggccgcccag gacgtgtcag cgccgccacc acctgcaccg aatcggcagc agcgtcgcgc   5160

gtcgaaaaag cgcacaggcg gcaagaagcg ataagctgca cgaatacctg aaaaatgttg   5220

aacgccccgt gagcggtaac tcacagggcg tcggctaacc cccagtccaa acctgggaga   5280
```

```
aagcgctcaa aaatgactct agcggattca cgagacattg acacaccggc ctggaaattt   5340
tccgctgatc tgttcgacac ccatcccgag ctcgcgctgc gatcacgtgg ctggacgagc   5400
gaagaccgcc gcgaattcct cgctcacctg ggcagagaaa atttccaggg cagcaagacc   5460
cgcgacttcg ccagcgcttg gatcaaagac ccggacacgg agaaacacag ccgaagttat   5520
accgagttgg ttcaaaatcg cttgcccggt gccagtatgt tgctctgacg cacgcgcagc   5580
acgcagccgt gcttgtcctg gacattgatg tgccgagcca ccaggccggc gggaaaatcg   5640
agcacgtaaa ccccgaggtc tacgcgattt tggagcgctg ggcacgcctg gaaaaagcgc   5700
cagcttggat cggcgtgaat ccactgagcg ggaaatgcca gctcatctgg ctcattgatc   5760
cggtgtatgc cgcagcaggc atgagcagcc cgaatatgcg cctgctggct gcaacgaccg   5820
aggaaatgac ccgcgttttc ggcgctgacc aggctttttc acataggctg agccgtggcc   5880
actgcactct ccgacgatcc cagccgtacc gctggcatgc ccagcacaat cgcgtggatc   5940
gcctagctga tcttatggag gttgctcgca tgatctcagg cacagaaaaa cctaaaaaac   6000
gctatgagca ggagttttct agcggacggg cacgtatcga agcggcaaga aaagccactg   6060
cggaagcaaa agcacttgcc acgcttgaag caagcctgcc gagcgccgct gaagcgtctg   6120
gagagctgat cgacggcgtc cgtgtcctct ggactgctcc agggcgtgcc gcccgtgatg   6180
agacggcttt tcgccacgct ttgactgtgg gataccagtt aaaagcggct ggtgagcgcc   6240
taaaagacac caagggtcat cgagcctacg agcgtgccta caccgtcgct caggcggtcg   6300
gaggaggccg tgagcctgat ctgccgccgg actgtgaccg ccagacggat tggccgcgac   6360
gtgtgcgcgg ctacgtcgct aaaggccagc cagtcgtccc tgctcgtcag acagagacgc   6420
agagccagcc g                                                        6431
```

<210> SEQ ID NO 50
<211> LENGTH: 1005
<212> TYPE: DNA
<213> ORGANISM: Corynebacterium glutamicum

<400> SEQUENCE: 50

```
atgaacctaa agaaccccga aacgccagac cgtaaccttg ctatggagct ggtgcgagtt     60
acggaagcag ctgcactggc ttctggacgt tgggttggac gtggcatgaa gaatgaaggc    120
gacggtgccg ctgttgacgc catgcgccag ctcatcaact cagtgaccat gaagggcgtc    180
gttgttatcg gcgagggcga aaaagacgaa gctccaatgc tgtacaacgg cgaagaggtc    240
ggaaccggct ttggacctga ggttgatatc gcagttgacc cagttgacgg caccaccctg    300
atggctgagg gtcgccccaa cgcaatttcc attctcgcag ctgcagagcg tggcaccatg    360
tacgatccat cctccgtctt ctacatgaag aagatcgccg tgggacctga ggccgcaggc    420
aagatcgaca tcgaagctcc agttgcccac aacatcaacg cggtggcaaa gtccaaggga    480
atcaaccctt ccgacgtcac cgttgtcgtg cttgaccgtc ctcgccacat cgaactgatc    540
gcagacattc gtcgtgcagg cgcaaaggtt cgtctcatct ccgacggcga cgttgcaggt    600
gcagttgcag cagctcagga ttccaactcc gtggacatca tgatgggcac cggcggaacc    660
ccagaaggca tcatcactgc gtgcgccatg aagtgcatgg gtggcgaaat ccagggcatc    720
ctggccccaa tgaacgattt cgagcgccag aaggcacacg acgctggtct ggttcttgat    780
caggttctgc acaccaacga tctggtgagc tccgacaact gctacttcgt ggcaaccggt    840
gtgaccaacg gtgacatgct ccgtggcgtt tcctaccgcg caaacggcgc aaccacccgt    900
tccctggtta tgcgcgcaaa gtcaggcacc atccgccaca tcgagtctgt ccaccagctg    960
```

-continued

```
tccaagctgc aggaatactc cgtggttgac tacaccaccg cgacc                1005


<210> SEQ ID NO 51
<211> LENGTH: 335
<212> TYPE: PRT
<213> ORGANISM: Corynebacterium glutamicum

<400> SEQUENCE: 51

Met Asn Leu Lys Asn Pro Glu Thr Pro Asp Arg Asn Leu Ala Met Glu
  1             5                  10                  15

Leu Val Arg Val Thr Glu Ala Ala Ala Leu Ala Ser Gly Arg Trp Val
            20                  25                  30

Gly Arg Gly Met Lys Asn Glu Gly Asp Gly Ala Ala Val Asp Ala Met
        35                  40                  45

Arg Gln Leu Ile Asn Ser Val Thr Met Lys Gly Val Val Val Ile Gly
     50                  55                  60

Glu Gly Glu Lys Asp Glu Ala Pro Met Leu Tyr Asn Gly Glu Glu Val
 65                  70                  75                  80

Gly Thr Gly Phe Gly Pro Glu Val Asp Ile Ala Val Asp Pro Val Asp
                 85                  90                  95

Gly Thr Thr Leu Met Ala Glu Gly Arg Pro Asn Ala Ile Ser Ile Leu
            100                 105                 110

Ala Ala Ala Glu Arg Gly Thr Met Tyr Asp Pro Ser Ser Val Phe Tyr
        115                 120                 125

Met Lys Lys Ile Ala Val Gly Pro Glu Ala Ala Gly Lys Ile Asp Ile
    130                 135                 140

Glu Ala Pro Val Ala His Asn Ile Asn Ala Val Ala Lys Ser Lys Gly
145                 150                 155                 160

Ile Asn Pro Ser Asp Val Thr Val Val Val Leu Asp Arg Pro Arg His
                165                 170                 175

Ile Glu Leu Ile Ala Asp Ile Arg Arg Ala Gly Ala Lys Val Arg Leu
            180                 185                 190

Ile Ser Asp Gly Asp Val Ala Gly Ala Val Ala Ala Ala Gln Asp Ser
        195                 200                 205

Asn Ser Val Asp Ile Met Met Gly Thr Gly Gly Thr Pro Glu Gly Ile
    210                 215                 220

Ile Thr Ala Cys Ala Met Lys Cys Met Gly Gly Glu Ile Gln Gly Ile
225                 230                 235                 240

Leu Ala Pro Met Asn Asp Phe Glu Arg Gln Lys Ala His Asp Ala Gly
                245                 250                 255

Leu Val Leu Asp Gln Val Leu His Thr Asn Asp Leu Val Ser Ser Asp
            260                 265                 270

Asn Cys Tyr Phe Val Ala Thr Gly Val Thr Asn Gly Asp Met Leu Arg
        275                 280                 285

Gly Val Ser Tyr Arg Ala Asn Gly Ala Thr Thr Arg Ser Leu Val Met
    290                 295                 300

Arg Ala Lys Ser Gly Thr Ile Arg His Ile Glu Ser Val His Gln Leu
305                 310                 315                 320

Ser Lys Leu Gln Glu Tyr Ser Val Val Asp Tyr Thr Thr Ala Thr
                325                 330                 335


<210> SEQ ID NO 52
<211> LENGTH: 6
<212> TYPE: DNA
<213> ORGANISM: Corynebacterium glutamicum

<400> SEQUENCE: 52
```

-continued

```
tagagt                                                                 6


<210> SEQ ID NO 53
<211> LENGTH: 7
<212> TYPE: DNA
<213> ORGANISM: Corynebacterium glutamicum

<400> SEQUENCE: 53

ggaggga                                                                7
```

PGRO EXPRESSION UNITS

RELATED APPLICATIONS

This application is a divisional of U.S. application Ser. No. 10/582,822 filed Jun. 14, 2006 which is a 35 U.S.C. 371 National stage filing of International Application No. PCT/EP2004/014263, filed Dec. 15, 2004, which claims priority to German Application No. 103 59 595.3, filed Dec. 18, 2003. The entire contents of each of these applications are hereby incorporated by reference herein.

SEQUENCE LISTING

This application incorporates herein by reference the sequence listing filed concurrently herewith, i.e., the file "Sequence Listing" (113 KB), which is a text document created on Feb. 12, 2008.

SPECIFICATION

The present invention relates to the use of nucleic acid sequences for regulating the transcription and expression of genes, the novel promoters and expression units themselves, methods for altering or causing the transcription rate and/or expression rate of genes, expression cassettes comprising the expression units, genetically modified microorganisms with altered or caused transcription rate and/or expression rate, and methods for preparing biosynthetic products by cultivating the genetically modified microorganisms.

Various biosynthetic products such as, for example, fine chemicals, such as, inter alia, amino acids, vitamins, but also proteins, are produced in cells by natural metabolic processes and are used in many branches of industry, including the cosmetics, feed, food and pharmaceutical industries. These substances, which are referred to collectively as fine chemicals/proteins, comprise inter alia organic acids, both proteinogenic and non-proteinogenic amino acids, nucleotides and nucleosides, lipids and fatty acids, diols, carbohydrates, aromatic compounds, vitamins and cofactors, and proteins and enzymes. Their production takes place most expediently on the industrial scale by culturing bacteria which have been developed in order to produce and secrete large quantities of the particular desired substance. Organisms particularly suitable for this purpose are coryneform bacteria, gram-positive non-pathogenic bacteria.

It is known that amino acids are prepared by fermentation of strains of coryneform bacteria, especially *Corynebacterium glutamicum*. Because of the great importance, continuous work is done on improving the production processes. Process improvements may relate to fermentation technique measures such as, for example, stirring and oxygen supply, or the composition of the nutrient media, such as, for example, the sugar concentration during the fermentation, or the working up to give the product, for example by ion exchange chromatography or else spray drying, or the intrinsic performance properties of the microorganism itself.

Methods of recombinant DNA technology have likewise been employed for some years for strain improvement of *Corynebacterium* strains producing fine chemical/proteins, by amplifying individual genes and investigating the effect on the production of fine chemicals/proteins.

Other ways for developing a process for producing fine chemicals, amino acids or proteins, or for increasing or improving the productivity of a pre-existing process for producing fine chemicals, amino acids or proteins, are to increase or to alter the expression of one or more genes, and/or to influence the translation of an mRNA by suitable polynucleotide sequences. In this connection, influencing may include increasing, reducing, or else other parameters of the expression of genes, such as chronological expression patterns.

Various constituents of bacterial regulatory sequences are known to the skilled worker. A distinction is made between the binding sites for regulators, also called operators, the binding sites for RNA polymerase holoenzymes, also called −35 and −10 regions, and the binding site for ribosomal 16S RNA, also called ribosome binding site or else Shine-Dalgarno sequence.

The sequence of a ribosome binding site, also called Shine-Dalgarno sequence, means for the purposes of this invention polynucleotide sequences which are located up to 20 bases upstream of the translation initiation codon.

In the literature (*E. coli* and *S. typhimurium*, Neidhardt F. C. 1995 ASM Press) it is reported that both the composition of the polynucleotide sequence of the Shine-Dalgarno sequence, the sequence string of the bases, but also the distance of a polynucleotide sequence present in the Shine-Dalgarno sequence from has a considerable influence on the translation initiation rate.

Nucleic acid sequences having promoter activity can influence the formation of mRNA in various ways. Promoters whose activities are independent of the physiological growth phase of the organism are called constitutive. Other promoters in turn respond to external chemical and physical stimuli such as oxygen, metabolites, heat pH, etc. Others in turn show a strong dependence of their activity in different growth phases. For example, promoters showing a particularly pronounced activity during the exponential growth phase of microorganisms, or else precisely in the stationary phase of microbial growth, are described in the literature. Both characteristics of promoters may have a beneficial effect on productivity for a production of fine chemicals and proteins, depending on the metabolic pathway.

For example, promoters which switch off the expression of a gene during growth, but switch it on after an optimal growth, can be used to regulate gene which controls the production of a metabolite. The modified strain then displays the same growth parameters as the starting strain but produces more product per cell. This type of modification may increase both the titer (g of product/liter) and the C yield (g of product/g of C source).

It has already been possible to isolate in *Corynebacterium* species those nucleotide sequences which can be used to increase or diminish gene expression. These regulated promoters may increase or reduce the rate at which a gene is transcribed, depending on the internal and/or external conditions of the cell. In some cases, the presence of a particular factor, known as inducer, can stimulate the rate of transcription from the promoter. Inducers may influence transcription from the promoter either directly or indirectly. Another class of factors, known as suppressors, is able to reduce or else inhibit the transcription from the promoter, Like the inducers, the suppressors can also act directly or indirectly. However, temperature-regulated promoters are also known. Thus, the level of transcription of such promoters can be increased or else diminished for example by increasing the growth temperature above the normal growth temperature of the cell.

A small number of promoters from *C. glutamicum* have been described to date. The promoter of the malate synthase gene from *C. glutamicum* was described in DE 4440118. This promoter was inserted upstream of a structural gene coding for a protein. After transformation of such a construct into a coryneform bacterium there is regulation of the expression of the structural gene downstream of the promoter. Expression of the structural gene is induced as soon as an appropriate inducer is added to the medium.

Reinscheid et al., Microbiology 145:503 (1999) described a transcriptional fusion between the pta-ack promoter from *C. glutamicum* and a reporter gene (chloramphenicol acetyltransferase). Cells of *C. glutamicum* comprising such a transcriptional fusion exhibited increased expression of the reporter gene on growth on acetate-containing medium. By comparison with this, transformed cells which grew on glucose showed no increased expression of this reporter gene.

Pa'tek et al., Microbiology 142:1297 (1996) describe some DNA sequences from *C. glutamicum* which are able to enhance the expression of a reporter gene in *C. glutamicum* cells. These sequences were compared together in order to define consensus sequences for *C. glutamicum* promoters.

Further DNA sequences from *C. glutamicum* which can be used to regulate gene expression have been described in the patent WO 02/40679. These isolated polynucleotides represent expression units from *Corynebacterium glutamicum* which can be used either to increase or else to reduce gene expression. This patent additionally describes recombinant plasmids on which the expression units from *Corynebacterium glutamicum* are associated with heterologous genes. The method described herein, of fusing a promoter from *Corynebacterium glutamicum* with a heterologous gene, can be employed inter alia for regulating the genes of amino acid biosynthesis.

BRIEF SUMMARY OF THE INVENTION

It is an object of the present invention to provide further promoters and/or expression units with advantageous properties.

We have found that this object is achieved by the use of a nucleic acid having promoter activity, comprising A) the nucleic acid sequence SEQ. ID. NO. 1 or B) a sequence derived from this sequence by substitution, insertion or deletion of nucleotides and having an identity of at least 90% at the nucleic acid level with the sequence SEQ. ID. NO. 1, or C) a nucleic acid sequence which hybridizes with the nucleic acid sequence SEQ. ID. NO. 1 under stringent conditions, or D) functionally equivalent fragments of the sequences of A), B) or C) for the transcription of genes.

DETAILED DESCRIPTION OF THE INVENTION

Figure 1:
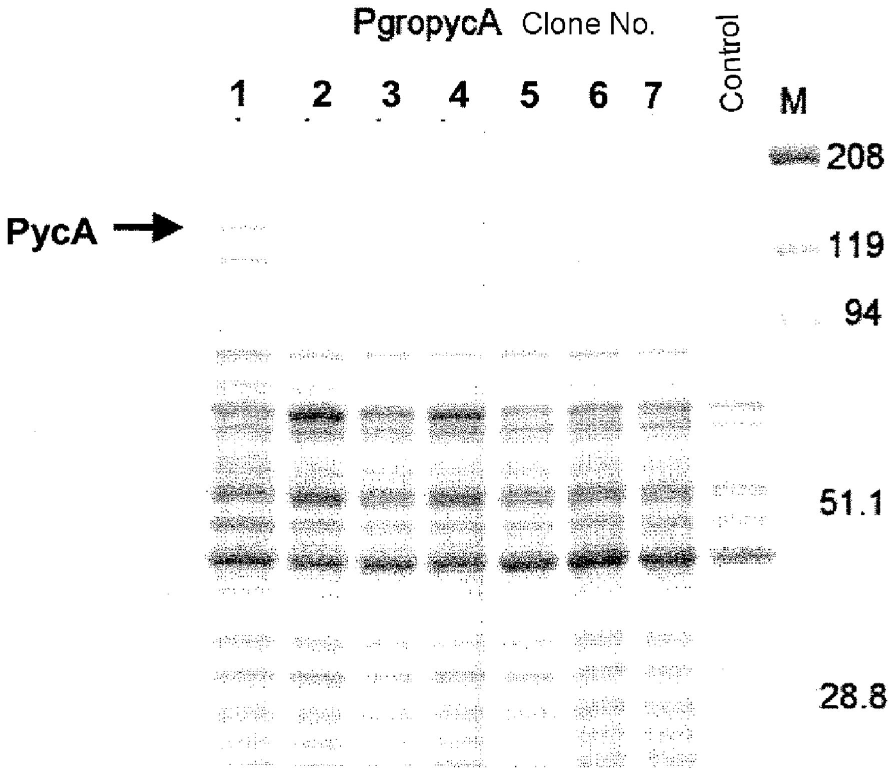
FIG. 1 shows a 10% SDS gel of the Pgro pycA clones.

"Transcription" means according to the invention the process by which a complementary RNA molecule is produced starting from a DNA template. Proteins such as RNA polymerase, so-called sigma factors and transcriptional regulator proteins are involved in this process. The synthesized RNA is then used as template in the translation process, which then leads to the biosynthetically active protein.

The formation rate with which a biosynthetically active protein is produced is a product of the rate of transcription and of translation. Both rates can be influenced according to the invention, and thus influence the rate of formation of products in a microorganism.

A "promoter" or a "nucleic acid having promoter activity" means according to the invention a nucleic acid which, in a functional linkage to a nucleic acid to be transcribed, regulates the transcription of this nucleic acid.

A "functional linkage" means in this connection for example the sequential arrangement of one of the nucleic acids of the invention having promoter activity and a nucleic acid sequence to be transcribed and, where appropriate, further regulatory elements such as, for example, nucleic acid sequences which ensure the transcription of nucleic acids, and for example a terminator, in such a way that each of the regulatory elements is able to fulfill its function in the transcription of the nucleic acid sequence. A direct linkage in the chemical sense is not absolutely necessary therefor. Genetic control sequences, such as, for example, enhancer sequences, are able to exercise their function on the target sequence even from more remote positions or even from other DNA molecules. Arrangements in which the nucleic acid sequence to be transcribed is positioned behind (i.e. at the 3' end) of the promoter sequence of the invention, so that the two sequences are covalently connected together, are preferred. In this connection, the distance between the promoter sequence and the nucleic acid sequence to be expressed transgenically is preferably fewer than 200 base pairs, particularly preferably less than 100 base pairs, very particularly preferably less than 50 base pairs.

Promoter activity means according to the invention the quantity or RNA formed by the promoter in a particular time, that is to say the transcription rate.

"Specific promoter activity" means according to the invention the quantity of RNA formed by the promoter in a particular time for each promoter.

The term "wild type" means according to the invention the appropriate starting microorganism.

Depending on the context, the term "microorganism" means the starting microorganism (wild type) or a genetically modified microorganism of the invention, or both.

Preferably, and especially in cases where the microorganism or the wild type cannot be unambiguously assigned, "wild type" means for the alteration or causing of the promoter activity or transcription rate, for the alteration of causing of the expression activity or expression rate and for increasing the content of biosynthetic products in each case a reference organism.

In a preferred embodiment, this reference organism is *Corynebacterium glutamicum* ATCC 13032.

In a preferred embodiment, the starting microorganisms used are already able to produce the desired fine chemical. Particular preference is given in this connection among the particularly preferred microorganisms of bacteria of the genus *Corynebacterium* and the particularly preferred fine chemicals L-lysine, L-methionine and L-threonine to those starting microorganisms already able to produce L-lysine, L-methionine and/or L-threonine. These are particularly preferably *corynebacteria* in which, for example, the gene coding for an aspartokinase (ask gene) is deregulated or the feedback inhibition is abolished or reduced. Such bacteria have, for example, a mutation leading to a reduction or abolition of the feedback inhibition, such as, for example, the mutation T311I, in the ask gene.

In the case of a "caused promoter activity" or transcription rate in relation to a gene compared with the wild type, therefore, compared with the wild type the formation of an RNA which was not present in this way in the wild type is caused.

In the case of an altered promoter activity or transcription rate in relation to a gene compared with the wild type, therefore, compared with the wild type the quantity of RNA produced in a particular time is altered.

"Altered" means in this connection preferably increased or reduced.

This can take place for example by increasing or reducing the specific promoter activity of the endogenous promoter of the invention, for example by mutating the promoter or by stimulating or inhibiting the promoter.

A further possibility is to achieve the increased promoter activity or transcription rate for example by regulating the transcription of genes in the microorganism by nucleic acids of the invention having promoter activity or by nucleic acids with increased specific promoter activity, where the genes are heterologous in relation to the nucleic acids having promoter activity.

The regulation of the transcription of genes in the microorganism by nucleic acids of the invention having promoter activity or by nucleic acids with increased specific promoter activity is preferably achieved by introducing one or more nucleic acids of the invention having promoter activity, appropriate with altered specific promoter activity, into the genome of the microorganism so that transcription of one or more endogenous genes takes place under the control of the introduced nucleic acid of the invention having promoter activity, appropriate with altered specific promoter activity, or introducing one or more genes into the genome of the microorganism so that transcription of one or more of the introduced genes takes place under the control of the endogenous nucleic acids of the invention having promoter activity, where appropriate with altered specific promoter activity, or introducing one or more nucleic acid constructs comprising a nucleic acid of the invention having promoter activity, where appropriate with altered specific promoter activity, and functionally linked one or more nucleic acids to be transcribed, into the microorganism.

The nucleic acids of the invention having promoter activity comprise

A) the nucleic acid sequence SEQ. ID. NO. 1 or
B) a sequence derived from this sequence by substitution, insertion or deletion of nucleotides and having an identity of at least 90% at the nucleic acid level with the sequence SEQ. ID. NO. 1, or C) a nucleic acid sequence which hybridizes with the nucleic acid sequence SEQ. ID. NO. 1 under stringent conditions, or
D) functionally equivalent fragments of the sequences of A), B) or C).

The nucleic acid sequence SEQ. ID. NO. 1 represents the promoter sequence of GroES chaperonin (Pgro) from *Corynebacterium glutamicum*. SEQ. ID. NO. 1 corresponds to the promoter sequence of the wild type.

The invention additionally relates to nucleic acids having promoter activity comprising a sequence derived from this sequence by substitution, insertion or deletion of nucleotides and having an identity of at least 90% at the nucleic acid level with the sequence SEQ. ID. NO. 1.

Further natural examples of the invention for promoters of the invention can easily be found for example from various organisms whose genomic sequence is known, by identity comparisons of the nucleic acid sequences from databases with the sequence SEQ ID NO: 1 described above.

Artificial promoter sequences of the invention can easily be found starting from the sequence SEQ ID NO: 1 by artificial variation and mutation, for example by substitution, insertion or deletion of nucleotides.

The term "substitution" means in the description the replacement of one or more nucleotides by one or more nucleotides. "Deletion" is the replacement of a nucleotide by a direct linkage. Insertions are insertions of nucleotides into the nucleic acid sequence, with formal replacement of a direct linkage by one or more nucleotides.

Identity between two nucleic acids means the identity of the nucleotides over the complete length of the nucleic acid in each case, in particular the identity calculated by comparison with the aid of the vector NTI Suite 7.1 software from Informax (USA) using the Clustal method (Higgins D G, Sharp P M. Fast and sensitive multiple sequence alignments on a microcomputer. Comput Appl. Biosci. 1989 April; 5(2):151-1), setting the following parameters, Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuplesize | 1 |
| Gap penalty | 3 |
| Window size | 5 |
| Number of best diagonals | 5 |

A nucleic acid sequence having an identity of at least 90% with the sequence SEQ ID NO: 1 accordingly means a nucleic acid sequence which, on comparison of its sequence with the sequence SEQ ID NO: 1, in particular in accordance with the above programming algorithm with the above parameter set, shows an identity of at least 90%.

Particularly preferred promoters show an identity of 91%, more preferably 92%, 93%, 94%, 95%, 96%, 97%, 98%, particularly preferably 99%, with the nucleic acid sequence SEQ. ID. NO. 1.

Further natural examples of promoters can moreover easily be found starting from the nucleic acid sequences described above, in particular starting from the sequence SEQ ID NO: 1 from various organisms whose genomic sequence is unknown, by hybridization techniques in a manner known per se.

A further aspect of the invention therefore relates to nucleic acids having promoter activity comprising a nucleic acid sequence which hybridizes with the nucleic acid sequence SEQ. ID. No. 1 under stringent conditions. This nucleic acid sequence comprises at least 10, more preferably more than 12, 15, 30, 50 or particularly preferably more than 150, nucleotides.

The hybridization takes place according to the invention under stringent conditions. Such hybridization conditions are described for example in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6:

Stringent hybridization conditions mean in particular: incubation at 42° C. overnight in a solution consisting of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured, sheared salmon sperm DNA, followed by washing the filters with 0.1×SSC at 65° C.

A "functionally equivalent fragment" means for nucleic acid sequences having promoter activity fragments which have substantially the same or a higher specific promoter activity than the starting sequence.

"Essentially identical" means a specific promoter activity which displays at least 50%, preferably 60%, more preferably 70%, more preferably 80%, more preferably 90%, particularly preferably 95% of the specific promoter activity of the starting sequence.

"Fragments" mean partial sequences of the nucleic acids having promoter activity which are described by embodiment A), B) or C). These fragments preferably have more than 10, but more preferably more than 12, 15, 30, 50 or particularly preferably more than 150, connected nucleotides of the nucleic acid sequence SEQ. ID. NO. 1.

It is particularly preferred to use the nucleic acid sequence SEQ. ID. NO. 1 as promoter, i.e. for transcription of genes.

SEQ. ID. NO. 1 has been described without assignment of function in the Genbank entry AP005283. The invention therefore further relates to the novel nucleic acid sequences of the invention having promoter activity.

The invention relates in particular to a nucleic acid having promoter activity, comprising A) the nucleic acid sequence SEQ. ID. NO. 1 or B) a sequence derived from this sequence by substitution, insertion or deletion of nucleotides and having an identity of at least 90% at the nucleic acid level with the sequence SEQ. ID. NO. 1, or C) a nucleic acid sequence which hybridizes with the nucleic acid sequence SEQ. ID. NO. 1 under stringent conditions, or D) functionally equivalent fragments of the sequences of A), B) or C), with the proviso that the nucleic acid having the sequence SEQ. ID. NO. 1 is excluded.

All the nucleic acids having promoter activity which are mentioned above can additionally be prepared in a manner known per se by chemical synthesis from the nucleotide building blocks such as, for example, by fragment condensation of individual overlapping complementary nucleic acid building blocks of the double helix. The chemical synthesis of oligonucleotides can take place for example in known manner by the phosphoramidite method (Voet, Voet, 2nd edition, Wiley Press New York, pp. 896-897).

Addition of synthetic oligonucleotides and filling in of gaps using the Klenow fragment of DNA polymerase and ligation reactions, and general cloning methods, are described in Sambrook et al. (1989), Molecular cloning: A laboratory manual, Cold Spring Harbor Laboratory Press.

The invention further relates to the use of an expression unit comprising one of the nucleic acids of the invention having promoter activity and additionally functionally linked a nucleic acid sequence which ensures the translation of ribonucleic acids for the expression of genes.

An expression unit means according to the invention a nucleic acid having expression activity, i.e a nucleic acid which, in functional linkage to a nucleic acid to be expressed, or gene, regulates the expression, i.e. the transcription and the translation of this nucleic acid or of this gene.

A "functional linkage" means in this connection for example the sequential arrangement of one of the expression units of the invention and of a nucleic acid sequence which is to be expressed transgenically and, where appropriate, further regulatory elements such as, for example, a terminator in such a way that each of the regulatory elements can fulfill its function in the transgenic expression of the nucleic acid sequence. A direct linkage in the chemical sense is not absolutely necessary for this. Genetic control sequences, such as, for example, enhancer sequences, can exercise their function on the target sequence also from more remote positions or even from different DNA molecules. Arrangements in which the nucleic acid sequence to be expressed transgenically is positioned behind (i.e. at the 3' end) the expression unit sequence of the invention, so that the two sequences are covalently connected together, are preferred. It is preferred in this case for the distance between the expression unit sequence and the nucleic acid sequence to be expressed transgenically to be less than 200 base pairs, particularly preferably fewer than 100 base pairs, very particularly preferably fewer than 50 base pairs.

"Expression activity" means according to the invention the quantity of protein produced in a particular time by the expression unit, i.e. the expression rate.

"Specific expression activity" means according to the invention the quantity of protein produced by the expression unit in a particular time for each expression unit.

In the case of a "caused expression activity" or expression rate in relation to a gene compared with the wild type, therefore, compared with the wild type the production of a protein which was not present in this way in the wild type is caused.

In the case of an "altered expression activity" or expression rate in relation to a gene compared with the wild type, therefore, compared with the wild type the quantity of protein produced in a particular time is altered.

"Altered" preferably means in this connection increased or decreased.

This can take place for example by increasing or reducing the specific activity of the endogenous expression unit, for example by mutating the expression unit or by stimulating or inhibiting the expression unit.

The increased expression activity or expression rate can moreover be achieved for example by regulating the expression of genes in the microorganism by expression units of the invention or by expression units with increased specific expression activity, where the genes are heterologous in relation to the expression units.

The regulation of the expression of genes in the microorganism by expression units of the invention or by expression units of the invention with increased specific expression activity is preferably achieved by introducing one or more expression units of the invention, where appropriate with altered specific expression activity, into the genome of the microorganism so that expression of one or more endogenous genes takes place under the control of the introduced expression units of the invention, where appropriate with altered specific expression activity, or introducing one or more genes into the genome of the microorganism so that expression of one or more of the introduced genes takes place under the control of the endogenous expression units of the invention, where appropriate with altered specific expression activity, or introducing one or more nucleic acid constructs comprising an expression unit of the invention, where appropriate with altered specific expression activity, and functionally linked one or more nucleic acids to be expressed, into the microorganism.

The expression units of the invention comprise a nucleic acid of the invention, described above, having promoter activity and additionally functionally linked a nucleic acid sequence which ensures the translation of ribonucleic acids.

This nucleic acid sequence which ensures the translation of ribonucleic acids preferably comprises the nucleic acid sequence SEQ. ID. NO. 42 as ribosome binding site.

In a preferred embodiment, the expression unit of the invention comprises:

E) the nucleic acid sequence SEQ. ID. NO. 2 or

F) a sequence derived from this sequence by substitution, insertion or deletion of nucleotides and having an identity of at least 90% at the nucleic acid level with the sequence SEQ. ID. NO. 2, or G) a nucleic acid sequence which hybridizes with the nucleic acid sequence SEQ. ID. NO. 2 under stringent conditions, or H) functionally equivalent fragments of the sequences of E), F) or G)

The nucleic acid sequence SEQ. ID. NO. 2 represents the nucleic acid sequence of the expression unit of GroES chaperonin (Pgro) from *Corynebacterium glutamicum*. SEQ. ID. NO. 2 corresponds to the sequence of the expression unit of the wild type.

The invention further relates to expression units comprising a sequence which is derived from this sequence by substitution, insertion or deletion of nucleotides and which have an identity of at least 90% at the nucleic acid level with the sequence SEQ. ID. NO, 2.

Further natural examples of the invention for expression units of the invention can easily be found for example from various organisms whose genomic sequence is known, by identity comparisons of the nucleic acid sequences from databases with the sequence SEQ ID NO: 2 described above.

Artificial sequences of the invention of the expression units can easily be found starting from the sequence SEQ ID NO: 2 by artificial variation and mutation, for example by substitution, insertion or deletion of nucleotides.

A nucleic acid sequence having an identity of at least 90% with the sequence SEQ ID NO, 2 accordingly means a nucleic acid sequence which, on comparison of its sequence with the sequence SEQ ID NO: 2, in particular in accordance with the above programming algorithm with the above parameter set, shows an identity of at least 90%.

Particularly preferred expression units show an identity of 91%, more preferably 92%, 93%, 94%, 95%, 96%, 97%, 98%, particularly preferably 99%, with the nucleic acid sequence SEQ. ID. NO. 2.

Further natural examples of expression units can moreover easily be found starting from the nucleic acid sequences described above, in particular starting from the sequence SEQ ID NO: 2 from various organisms whose genomic sequence is unknown, by hybridization techniques in a manner known per se.

A further aspect of the invention therefore relates to expression units comprising a nucleic acid sequence which hybridizes with the nucleic acid sequence SEQ. ID. No. 2 under stringent conditions. This nucleic acid sequence comprises at least 10, more preferably more than 12, 15, 30, 50 or particularly preferably more than 150, nucleotides.

"Hybridization" means the ability of a poly- or oligonucleotide to bind under stringent conditions to a virtually complementary sequence, while nonspecific bindings between non-complementary partners do not occur under these conditions. For this, the sequences ought preferably to be 90-100% complementary. The property of complementary sequences being able to bind specifically to one another is made use of for example in the Northern or Southern blotting technique or in primer binding in PCR or RT-PCR.

The hybridization takes place according to the invention under stringent conditions. Such hybridization conditions are described for example in Sambrook, J., Fritsch, E. F. Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6:

Stringent hybridization conditions mean in particular: incubation at 42° C. overnight in a solution consisting of 50% formamide, 5×SSC (750 mM NaCl, 75 mM trisodium citrate), 50 mM sodium phosphate (pH 7.6), 5×Denhardt's solution, 10% dextran sulfate and 20 g/ml denatured, sheared salmon sperm DNA, followed by washing the filters with 0.1×SSC at 65° C.

The nucleotide sequences of the invention further make it possible to produce probes and primers which can be used for identifying and/or cloning homologous sequences in other cell types and microorganisms. Such probes and primers normally comprise a nucleotide sequence region which hybridizes under stringent conditions onto a lcast approximately 12, preferably at least approximately 25, such as, for example, approximately 40, 50 or 75 consecutive nucleotides of a sense strand of a nucleic acid sequence of the invention or of a corresponding antisense strand.

Also comprised according to the invention are nucleic acid sequences which comprise so-called silent mutations or are modified in accordance with the codon usage of a specific original or host organism compared with a specifically mentioned sequence, as well as naturally occurring variants such as, for example, splice variants or allelic variants, thereof.

A "functionally equivalent fragment" means for expression units fragments which have substantially the same or a higher specific expression activity than the starting sequence.

"Essentially identical" means a specific expression activity which displays at least 50%, preferably 60%, more preferably 70%, more preferably 80%, more preferably 90%, particularly preferably 95% of the specific expression activity of the starting sequence.

"Fragments" mean partial sequences of the expression units which are described by embodiment E), F) or G). These fragments preferably have more than 10, but more preferably more than 12, 15, 30, 50 or particularly preferably more than 150, connected nucleotides of the nucleic acid sequence SEQ. ID. NO. 1.

It is particularly preferred to use the nucleic acid sequence SEQ. ID. NO. 2 as expression unit, i.e. for expression of genes.

SEQ. ID. NO. 2 has been described without assignment of function in the Genbank entry AP005283. The invention therefore further relates to the novel expression units of the invention.

The invention relates in particular to an expression unit comprising a nucleic acid of the invention having promoter activity and additionally functionally linked a nucleic acid sequence which ensures the translation of ribonucleic acids.

The invention particularly preferably relates to an expression unit comprising

E) the nucleic acid sequence SEQ. ID. NO. 2 or

F) a sequence derived from this sequence by substitution, insertion or deletion of nucleotides and having an identity of at least 90% at the nucleic acid level with the sequence SEQ. ID. NO. 2, or G) a nucleic acid sequence which hybridizes with the nucleic acid sequence SEQ. ID. NO. 2 under stringent conditions, or H) functionally equivalent fragments of the sequences of E), F) or G), with the proviso that the nucleic acid having the sequence SEQ. ID. NO. 2 is excluded.

The expression units of the invention comprise one or more of the following genetic elements: a minus 10

("−10") sequence; a minus 35 ("−35") sequence; a transcription sequence start, an enhancer region; and an operator region.

These genetic elements are preferably specific for species of *corynebacteria*, especially for *Corynbacterium glutamicum.*

All the expression units which are mentioned above can additionally be prepared in a manner known per se by chemical synthesis from the nucleotide building blocks such as, for example, by fragment condensation of individual overlapping complementary nucleic acid building blocks of the double helix. The chemical synthesis of oligonucleotides can take place for example in known manner by the phosphoramidite method (Voet, Voet, 2nd edition, Wiley Press New York, pp. 896-897). Addition of synthetic oligonucleotides and filling in of gaps using the Klenow fragment of DNA polymerase and ligation reactions, and general cloning methods, are described in Sambrook et al. (1989), Molecular cloning: A laboratory manual, Cold Spring Harbor Laboratory Press.

The methods and techniques used for the inventions in this patent are known to the skilled worker trained in microbiological and recombinant DNA techniques. Methods and techniques for growing bacterial cells, inserting isolated DNA molecules into the host cell, and isolating, cloning and sequencing isolated nucleic acid molecules etc. are examples of such techniques and methods. Those methods are described in many standard literature sources: Davis et al., Basic Methods In Molecular Biology (1986); J. H. Miller, Experiments in Molecular Genetics, Cold Spring Harbor Laboratory Press, Cold Spring Harbor, N.Y. (1972); J. H. Miller, A Short Course in Bacterial Genetics, Cold Spring Harbor Laboratory Press, Cold Spring Harbor, N.Y. (1992); M. Singer and P. Berg, Genes & Genomes, University Science Books, Mill Valley, Calif. (1991); J. Sambrook, E. F. Fritsch and T. Maniatis, Molecular Cloning: A Laboratory Manual, 2nd ed., Cold Spring Harbor Laboratory Press, Cold Spring Harbor, N.Y. (1989); P. B. Kaufmann et al., Handbook of Molecular and Cellular Methods in Biology and Medicine, CRC Press, Boca Raton, Fla. (1995); Methods in Plant Molecular Biology and Biotechnology, B. R. Glick and J. E. Thompson, eds., CRC Press, Boca Raton, Fla. (1993); and P. F. Smith-Keary, Molecular Genetics of *Escherichia coli*, The Guilford Press, New York, N.Y. (1989).

All nucleic acid molecules of the present invention are preferably in the form of an isolated nucleic acid molecule. An "isolated" nucleic acid molecule is separated from other nucleic acid molecules which are present in the natural source of the nucleic acid, and may additionally be substantially free of other cellular material or culture medium if it is prepared by recombinant techniques, or free of chemical precursors or other chemicals if it is chemically synthesized.

The invention additionally includes the nucleic acid molecules complementary to the specifically described nucleotide sequences, or a section thereof.

The promoters and/or expression units of the invention can for example be used particularly advantageously in improved methods for the preparation of biosynthetic products by fermentation as described hereinafter.

The promoters and/or expression units of the invention have in particular the advantage that they are induced in microorganisms by stress. It is possible by suitable control of the fermentation process to control this stress induction specifically for an increase in the transcription/expression rate of desired genes. In the production of L-lysine in particular, this stress phase is reached very early, so that in this case an increased transcription/expression rate of desired genes can be achieved very early.

The nucleic acids of the invention having promoter activity can be used to alter, i.e. to increase or reduce, or to cause the transcription rate of genes in microorganisms compared with the wild type The expression units of the invention can be used to alter, i.e., to increase or reduce, or to cause the expression rate of genes in microorganisms compared with the wild type.

The nucleic acids of the invention having promoter activity and the expression units of the invention can also serve to regulate and enhance the production of various biosynthetic products such as, for example, fine chemicals, proteins, in particular amino acids, microorganisms, in particular in *Corynebacterium* species.

The invention therefore relates to a method for altering or causing the transcription rate of genes in microorganisms compared with the wild type by a) altering the specific promoter activity in the microorganism of endogenous nucleic acids of the invention having promoter activity, which regulate the transcription of endogenous genes, compared with the wild type or b) regulating transcription of genes in the microorganism by nucleic acids of the invention having promoter activity or by nucleic acids with altered specific promoter activity according to embodiment a), where the genes are heterologous in relation to the nucleic acids having promoter activity.

According to embodiment a), the alteration or causing of the transcription rate of genes in the microorganism compared with the wild type can take place by altering, i.e. increasing or reducing, the specific promoter activity in the microorganism. This can take place for example by targeted mutation of the nucleic acid sequence of the invention having promoter activity, i.e. by targeted substitution, deletion or insertion of nucleotides. An increased or reduced promoter activity can be achieved by replacing nucleotides in the RNA polymerase holoenzyme binding sites (known to the skilled worker also as −10 region and −35 region). Additionally by reducing or enlarging the distance of the described RNA polymerase holoenzyme binding sites from one another by deleting nucleotides or inserting nucleotides. Additionally by putting binding sites (also known to the skilled worker as operators) for regulatory proteins (known to the skilled worker as repressors and activators) in the spatial vicinity of the binding sites of the RNA polymerase holoenzyme so that, after binding to a promoter sequence, these regulators diminish or enhance the binding and transcription activity of the RNA polymerase holoenzyme, or else place it under a new regulatory influence.

The nucleic acid sequence SEQ. ID. NO. 53 preferably represents the ribosome binding site of the expression units of the invention, and the sequence SEQ. ID. NOD 52 represents the −10 region of the expression units of the invention. Alterations in the nucleic acid sequence in these regions lead to an alteration in the specific expression activity.

The invention therefore relates to the use of the nucleic acid sequence SEQ. ID. NO. 53 as ribosome binding site in expression units which enable genes to be expressed in bacteria of the genus *Corynebacterium* or *Brevibacterium.*

The invention further relates to the use of the nucleic acid sequence SEQ. ID. NO. 52 as −10 region in expression units which enable genes to be expressed in bacteria of the genus *Corynebacterium* or *Brevibacterium.*

The invention relates in particular to an expression unit which enables genes to be expressed in bacteria of the genus *Corynebacterium* or *Brevibacterium*, comprising the nucleic acid sequence SEQ. ID. NO. 53. In this case, the nucleic acid sequence SEQ. ID. NO. 53 is preferably used as ribosome binding site.

The invention further relates to an expression unit which enables genes to be expressed in bacteria of the genus *Corynebacterium* or *Brevibacterium*, comprising the nucleic acid sequence SEQ. ID. NO. 52. In this case, the nucleic acid sequence SEQ. ID. NO 52 is preferably used as −10 region.

In relation to the "specific promoter activity", an increase or reduction compared with the wild type means an increase or reduction in the specific activity compared with the nucleic acid of the invention having promoter activity of the wild type, i.e. for example compared with SEQ. ID. NO. 1.

According to embodiment b), the alteration or causing of the transcription rate of genes in microorganisms compared with the wild type can take place by regulating the transcription of genes in the microorganism by nucleic acids of the invention having promoter activity or by nucleic acids with altered specific promoter activity according to embodiment a), where the genes are heterologous in relation to the nucleic acids having promoter activity.

This is preferably achieved by b1) introducing one or more nucleic acids of the invention having promoter activity, where appropriate with altered specific promoter activity, into the genome of the microorganism so that transcription of one or more endogenous genes takes place under the control of the introduced nucleic acid having promoter activity, where appropriate with altered specific promoter activity, or b2) introducing one or more genes into the genome of the microorganism so that transcription of one or more of the introduced genes takes place under the control of the endogenous nucleic acids of the invention having promoter activity, where appropriate with altered specific promoter activity, or b3) introducing one or more nucleic acid constructs comprising a nucleic acid of the invention having promoter activity, where appropriate with altered specific promoter activity, and functionally linked one or more nucleic acids to be transcribed, into the microorganism.

It is thus possible to alter, i.e. to increase or to reduce, the transcription rate of an endogenous gene of the wild type by according to embodiment b1), introducing one or more nucleic acids of the invention having promoter activity where appropriate with altered specific promoter activity, into the genome of the microorganism so that transcription of one or more endogenous genes takes place under the control of the introduced nucleic acid having promoter activity, where appropriate with altered specific promoter activity, or according to embodiment b2), introducing one or more endogenous genes into the genome of the microorganism so that transcription of one or more of the introduced endogenous genes takes place under the control of the endogenous nucleic acids of the invention having promoter activity, where appropriate with altered specific promoter activity, or according to embodiment b3), introducing one or more nucleic acid constructs comprising a nucleic acid of the invention having promoter activity, where appropriate with altered specific promoter activity, and functionally linked one or more endogenous nucleic acids to be transcribed, into the microorganism.

It is thus further possible to cause the transcription rate of an exogenous gene compared with the wild typo by according to embodiment b2), introducing one or more endogenous genes into the genome of the microorganism so that transcription of one or more of the introduced exogenous genes takes place under the control of the endogenous nucleic acids of the invention having promoter activity, where appropriate with altered specific promoter activity, or according to embodiment b3), introducing one or more nucleic acid constructs comprising a nucleic acid of the invention having promoter activity, where appropriate with altered specific promoter activity, and functionally linked one or more exogenous nucleic acids to be transcribed, into the microorganism.

The insertion of genes according to embodiment b2) can moreover take place by integrating a gene into coding regions or noncoding regions. Insertion preferably takes place into noncoding regions.

Insertion of nucleic acid constructs according to embodiment b3) may moreover take place chromosomally or extrachromosomally. There is preferably chromosomal insertion of the nucleic acid constructs. A "chromosomal" integration is the insertion of an exogenous DNA fragment into the chromosome of a host cell. This term is also used for homologous recombination between an exogenous DNA fragment and the appropriate region on the chromosome of the host cell.

In embodiment b) there is preferably also use of nucleic acids of the invention with altered specific promoter activity in accordance with embodiment a). In embodiment b), as described in embodiment a), these may be present or be prepared in the microorganism, or be introduced in isolated form into the microorganism.

"Endogenous" means genetic information, such as, for example, genes, which is already present in the wild-type genome.

"Exogenous" means genetic information, such as, for example, genes, which is not present in the wild-type genome.

The term "genes" in relation to regulation of transcription by the nucleic acids of the invention having promoter activity preferably means nucleic acids which comprise a region to be transcribed, i.e. for example a region which regulates the translation, and a coding region and, where appropriate, further regulatory elements such as, for example, a terminator.

The term "genes" in relation to the regulation, described hereinafter, of expression by the expression units of the invention preferably means nucleic acids which comprise a coding region and, where appropriate, further regulatory elements such as, for example, a terminator.

A "coding region" means a nucleic acid sequence which encodes a protein.

"Heterologous" in relation to nucleic acids having promoter activity and genes means that the genes used are not in the wild type transcribed under the regulation of the nucleic acids of the invention having promoter activity, but that a new functional linkage which does not occur in the wild type is produced, and the functional combination of nucleic acid of the invention having promoter activity and specific gene does not occur in the wild type.

"Heterologous" in relation to expression units and genes means that the genes used are not in the wild type expressed under the regulation of the expression units of the invention having promoter activity, but that a new functional linkage which does not occur in the wild type is produced, and the functional combination of expression unit of the invention and specific gene does not occur in the wild type.

The invention further relates in a preferred embodiment to a method for increasing or causing the transcription rate of genes in microorganisms compared with the wild type by ah) increasing the specific promoter activity in the microorganism of endogenous nucleic acids of the invention having promoter activity, which regulate the transcription of endogenous genes, compared with the wild type, or bh) regulating the transcription of genes in the microorganism by nucleic acids of the invention having promoter activity or by nucleic acids with increased specific promoter activity according to embodiment a), where the genes are heterologous in relation to the nucleic acids having promoter activity.

The regulation of the transcription of genes in the microorganism by nucleic acids of the invention having promoter activity or by nucleic acids of the invention with increased specific promoter activity according to embodiment ah) is preferably achieved by bh1) introducing one or more nucleic acids of the invention having promoter activity, where appropriate with increased specific promoter activity, into the genome of the microorganism so that transcription of one or more endogenous genes takes place under the control of the introduced nucleic acid of the invention having promoter activity, where appropriate with increased specific promoter activity, or bh2) introducing one or more genes into the genome of the microorganism so that transcription of one or more of the Introduced genes takes place under the control of the endogenous nucleic acids of the invention having promoter activity, where appropriate with increased specific promoter activity, or bh3) introducing one or more nucleic acid constructs comprising a nucleic acid of the invention having promoter activity, where appropriate with increased specific promoter activity, and functionally linked one or more nucleic acids to be transcribed, into the microorganism.

The invention further relates in a preferred embodiment to a method for reducing the transcription rate of genes in microorganisms compared with the wild type by ar) reducing the specific promoter activity in the microorganism of endogenous nucleic acids of the invention having promoter activity, which regulate the transcription of the endogenous genes, compared with the wild type, or br) introducing nucleic acids with reduced specific promoter activity according to embodiment a) into the genome of the microorganism so that transcription of endogenous genes takes place under the control of the introduced nucleic acid with reduced promoter activity.

The invention further relates to a method for altering or causing the expression rate of a gene in microorganisms compared with the wild type by c) altering the specific expression activity in the microorganism of endogenous expression units of the invention, which regulate the expression of the endogenous genes, compared with the wild type, or d) regulating the expression of genes in the microorganism by expression units of the invention or by expression units of the invention with altered specific expression activity according to embodiment c), where the genes are heterologous in relation to the expression units.

According to embodiment c), the alteration or causing of the expression rate of genes in microorganisms compared with the wild type can take place by altering, i.e. increasing or reducing, the specific expression activity in the microorganism. This can take place for example by targeted mutation of the nucleic acid sequence of the invention having promoter activity, i.e. by targeted substitution deletion or insertion of nucleotides. For example, extending the distance between Shine-Dalgarno sequence and the translation start codon usually leads to a change, a diminution or else an enhancement of the specific expression activity. An alteration of the specific expression activity can also be achieved by either shortening or extending the distance of the sequence of the Shine-Dalgarno region (ribosome binding site) from the translation start codon through deletions or insertions of nucleotides. But also by altering the sequence of the Shine-Dalgarno region in such a way that the homology to complementary 3' side 16S rRNA is either enhanced or else diminished.

In relation to the "specific expression activity", an increase or reduction compared with the wild type means an increase or reduction of the specific activity compared with the expression unit of the invention of the wild type, i.e. for example compared with SEQ. ID. NO. 2.

According to embodiment d), the alteration or causing of the expression rate of genes in microorganisms compared with the wild type can take place by regulating the expression of genes in the microorganism by expression units of the invention or by expression units of the invention with altered specific expression activity according to embodiment c), where the genes are heterologous in relation to the expression units.

This is preferably achieved by d1) introducing one or more expression units of the invention, where appropriate with altered specific expression activity, into the genome of the microorganism so that expression of one or more endogenous genes takes place under the control of the introduced expression units, or d2) introducing one or more genes into the genome of the microorganism so that expression of one or more of the introduced genes takes place under the control of the endogenous expression units of the invention, where appropriate with altered specific expression activity, or d3) introducing one or more nucleic acid constructs comprising an expression unit of the invention, where appropriate with altered specific expression activity, and functionally linked one or more nucleic acids to be expressed, into the microorganism.

It is thus possible to alter, i.e. to increase or to reduce, the expression rate of an endogenous gene of the wild type by according to embodiment d1) introducing one or more expression units of the invention, where appropriate with altered specific expression activity, into the genome of the microorganism so that expression of one or more endogenous genes takes place under the control of the introduced expression units, or according to embodiment d2) introducing one or more genes into the genome of the microorganism so that expression of one or more of the introduced genes takes place under the control of the endogenous expression units of the invention, where appropriate with altered specific expression activity, or according to embodiment d3) introducing one or more nucleic acid constructs comprising an expression unit of the invention, where appropriate with altered specific expression activity, and functionally linked one or more nucleic acids to be expressed, into the microorganism.

It is thus further possible to cause the expression rate of an endogenous gene compared with the wild type by according to embodiment d2) introducing one or more exogenous genes into the genome of the microorganism so that expression of one or more of the introduced genes takes place under the control of the endogenous expression units of the invention, where appropriate with altered specific expression activity, or according to embodiment d3) introducing one or more nucleic acid constructs comprising an expression unit of the invention, where appropriate with altered specific expression activity, and functionally linked one or more exogenous nucleic acids to be expressed, into the microorganism.

The insertion of genes according to embodiment d2) can moreover take place by integrating a gene into coding regions or noncoding regions. Insertion preferably takes place into noncoding regions.

Insertion of nucleic acid constructs according to embodiment d3) may moreover take place chromosomally or extrachromosomally. There is preferably chromosomal insertion of the nucleic acid constructs.

The nucleic acid constructs are also referred to hereinafter as expression cassettes In embodiment d) there is preferably also use of expression units of the invention with altered specific expression activity in accordance with embodiment c). In embodiment d), as described in embodiment c), these may be present or be prepared in the microorganism, or be introduced in isolated form into the microorganism.

The invention further relates in a preferred embodiment to a method for increasing or causing the expression rate of a gene in microorganisms compared with the wild type by ch) increasing the specific expression activity in the microorganism of endogenous expression units of the invention, which regulate the expression of the endogenous genes, compared with the wild type, or dh) regulating the expression of genes in the microorganism by expression units of the invention or by expression units with increased specific expression activity according to embodiment a), where the genes are heterologous in relation to the expression units.

The regulation of the expression of genes in the microorganism by expression units of the invention or by expression units with increased specific expression activity according to embodiment c) is preferably achieved by dh1) introducing one or more expression units of the invention, where appropriate with increased specific expression activity, into the genome of the microorganism so that expression of one or more endogenous genes takes place under the control of the introduced expression units, where appropriate with increased specific expression activity, or dh2) introducing one or more genes into the genome of the microorganism so that expression of one or more of the introduced genes takes place under the control of the endogenous expression units of the invention, where appropriate with increased specific expression activity, or dh3) introducing one or more nucleic acid constructs comprising an expression unit of the invention, where appropriate with increased specific expression activity, and functionally linked one or more nucleic acids to be expressed, into the microorganism.

The invention further relates to a method for reducing the expression rate of genes in microorganisms compared with the wild type by cr) reducing the specific expression activity in the microorganism of endogenous expression units of the invention, which regulate the expression of the endogenous genes, compared with the wild type, or dr) introducing expression units with reduced specific expression activity according to embodiment cr) into the genome of the microorganism so that expression of endogenous genes takes place under the control of the introduced expression units with reduced expression activity.

In a preferred embodiment of the methods of the invention described above for altering or causing the transcription rate and/or expression rate of genes in microorganisms, the genes are selected from the group of nucleic acids encoding a protein from the biosynthetic pathway of fine chemicals, where the genes may optionally comprise further regulatory elements.

In a particularly preferred embodiment of the methods of the invention described above for altering or causing the transcription rate and/or expression rate of genes in microorganisms, the genes are selected from the group of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors and nucleic acids encoding a protein from the biosynthetic pathway of enzymes, where the genes may optionally comprise further regulatory elements.

In a particularly preferred embodiment, the proteins from the biosynthetic pathway of amino acids are selected from the group of aspartate kinase, aspartate-semialdehyde, dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II coenzyme B12-dependent methionine synthase, coenzyme B12-independent methionine synthase activity, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1, 6-bisphosphatase, protein of sulfate reduction RXA077, protein of sulfate reduction RXA248, protein of sulfate reduction RXA247, protein OpcA, 1-phosphofructokinase and 6-phosphofructokinase.

Preferred proteins and nucleic acids encoding these proteins of the proteins described above from the biosynthetic pathway of amino acids are respectively protein sequences and nucleic acid sequences of microbial origin, preferably from bacteria of the genus *Corynebacterium* or *Brevibacterium*, preferably from coryneform bacteria, particularly preferably from *Corynebacterium glutamicum.*

Examples of particularly preferred protein sequences and the corresponding nucleic acid sequences encoding these proteins from the biosynthetic pathway of amino acids, the document referring thereto, and the designation thereof in the referring document are listed in Table 1

TABLE 1

| Protein | Nucleic acid encoding protein | Referring document | SEQ. ID. NO, in referring document |
|---|---|---|---|
| Aspartate kinase | ask or lysC | EP1106790 | DNA: 281 Protein: 3781 |
| Aspartate-semialdehyde dehydrogenase | asd | EP1108790 | DNA: 331 Protein: 3831 |
| Dihydrodipicolinate synthetase | dapA | WO 0100843 | DNA: 55 Protein: 56 |
| Dihydrodipicolinate reductase | dapB | WO 0100843 | DNA: 35 Protein: 36 |
| meso-Diaminopimelate D-dehydrogenase | ddh | EP1108790 | DNA: 3494 Protein: 6944 |
| Diaminopicolinate decarboxylase | lysA | EP1108790 | DNA: 3451 Prot.: 6951 |
| Lysine exporter | lysE | EP1108790 | DNA: 3455 Prot.: 6955 |
| Arginyl-tRNA synthetase | argS | EP1108790 | DNA: 3450 Prot.: 6950 |
| Glucose-6-phosphate dehydrognease | zwf | WO 0100844 | DNA: 243 Prot.: 244 |
| Glyceraldehyde-3-phosphate dehydrogenase | gap | WO 0100844 | DNA: 187 Prot.: 188 |
| 3-Phosphoglycerate kinase | pgk | WO 0100844 | DNA: 69 Prot.: 70 |
| Pyruvate carboxylase | pycA | EP1108790 | DNA: 765 Prot.: 4265 |
| Triosephosphate isomerase | tpi | WO 0100844 | DNA: 61 Prot.: 62 |
| Biotin ligase | birA | EP1108790 | DNA: 786 Prot: 4286 |
| PEP carboxylase | pck | EP1108790 | DNA: 3470 Prot.: 6970 |
| Homoserine kinase | thrB | WO 0100843 | DNA: 173 Prot.: 174 |
| Threonine synthase | thrC | WO 0100843 | DNA: 175 Prot.: 176 |
| Threonine export carrier | thrE | WO 0251231 | DNA: 41 Prot.: 42 |
| Threonine efflux protein | RXA2390 | WO 0100843 | DNA: 7 Prot.: 8 |
| Threonine dehydratase | ilvA | EP 1108790 | DNA: 2328 Prot.: 5828 |
| Homoserine O-acetyltransferase | metA | EP 1108790 | DNA: 727 Prot: 4227 |
| Cystathionine gamma-synthase | metB | EP 1108790 | DNA: 3491 Prot: 6991 |
| Cystathionine beta-lyase | metC | EP 1108790 | DNA: 2535 Prot: 6035 |
| Coenzyme B12-dependent methionine synthase, - | metH | EP 1108790 | DNA: 1663 Prot: 5163 |
| O-Acetylhomoserine sulfhydrylase | metY | EP 1108790 | DNA: 726 Prot: 4226 |

TABLE 1-continued

| Protein | Nucleic acid encoding protein | Referring document | SEQ. ID. NO, in referring document |
|---|---|---|---|
| Methylenetetrahydrofolate reductase | metF | EP 1108790 | DNA: 2379 Prot: 5879 |
| D-3-Phosphoglycerate dehydrogenase | serA | EP 1108790 | DNA: 1415 Prot: 4915 |
| Phosphoserine phosphatase 1 | serB | WO 0100843 | DNA: 153 Prot.: 154 |
| Phosphoserine phosphatase 2 | serB | EP 1108790 | DNA: 467 Prot: 3967 |
| Phosphoserine phosphatase 3 | serB | EP 1108790 | DNA: 334 Prot.: 3834 |
| Phosphoserine aminotransferase | serC | WO 0100843 | DNA: 151 Prot.: 152 |
| Serine acetyltransferase | cysE | WO 0100843 | DNA: 243 Prot.: 244 |
| Cysteine synthase I | cysK | EP 1108790 | DNA: 2817 Prot.: 6317 |
| Cysteine synthase II | CysM | EP 1108790 | DNA: 2338 Prot.: 5838 |
| Homoserine dehydrogenase | hom | EP 1108790 | DNA: 3452 Prot.: 6952 |
| Coenzyme B12-independent methionine synthase | metE | WO 0100843 | DNA: 755 Prot.: 756 |
| Serine hydroxymethyltransferase | glyA | WO 0100843 | DNA: 143 Prot.: 144 |
| Protein in sulfate reduction | RXA247 | EP 1108790 | DNA: 3089 Prot.: 6589 |
| Protein in sulfate reduction | RXA248 | EP 1108790 | DNA: 3090 Prot.: 6590 |
| Sulfate adenylyltransferase subunit 1 | CysN | EP 1108790 | DNA: 3092 Prot.: 6592 |
| Sulfate adenylyltransferase subunit 2 | CysD | EP 1108790 | DNA: 3093 Prot.: 6593 |
| Phosphoadenosine-phosphosulfate reductase | CysH | WO 02729029 | DNA: 7 Prot.: 8 |
| Ferredoxin-sulfite reductase | RXA073 | WO 0100842 | DNA: 329 Prot.: 330 |
| Ferredoxin NADP-reductase | RXA076 | WO 0100843 | DNA: 79 Prot.: 80 |
| Transcriptional regulator LuxR | luxR | WO 0100842 | DNA: 297 Protein: 298 |
| Transcriptional regulator LysR1 | lysR1 | EP 1108790 | DNA: 676 Protein: 4176 |
| Transcriptional regulator LysR2 | lysR2 | EP 1108790 | DNA: 3228 Protein: 6728 |
| Transcriptional regulator LysR3 | lysRS | EP 1108790 | DNA: 2200 Protein: 5700 |
| Malate-quinone oxidoreductase | mqo | WO 0100844 | DNA: 569 Protein: 570 |
| Transketolase | RXA2739 | EP 1108790 | DNA: 1740 Prot: 5240 |
| Transaldolase | RXA2738 | WO 0100844 | DNA: 245 Prot: 246 |
| OpcA | opcA | WO 0100804 | DNA: 79 Prot: 80 |
| 1-Phosphofructo-kinase 1 | pfk1 | WO0100844 | DNA: 55 Protein: 56 |
| 1-Phosphofructo-kinase 2 | pfk2 | WO0100844 | DNA: 57 Protein: 58 |
| 6-Phosphofructo-kinase 1 | 6-pfk1 | EP 1108790 | DNA: 1383 Protein: 4883 |
| 6-Phosphofructo-kinase 2 | 6-pfk2 | DE 10112992 | DNA: 1 Protein: 2 |
| Fructose-1,6-bisphosphatase 1 | fbr1 | EP1108790 | DNA: 1136 Protein: 4636 |
| Pyruvate oxidase | poxB | WO 0100844 | DNA: 85 Protein: 86 |
| RXA00655 regulator | RXA655 | US2003162267.2 | DNA: 1 Prot.: 2 |
| RXN02910 regulator | RXN2910 | US2003162267.2 | DNA: 5 Prot.: 6 |
| 6-phosphoglucono-lactonase | RXA2735 | WO 0100844 | DNA: 1 Prot.: 2 |

A further example of a particularly preferred protein sequence and the corresponding nucleic acid sequence encoding this protein from the biosynthetic pathway of amino acids is the sequence of fructose-1,6-bisphosphatase 2, also called fbr2, (SEQ. ID. NO. 51) and the corresponding nucleic acid sequence encoding a fructose-1,6-bisphosphatase 2 (SEQ. ID. NO. 50).

A further example of a particularly preferred protein sequence and the corresponding nucleic acid sequence encoding this protein from the biosynthetic pathway of amino acids is the sequence of the protein in sulfate reduction, also called RXA077, (SEQ. ID. NO. 4) and the corresponding nucleic acid sequence encoding a protein in sulfate reduction (SEQ. ID. NO. 3).

Further particularly preferred protein sequences from the biosynthetic pathway of amino acids have in each case the amino acid sequence indicated in Table 1 for this protein, where the respective protein has, in at least one of the amino acid positions indicated in Table 2/column 2 for this amino acid sequence, a different proteinogenic amino acid than the respective amino acid indicated in Table 2/column 3 in the same fine. In a further preferred embodiment, the proteins have, in at least one of the amino acid positions indicated in Table 2/column 2 for the amino acid sequence, the amino acid indicated in Table 2/column 4 in the same line. The proteins indicated in Table 2 are mutated proteins of the biosynthetic pathway of amino acids which have particularly advantageous properties and are therefore particularly suitable for expressing the corresponding nucleic acids through the promoter of the invention and for producing amino acids. For example, the mutation T311I leads to the feedback inhibition of ask being switched off.

The corresponding nucleic acids which encode a mutated protein described above from Table 2 can be prepared by conventional methods.

A suitable starting point for preparing the nucleic acid sequences encoding a mutated protein is, for example, the genome of a *Corynebacterium glutamicum* strain which is obtainable from the American Type Culture Collection under the designation ATCC 13032, or the nucleic acid sequences referred to in Table 1. For the back-translation of the amino acid sequence of the mutated proteins into the nucleic acid sequences encoding these proteins, it is advantageous to use the codon usage of the organism into which the nucleic acid sequence is to be introduced or in which the nucleic acid sequence is present. For example, it is advantageous to use the codon usage of *Corynebacterium* glutamicum for *Corynebacterium glutamicum*. The codon usage of the particular organism can be ascertained in a manner known per se from databases or patent applications which describe at least one protein and one gene which encodes this protein from the desired organism.

The information in Table 2 is to be understood in the following way:

In column 1 "identification", an unambiguous designation for each sequence in relation to Table 1 is indicated.

In column 2 "AA-POS", the respective number refers to the amino acid position of the corresponding polypeptide sequence from Table 1. A "26" in the column "AA-PO S" accordingly means amino acid position 26 of the correspondingly indicated polypeptide sequence. The numbering of the position starts at +1 at the N terminus.

In column 3 "AA wild type", the respective letter designates the amino acid—represented in one-letter code—at the position indicated in column 2 in the corresponding wild-type strain of the sequence from Table 1.

In column 4 "AA mutant", the respective letter designates the amino acid—represented in one-letter code—at the position indicated in column 2 in the corresponding mutant strain.

In column 5 "function", the physiological function of the corresponding polypeptide sequence is indicated.

For mutated protein with a particular function (column 5) and a particular initial amino acid sequence (Table 1), columns 2, 3 and 4 describe at least one mutation, and a plurality of mutations for some sequences. This plurality of mutations always refers to the closest initial amino acid sequence above in each case (Table 1). The term "at least one of the amino acid positions" of a particular amino acid sequence preferably means at least one of the mutations described for this amino acid sequence in columns 2, 3 and 4.

One-letter code for proteinogenic amino acids:

A alanine
C cysteine
D aspartate
E glutamate
F phenylalanine
G glycine
H histidine
I isoleucine
K lysine
L leucine
M methionine
N asparagine
P proline
Q glutamine
R arginine
S serine
T threonine
V valine
W tryptophan
Y tyrosine

TABLE 2

| Column 1 Identification | Column 2 AA position | Column 3 AA wild type | Column 4 AA mutant | Column 5 Function |
|---|---|---|---|---|
| ask | 317 | S | A | aspartate kinase |
| | 311 | T | I | |
| | 279 | A | T | |
| asd | 66 | D | G | asparate-semialdehyde dehydrogenase |
| | 234 | R | H | |
| | 272 | D | E | |
| | 285 | K | E | |
| | 20 | L | F | |
| dapA | 2 | S | A | dihydrodipicolinate synthetase |
| | 84 | K | N | |
| | 85 | L | V | |
| dapB | 91 | D | A | dihydrodipicolinate reductase |
| | 83 | D | N | |
| ddh | 174 | D | E | meso-diaminopimelate D-dehydrogenase |
| | 235 | F | L | |
| | 237 | S | A | |
| lysA | 265 | A | D | diaminopicolinate decarboxylase |
| | 320 | D | N | |
| | 332 | I | V | |
| argS | 355 | G | D | arginyl-tRNA synthetase |
| | 156 | A | S | |
| | 513 | V | A | |
| | 540 | H | R | |
| zwt | 8 | S | T | glucose-6-phosphate dehydrogenase |
| | 150 | T | A | |
| | 321 | G | S | |

TABLE 2-continued

| Column 1 Identification | Column 2 AA position | Column 3 AA wild type | Column 4 AA mutant | Column 5 Function |
|---|---|---|---|---|
| gap | 264 | G | S | glyceraldehyde-3-phosphate dehydrogenase |
| pycA | 7 | S | L | pyruvate carboxylase |
| | 153 | E | D | |
| | 182 | A | S | |
| | 206 | A | S | |
| | 227 | H | R | |
| | 455 | A | G | |
| | 458 | P | S | |
| | 639 | S | T | |
| | 1008 | R | H | |
| | 1059 | S | P | |
| | 1120 | D | E | |
| pck | 162 | H | Y | PEP carboxylase |
| | 241 | G | D | |
| | 829 | T | R | |
| thrB | 103 | S | A | homoserine kinase |
| | 190 | T | A | |
| | 133 | A | V | |
| | 138 | P | S | |
| thrC | 69 | G | R | threonine synthase |
| | 478 | T | I | |
| RXA330 | 85 | I | M | threonine efflux protein |
| | 161 | F | I | |
| | 195 | G | D | |
| hom | 104 | V | I | homoserine dehydrogenase |
| | 116 | T | I | |
| | 148 | G | A | |
| | 59 | V | A | |
| | 270 | T | S | |
| | 345 | R | P | |
| | 268 | K | N | |
| | 61 | D | H | |
| | 72 | E | Q | |
| lysR1 | 80 | R | H | transcriptional regulator LysR1 |
| lysR3 | 142 | R | W | transcriptional regulator LysR3 |
| | 179 | A | T | |
| RXA2739 | 75 | N | D | transketolase |
| | 329 | A | T | |
| | 332 | A | T | |
| | 556 | V | I | |
| RXA2738 | 242 | K | M | transaldolase |
| opcA | 107 | Y | H | OpcA |
| | 219 | K | N | |
| | 233 | P | S | |
| | 261 | Y | H | |
| | 312 | S | F | |
| | 65 | G | R | aspartate-1-decarboxylase |
| | 33 | G | S | 6-phosphoglucono-lactonase |

In the methods of the invention described above for altering or causing the transcription rate and/or expression rate of genes in microorganisms, and the methods described hereinafter for producing genetically modified microorganisms, the genetically modified microorganisms described hereinafter and the methods described hereinafter for producing biosynthetic products, the introduction of the nucleic acids of the invention having promoter activity, of the expression units of the invention, of the genes described above and of the nucleic acid constructs or expression cassettes described above into the microorganism, in particular into coryneform bacteria, preferably takes place by the SacB method.

The SacB method is known to the skilled worker and described for example in Schafer A, Tauch A, Jäger W, Kalinowski J, Thierbach G, Pühler A.; Small mobilizable multi-purpose cloning vectors derived from the *Escherichia coli* plasmids pK18 and pK19: selection of defined deletions in the chromosome of *Corynebacterium glutamicum*, Gene. 1994 Jul. 22; 145(1):69-73 and Blomfield I C, Vaughn V, Rest R F, Eisenstein B I.; Allelic exchange in *Escherichia coli* using the *Bacillus subtilis* sacB gene and a temperature-sensitive pSC101 replicon; Mol. Microbiol. 1991 June; 5(6): 1447-57.

In a preferred embodiment of the methods of the invention described above, the alteration or causing of the transcription rate and/or expression rate of genes in microorganisms takes place by introducing nucleic acids of the invention having promoter activity or expression units of the invention into the microorganism.

In a further preferred embodiment of the methods of the invention described above, the alteration or causing of the transcription rate and/or expression rate of genes in microorganisms takes place by introducing the nucleic acid constructs or expression cassettes described above into the microorganism.

The invention therefore also relates to an expression cassette comprising at least one expression unit of the invention at least one further nucleic acid sequence to be expressed, i.e. a gene to be expressed and where appropriate further genetic control elements such as, for example, a terminator, where at least one expression unit and a further nucleic acid sequence to be expressed are functionally linked together, and the further nucleic acid sequence to be expressed is heterologous in relation to the expression unit.

The nucleic acid sequence to be expressed is preferably at least one nucleic acid encoding a protein from the biosynthesis pathway of fine chemicals.

The nucleic acid sequence to be expressed is particularly preferably selected from the group of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors and nucleic acids encoding a protein from the biosynthetic pathway of enzymes.

Preferred proteins from the biosynthetic pathway of amino acids are described above and examples thereof are described in Tables 1 and 2.

The physical location of the expression unit relative to the gene to be expressed in the expression cassettes of the invention is chosen so that the expression unit regulates the transcription and preferably also the translation of the gene to be expressed, and thus enables one or more proteins to be produced. "Enabling production" includes in this connection a constitutive increase in the production, diminution or blocking of production under specific conditions and/or increasing the production under specific conditions. The "conditions" comprise in this connection: (1) addition of a component to the culture medium, (2) removal of a component from the culture medium, (3) replacement of one component in the culture medium by a second component, (4) increasing the temperature of the culture medium, (5) reducing the temperature of the culture medium, and (6) regulating the atmospheric conditions such as, for example, the oxygen or nitrogen concentration in which the culture medium is kept.

The invention further relates to an expression vector comprising an expression cassette of the invention described above.

Vectors are well known to the skilled worker and can be found in "Cloning Vectors" (Pouwels P H et al., editors, Elsevier, Amsterdam-New York-Oxford, 1985). Apart from plasmids, vectors also mean all other vectors known to the skilled worker, such as, for example, phages, transposons, IS elements, phasmids, cosmids, and linear or circular DNA. These vectors may undergo autonomous replication in the host organism or chromosomal replication.

Suitable and particularly preferred plasmids are those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107: 69-0074 (1991)) are based on the cryptic plasmids pHM1519, pBL1 or pGA1. Other plasmid vectors such as, for example, pCLiK5MCS, or those based on pCG4 (U.S. Pat. No. 4,469,160) or pNG2 (Serwold-Davis et al., FEMS Microbiology Letters 66, 119-124 (1990)) or pAG1 (U.S. Pat. No. 5,158,891), can be used in the same way.

Also suitable are those plasmid vectors with the aid of which the method of gene amplification by integration into the chromosome can be used, as described for example by Reinscheid et al. (Applied and Environmental Microbiology 60, 126-132 (1994)) for the duplication and amplification of the hom-thrB operon. In this method the complete gene is cloned into a plasmid vector which is able to replicate in a host (typically *E. coli*) but not in *C. glutamicum*. Examples of suitable vectors are pSUP301 (Simon et al., Bio/Technology 1, 784-791 (1983)), pK18mob or pK19mob (Schäfer et al., Gene 145, 69-73 (1994)), Bernard et al., Journal of Molecular Biology, 234: 534-541 (1993)), pEM1 (Schrumpf et al. 1991, Journal of Bacteriology 173: 4510-4516) or pBGS8 (Spratt et al., 1986, Gene 41: 337-342). The plasmid vector which comprises the gene to be amplified is subsequently transferred by transformation into the desired strain of *C. glutamicum*. Methods for transformation are described for example in Thierbach et al. (Applied Microbiology and Biotechnology 29, 356-362 (1988)), Dunican and Shivnan (Biotechnology 7, 1067-1070 (1989)) and Tauch et al. (FEMS Microbiological Letters 123, 343-347 (1994)).

The invention further relates to a genetically modified microorganism where the genetic modification leads to an alteration or causing of the transcription rate of at least one gene compared with the wild type, and is dependent on a) altering the specific promoter activity in the microorganism of at least one endogenous nucleic acid having promoter activity according to claim 1, which regulates the transcription of at least one endogenous gene, or b) regulating the transcription of genes in the microorganism by nucleic acids having promoter activity according to claim 1 or by nucleic acids having promoter activity according to claim 1 with altered specific promoter activity according to embodiment a), where the genes are heterologous in relation to the nucleic acids having promoter activity, As described above for the methods, the regulation of the transcription of genes in the microorganism by nucleic acids having promoter activity according to claim 1 or by nucleic acids having promoter activity according to claim 1 with altered specific promoter activity according to embodiment a), is achieved by b1) introducing one or more nucleic acids having promoter activity according to claim 1, where appropriate with altered specific promoter activity, into the genome of the microorganism so that transcription of one or more endogenous genes takes place under the control of the introduced nucleic acid having promoter activity according to claim 1, where appropriate with altered specific promoter activity, or b2) introducing one or more genes into the genome of the microorganism so that transcription of one or more of the introduced genes takes place under the control of the endogenous nucleic acids having promoter activity according to claim 1, where appropriate with altered specific promoter activity, or b3) introducing one or more nucleic acid constructs comprising a nucleic acid having promoter activity according to claim 1, where appropriate with altered specific promoter activity, and functionally linked one or more nucleic acids to be transcribed, into the microorganism.

The invention further relates to a genetically modified microorganism having elevated or caused transcription rate of at least one gene compared with the wild type, where ah) the specific promoter activity in the microorganism of endogenous nucleic acids having promoter activity according to claim 1, which regulate the transcription of endogenous genes, is increased compared with the wild type, or bh) the transcription of genes in the microorganism is regulated by nucleic acids having promoter activity according to claim 1 or by nucleic acids having increased specific promoter activity according to embodiment ah), where the genes are heterologous in relation to the nucleic acids having promoter activity.

As described above for the methods, the regulation of the transcription of genes in the microorganism by nucleic acids having promoter activity according to claim 1 or by nucleic acids having promoter activity according to claim 1 with increased specific promoter activity according to embodiment a), is achieved by bh1) introducing one or more nucleic acids having promoter activity according to claim 1, where appropriate with increased specific promoter activity, into the genome of the microorganism so that transcription of one or more endogenous genes takes place under the control of the introduced nucleic acid having promoter activity, where appropriate with increased specific promoter activity, or bh2) introducing one or more genes into the genome of the microorganism so that transcription of one or more of the introduced genes takes place under the control of the endogenous nucleic acids having promoter activity according to claim 1, where appropriate with increased specific promoter activity, or bh3) introducing one or more nucleic acid constructs comprising a nucleic acid having promoter activity according to claim 1, where appropriate with increased specific promoter activity, and functionally linked one or more nucleic acids to be transcribed, into the microorganism.

The invention further relates to a genetically modified microorganism with reduced transcription rate of at least one gene compared with the wild type, where ar) the specific promoter activity in the microorganism of at least one endogenous nucleic acid having promoter activity according to claim 1, which regulates the transcription of at least one endogenous gene, is reduced compared with the wild type, or br) one or more nucleic acids having reduced promoter activity according to embodiment a) are introduced into the genome of the microorganism so that the transcription of at least one endogenous gene takes place under the control of the introduced nucleic acid having reduced promoter activity.

The invention further relates to a genetically modified microorganism, where the genetic modification leads to an alteration or causing of the expression rate of at least one gene compared with the wild type, and is dependent on c) altering the specific expression activity in the microorganism of at least one endogenous expression unit according to claim 2 or 3, which regulates the expression of at least one endogenous gene, compared with the wild type or d) regulating the expression of genes in the microorganism by expression units according to claim 2 or 3 or by expression units according to claim 2 or 3 with altered specific expression activity according to embodiment a), where the genes are heterologous in relation to the expression units.

As described above for the methods, the regulation of the expression of genes in the microorganism by expression units according to claim 2 or 3 or by expression units according to claim 2 or 3 with altered specific expression activity according to embodiment a) is achieved by d1) introducing one or more expression units according to claim 2 or 3, where appropriate with altered specific expression activity, into the genome of the microorganism so that expression of one or more endogenous genes takes place under the control of the introduced expression units according to claim 2 or 3, where appropriate with altered specific expression activity, or d2) introducing one or more genes into the genome of the microorganism so that expression of one or more of the introduced genes takes place under the control of the endogenous expression units according to claim 2 or 3, where appropriate with altered specific expression activity, or d3) introducing one or more nucleic acid constructs comprising an expression unit according to claim 2 or 3, where appropriate with altered specific expression activity, and functionally linked one or more nucleic acids to be expressed, into the microorganism.

The invention further relates to a genetically modified microorganism with increased or caused expression rate of at least one gene compared with the wild type, where ch) the specific expression activity in the microorganism of at least one endogenous expression unit according to claim 2 or 3, which regulates the expression of the endogenous genes, is increased compared with the wild type, or dh) the expression of genes in the microorganism is regulated by expression units according to claim 2 or 3 or by expression units according to claim 2 or 3 with increased specific expression activity according to embodiment a), where the genes are heterologous in relation to the expression units.

As described above for the methods, the regulation of the expression of genes in the microorganism by expression units according to claim 2 or 3 or by expression units according to claim 2 or 3 with increased specific expression activity according to embodiment a) is achieved by dh1) introducing one or more expression units according to claim 2 or 3, where appropriate with increased specific expression activity, into the genome of the microorganism so that expression of one or more endogenous genes takes place under the control of the introduced expression units according to claim 2 or 3, where appropriate with increased specific expression activity, or dh2) introducing one or more genes into the genome of the microorganism so that expression of one or more of the introduced genes takes place under the control of the endogenous expression units according to claim 2 or 3, where appropriate with increased specific expression activity, or dh3) introducing one or more nucleic acid constructs comprising an expression unit according to claim 2 or 3, where appropriate with increased specific expression activity, and functionally linked one or more nucleic acids to be expressed, into the microorganism.

The invention further relates to a genetically modified microorganism with reduced expression rate of at least one gene compared with the wild type, where cr) the specific expression activity in the microorganism of at least one endogenous expression unit according to claim 2 or 3, which regulates the expression of at least one endogenous gene, is reduced compared with the wild type, or dr) one or more expression units according to claim 2 or 3 with reduced expression activity are introduced into the genome of the microorganism so that expression of at least one endogenous gene takes place under the control of the introduced expression unit according to claim 2 or 3 with reduced expression activity.

The invention further relates to a genetically modified microorganism comprising an expression unit according to claim 2 or 3 and functionally linked a gene to be expressed, where the gene is heterologous in relation to the expression unit.

This genetically modified microorganism particularly preferably comprises an expression cassette of the invention.

The present invention particularly preferably relates to genetically modified microorganisms, in particular coryneform bacteria, which comprise a vector, in particular shuttle vector or plasmid vector, which harbors at least one recombinant nucleic acid construct as defined according to the invention.

In a preferred embodiment of the genetically modified microorganisms, the genes described above are at least one nucleic acid encoding a protein from the biosynthetic pathway of fine chemicals.

In a particularly preferred embodiment of the genetically modified microorganisms, the genes described above are selected from the group of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors and nucleic acids encoding a protein from the biosynthetic pathway of enzymes, where the genes may optionally comprise further regulatory elements.

Preferred proteins from the biosynthetic pathway of amino acids are selected from the group of aspartate kinase, aspartate-semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase activity, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1,6-bisphosphatase, protein of sulfate reduction RXA077, protein of sulfate reduction RXA248, protein of sulfate reduction RXA247, protein OpcA, 1-phosphofructokinase and 6-phosphofructokinase.

Particularly preferred examples of the proteins and genes from the biosynthetic pathway of amino acids are described above in Table 1 and Table 2.

Preferred microorganisms or genetically modified microorganisms are bacteria, algae, fungi or yeasts.

Particularly preferred microorganisms are, in particular, coryneform bacteria.

Preferred coryneform bacteria are bacteria of the genus *Corynebacterium*, in particular of the species *Corynebacterium glutamicum, Corynebacterium acetoglutamicum, Corynebacterium acetoacidophilum, Corynebacterium thermoaminogenes, Corynebacterium melassecola* and *Corynebacterium efficiens* or of the genus *Brevibacterium*, in particular of the species *Brevibacterium flavum, Brevibacterium lactofermentum* and *Brevibacterium divaricatum.*

Particularly preferred bacteria of the genera *Corynebacterium* and *Brevibacterium* are selected from the group of *Corynebacterium glutamicum* ATCC 13032, *Corynebacterium acetoglutamicum* ATCC 15806, *Corynebacterium acetoacidophilum* ATCC 13870, *Corynebacterium thermoaminogenes* FERM BP-1539, *Corynebacterium melassecola* ATCC 17965, *Corynebacterium efficiens DSM* 44547, *Corynebacterium* efficiens DSM 44548, *Corynebacterium efficiens* DSM 44549, *Brevibacterium flavum* ATCC 14067, *Brevibacterium lactofermentum* ATCC 13869, *Brevibacterium divaricatum* ATCC 14020, *Corynebacterium glutamicum* KFCC10065 and *Corynebacterium glutamicum* ATCC21608.

The abbreviation KFCC means the Korean Federation of Culture Collection, the abbreviation ATCC the American type strain culture collection and the abbreviation DSM the Deutsche Sammlung von Mikroorganismen.

Further particularly preferred bacteria of the genera *Corynebacterium* and *Brevibacterium* are listed in Table 3:

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| *Brevibacterium* | *ammoniagenes* | 21054 | | | | | | | |
| *Brevibacterium* | *ammoniagenes* | 19350 | | | | | | | |
| *Brevibacterium* | *ammoniagenes* | 19351 | | | | | | | |
| *Brevibacterium* | *ammoniagenes* | 19352 | | | | | | | |
| *Brevibacterium* | *ammoniagenes* | 19353 | | | | | | | |
| *Brevibacterium* | *ammoniagenes* | 19354 | | | | | | | |
| *Brevibacterium* | *ammoniagenes* | 19355 | | | | | | | |
| *Brevibacterium* | *ammoniagenes* | 19356 | | | | | | | |
| *Brevibacterium* | *ammoniagenes* | 21055 | | | | | | | |
| *Brevibacterium* | *ammoniagenes* | 21077 | | | | | | | |
| *Brevibacterium* | *ammoniagenes* | 21553 | | | | | | | |
| *Brevibacterium* | *ammoniagenes* | 21580 | | | | | | | |
| *Brevibacterium* | *ammoniagenes* | 39101 | | | | | | | |
| *Brevibacterium* | *butanicum* | 21196 | | | | | | | |
| *Brevibacterium* | *divaricatum* | 21792 | P928 | | | | | | |
| *Brevibacterium* | *flavum* | 21474 | | | | | | | |
| *Brevibacterium* | *flavum* | 21129 | | | | | | | |
| *Brevibacterium* | *flavum* | 21518 | | | | | | | |
| *Brevibacterium* | *flavum* | | | B11474 | | | | | |
| *Brevibacterium* | *flavum* | | | B11472 | | | | | |
| *Brevibacterium* | *flavum* | 21127 | | | | | | | |
| *Brevibacterium* | *flavum* | 21128 | | | | | | | |
| *Brevibacterium* | *flavum* | 21427 | | | | | | | |
| *Brevibacterium* | *flavum* | 21475 | | | | | | | |
| *Brevibacterium* | *flavum* | 21517 | | | | | | | |
| *Brevibacterium* | *flavum* | 21528 | | | | | | | |
| *Brevibacterium* | *flavum* | 21529 | | | | | | | |
| *Brevibacterium* | *flavum* | | | B11477 | | | | | |
| *Brevibacterium* | *flavum* | | | B11478 | | | | | |
| *Brevibacterium* | *flavum* | 21127 | | | | | | | |
| *Brevibacterium* | *flavum* | | | B11474 | | | | | |
| *Brevibacterium* | *healii* | 15527 | | | | | | | |
| *Brevibacterium* | *ketoglutamicum* | 21004 | | | | | | | |
| *Brevibacterium* | *ketoglutamicum* | 21089 | | | | | | | |
| *Brevibacterium* | *ketosoreductum* | 21914 | | | | | | | |
| *Brevibacterium* | *lactofermentum* | | | | 70 | | | | |
| *Brevibacterium* | *lactofermentum* | | | | 74 | | | | |
| *Brevibacterium* | *lactofermentum* | | | | 77 | | | | |
| *Brevibacterium* | *lactofermentum* | 21798 | | | | | | | |
| *Brevibacterium* | *lactofermentum* | 21799 | | | | | | | |
| *Brevibacterium* | *lactofermentum* | 21800 | | | | | | | |
| *Brevibacterium* | *lactofermentum* | 21801 | | | | | | | |

-continued

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| *Brevibacterium* | *lactofermentum* | | | B11470 | | | | | |
| *Brevibacterium* | *lactofermentum* | | | B11471 | | | | | |
| *Brevibacterium* | *lactofermentum* | 21086 | | | | | | | |
| *Brevibacterium* | *lactofermentum* | 21420 | | | | | | | |
| *Brevibacterium* | *lactofermentum* | 21086 | | | | | | | |
| *Brevibacterium* | *lactofermentum* | 31269 | | | | | | | |
| *Brevibacterium* | *linens* | 9174 | | | | | | | |
| *Brevibacterium* | *linens* | 19391 | | | | | | | |
| *Brevibacterium* | *linens* | 8377 | | | | | | | |
| *Brevibacterium* | *paraffinolyticum* | | | | | 11160 | | | |
| *Brevibacterium* | spec. | | | | | | 717.73 | | |
| *Brevibacterium* | spec. | | | | | | 717.73 | | |
| *Brevibacterium* | spec. | 14604 | | | | | | | |
| *Brevibacterium* | spec. | 21860 | | | | | | | |
| *Brevibacterium* | spec. | 21864 | | | | | | | |
| *Brevibacterium* | spec. | 21865 | | | | | | | |
| *Brevibacterium* | spec. | 21866 | | | | | | | |
| *Brevibacterium* | spec. | 19240 | | | | | | | |
| *Corynebacterium* | *acetoacidophilum* | 21476 | | | | | | | |
| *Corynebacterium* | *acetoacidophilum* | 13870 | | | | | | | |
| *Corynebacterium* | *acetoglutamicum* | | | B11473 | | | | | |
| *Corynebacterium* | *acetoglutamicum* | | | B11475 | | | | | |
| *Corynebacterium* | *acetoglutamicum* | 15806 | | | | | | | |
| *Corynebacterium* | *acetoglutamicum* | 21491 | | | | | | | |
| *Corynebacterium* | *acetoglutamicum* | 31270 | | | | | | | |
| *Corynebacterium* | *acetophilum* | | | B3671 | | | | | |
| *Corynebacterium* | *ammoniagenes* | 6872 | | | | | | 2399 | |
| *Corynebacterium* | *ammoniagenes* | 15511 | | | | | | | |
| *Corynebacterium* | *fujiokense* | 21496 | | | | | | | |
| *Corynebacterium* | *glutamicum* | 14067 | | | | | | | |
| *Corynebacterium* | *glutamicum* | 39137 | | | | | | | |
| *Corynebacterium* | *glutamicum* | 21254 | | | | | | | |
| *Corynebacterium* | *glutamicum* | 21255 | | | | | | | |
| *Corynebacterium* | *glutamicum* | 31830 | | | | | | | |
| *Corynebacterium* | *glutamicum* | 13032 | | | | | | | |
| *Corynebacterium* | *glutamicum* | 14305 | | | | | | | |
| *Corynebacterium* | *glutamicum* | 15455 | | | | | | | |
| *Corynebacterium* | *glutamicum* | 13058 | | | | | | | |
| *Corynebacterium* | *glutamicum* | 13059 | | | | | | | |
| *Corynebacterium* | *glutamicum* | 13060 | | | | | | | |
| *Corynebacterium* | *glutamicum* | 21492 | | | | | | | |
| *Corynebacterium* | *glutamicum* | 21513 | | | | | | | |
| *Corynebacterium* | *glutamicum* | 21526 | | | | | | | |
| *Corynebacterium* | *glutamicum* | 21543 | | | | | | | |
| *Corynebacterium* | *glutamicum* | 13287 | | | | | | | |
| *Corynebacterium* | *glutamicum* | 21851 | | | | | | | |
| *Corynebacterium* | *glutamicum* | 21253 | | | | | | | |
| *Corynebacterium* | *glutamicum* | 21514 | | | | | | | |
| *Corynebacterium* | *glutamicum* | 21516 | | | | | | | |
| *Corynebacterium* | *glutamicum* | 21299 | | | | | | | |
| *Corynebacterium* | *glutamicum* | 21300 | | | | | | | |
| *Corynebacterium* | *glutamicum* | 39684 | | | | | | | |
| *Corynebacterium* | *glutamicum* | 21488 | | | | | | | |
| *Corynebacterium* | *glutamicum* | 21649 | | | | | | | |
| *Corynebacterium* | *glutamicum* | 21650 | | | | | | | |
| *Corynebacterium* | *glutamicum* | 19223 | | | | | | | |
| *Corynebacterium* | *glutamicum* | 13869 | | | | | | | |
| *Corynebacterium* | *glutamicum* | 21157 | | | | | | | |
| *Corynebacterium* | *glutamicum* | 21158 | | | | | | | |
| *Corynebacterium* | *glutamicum* | 21159 | | | | | | | |
| *Corynebacterium* | *glutamicum* | 21355 | | | | | | | |
| *Corynebacterium* | *glutamicum* | 31808 | | | | | | | |
| *Corynebacterium* | *glutamicum* | 21674 | | | | | | | |
| *Corynebacterium* | *glutamicum* | 21562 | | | | | | | |
| *Corynebacterium* | *glutamicum* | 21563 | | | | | | | |
| *Corynebacterium* | *glutamicum* | 21564 | | | | | | | |
| *Corynebacterium* | *glutamicum* | 21565 | | | | | | | |
| *Corynebacterium* | *glutamicum* | 21566 | | | | | | | |
| *Corynebacterium* | *glutamicum* | 21567 | | | | | | | |
| *Corynebacterium* | *glutamicum* | 21568 | | | | | | | |
| *Corynebacterium* | *glutamicum* | 21569 | | | | | | | |
| *Corynebacterium* | *glutamicum* | 21570 | | | | | | | |
| *Corynebacterium* | *glutamicum* | 21571 | | | | | | | |
| *Corynebacterium* | *glutamicum* | 21572 | | | | | | | |
| *Corynebacterium* | *glutamicum* | 21573 | | | | | | | |
| *Corynebacterium* | *glutamicum* | 21579 | | | | | | | |

-continued

| Bacterium | | Deposition number | | | | | | | |
|---|---|---|---|---|---|---|---|---|---|
| Genus | species | ATCC | FERM | NRRL | CECT | NCIMB | CBS | NCTC | DSMZ |
| *Corynebacterium* | *glutamicum* | 19049 | | | | | | | |
| *Corynebacterium* | *glutamicum* | 19050 | | | | | | | |
| *Corynebacterium* | *glutamicum* | 19051 | | | | | | | |
| *Corynebacterium* | *glutamicum* | 19052 | | | | | | | |
| *Corynebacterium* | *glutamicum* | 19053 | | | | | | | |
| *Corynebacterium* | *glutamicum* | 19054 | | | | | | | |
| *Corynebacterium* | *glutamicum* | 19055 | | | | | | | |
| *Corynebacterium* | *glutamicum* | 19056 | | | | | | | |
| *Corynebacterium* | *glutamicum* | 19057 | | | | | | | |
| *Corynebacterium* | *glutamicum* | 19058 | | | | | | | |
| *Corynebacterium* | *glutamicum* | 19059 | | | | | | | |
| *Corynebacterium* | *glutamicum* | 19060 | | | | | | | |
| *Corynebacterium* | *glutamicum* | 19185 | | | | | | | |
| *Corynebacterium* | *glutamicum* | 13286 | | | | | | | |
| *Corynebacterium* | *glutamicum* | 21515 | | | | | | | |
| *Corynebacterium* | *glutamicum* | 21527 | | | | | | | |
| *Corynebacterium* | *glutamicum* | 21544 | | | | | | | |
| *Corynebacterium* | *glutamicum* | 21492 | | | | | | | |
| *Corynebacterium* | *glutamicum* | | | B8183 | | | | | |
| *Corynebacterium* | *glutamicum* | | | B8182 | | | | | |
| *Corynebacterium* | *glutamicum* | | | B12416 | | | | | |
| *Corynebacterium* | *glutamicum* | | | B12417 | | | | | |
| *Corynebacterium* | *glutamicum* | | | B12418 | | | | | |
| *Corynebacterium* | *glutamicum* | | | B11476 | | | | | |
| *Corynebacterium* | *glutamicum* | 21608 | | | | | | | |
| *Corynebacterium* | *lilium* | | P973 | | | | | | |
| *Corynebacterium* | *nitrilophilus* | 21419 | | | | 11594 | | | |
| *Corynebacterium* | spec. | | P4445 | | | | | | |
| *Corynebacterium* | spec. | | P4446 | | | | | | |
| *Corynebacterium* | spec. | 31088 | | | | | | | |
| *Corynebacterium* | spec. | 31089 | | | | | | | |
| *Corynebacterium* | spec. | 31090 | | | | | | | |
| *Corynebacterium* | spec. | 31090 | | | | | | | |
| *Corynebacterium* | spec. | 31090 | | | | | | | |
| *Corynebacterium* | spec. | 15954 | | | | | | | 20145 |
| *Corynebacterium* | spec. | 21857 | | | | | | | |
| *Corynebacterium* | spec. | 21862 | | | | | | | |
| *Corynebacterium* | spec. | 21863 | | | | | | | |

The abbreviations have the following meaning:
ATCC: American Type Culture Collection, Rockville, MD, USA
FERM: Fermentation Research Institute, Chiba, Japan
NRRL: ARS Culture Collection, Northern Regional Research Laboratory, Peoria, IL, USA
CECT: Coleccion Espanola de Cultivos Tipo, Valencia, Spain
NCIMB: National Collection of Industrial and Marine Bacteria Ltd., Aberdeen, UK
CBS: Centraalbureau voor Schimmelcultures, Baarn, NL
NCTC: National Collection of Type Cultures, London, UK
DSMZ: Deutsche Sammlung von Mikroorganismen und Zellkulturen, Braunschweig, Germany Through the nucleic acids of the invention having promoter activity and the expression units of the invention it is possible with the aid of the methods of the invention described above to regulate the metabolic pathways in the genetically modified microorganisms of the invention described above to specific biosynthetic products.

For this purpose, for example, metabolic pathways which lead to a specific biosynthetic product are enhanced by causing or increasing the transcription rate or expression rate of genes of this biosynthetic pathway in which the increased quantity of protein leads to an increased total activity of these proteins of the desired biosynthetic pathway and thus to an enhanced metabolic flux toward the desired biosynthetic product.

In addition, metabolic pathways which diverge from a specific biosynthetic product can be diminished by reducing the transcription rate or expression rate of genes of this divergent biosynthetic pathway in which the reduced quantity of protein leads to a reduced total activity of these proteins of the unwanted biosynthetic pathway and thus additionally to an enhanced metabolic flux toward the desired biosynthetic product.

The genetically modified microorganisms of the invention are able for example to produce biosynthetic products from glucose, sucrose, lactose, fructose, maltose, molasses, starch, cellulose or from glycerol and ethanol.

The invention therefore relates to a method for producing biosynthetic products by cultivating genetically modified microorganisms of the invention.

Depending on the desired biosynthetic product, the transcription rate or expression rate of various genes must be increased or reduced. Ordinarily, it is advantageous to alter the transcription rate or expression rate of a plurality of genes, i.e. to increase the transcription rate or expression rate of a combination of genes and/or to reduce the transcription rate or expression rate of a combination of genes.

In the genetically modified microorganisms of the invention, at feast one altered, i.e. increased or reduced, transcription rate or expression rate of a gene is attributable to a nucleic acid of the invention having promoter activity or expression unit of the invention.

Further, additionally altered, i.e. additionally increased or additionally reduced, transcription rates or expression rates of further genes in the genetically modified microorganism may, but need not, derive from the nucleic acids of the invention having promoter activity or the expression units of the invention.

The invention therefore further relates to a method for producing biosynthetic products by cultivating genetically modified microorganisms of the invention.

Preferred biosynthetic products are fine chemicals.

The term "fine chemical" is known in the art and includes compounds which are produced by an organism and are used in various branches of industry such as, for example but not restricted to, the pharmaceutical industry, the agriculture, cosmetics, food and feed industries. Those compounds include organic acids such as, for example, tartaric acid, itaconic acid and diaminopimelic acid, and proteinogenic and non-proteinogenic amino acids, purine bases and pyrimidine bases, nucleosides and nucleotides (as described for example in Kuninaka, A. (1996) Nucleotides and related compounds, pp. 561-612, in Biotechnology vol. 6, Rehm et al., editors, VCH: Weinheim and the references present therein), lipids, saturated and unsaturated fatty acids (e.g. arachidonic acid), diols (e.g. propanediol and butanediol), carbohydrates (e.g. hyaluronic acid and trehalose), aromatic compounds (e.g. aromatic amines, vanillin and indigo), vitamins and cofactors (as described in Ullmann's Encyclopedia of Industrial Chemistry, vol. A27, "Vitamins", pp. 443-613 (1996) VCH: Weinheim and the references present therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held on Sep. 1-3, 1994 in Penang, Malaysia, AOCS Press (1995)), enzymes and all other chemicals described by Gutcho (1983) in Chemicals by Fermentation, Noyes Data Corporation, ISBN: 0818805086 and the references indicated therein. The metabolism and the uses of certain fine chemicals are explained further below.

I. Amino Acid Metabolism and Uses

The amino acids comprise the fundamental structural units of all proteins and are thus essential for normal cell functions. The term "amino acid" is known in the art. The proteinogenic amino acids, of which there are 20 types, serve as structural units for proteins, in which they are linked together by peptide bonds, whereas the non-proteinogenic amino acids (of which hundreds are known) usually do not occur in proteins (see Ullmann's Encyclopedia of Industrial Chemistry, vol. A2, pp. 57-97 VCH: Weinheim (1985)). The amino acids may be in the D or L configuration, although L-amino acids are usually the only type found in naturally occurring proteins. Biosynthetic and degradation pathways of each of the proteinogenic amino acids are well characterized both in prokaryotic and in eukaryotic cells (see, for example, Stryer, L. Biochemistry, 3rd edition, pp. 578-590 (1988)). The "essential" amino acids (histidine, isoleucine, leucine, lysine, methionine, phenylalanine, threonine, tryptophan and valine), so-called because they must, owing to the complexity of their biosynthesis, be taken in with the diet, are converted by simple biosynthetic pathways into the other 11 "nonessential" amino acids (alanine, arginine, asparagine, aspartate, cysteine, glutamate, glutamine, glycine, proline, serine and tyrosine). Higher animals have the ability to synthesize some of these amino acids, but the essential amino acids must be taken in with the food in order for normal protein synthesis to take place, Apart from their function in protein biosynthesis, these amino acids are chemicals of interest per se, and it has been found that many have uses in various applications in the food, feed, chemicals, cosmetics, agriculture and pharmaceutical industries. Lysine is an important amino acid not only for human nutrition but also for monogastric species such as poultry and pigs. Glutamate is used most frequently as flavor additive (monosodium glutamate, MSG) and widely in the food industry, as well as aspartate, phenylalanine, glycine and cysteine. Glycine, L-methionine and tryptophan are all used in the pharmaceutical industry. Glutamine, valine, leucine, isoleucine, histidine, arginine, proline, serine and alanine are used in the pharmaceutical industry and the cosmetics industry. Threonine, tryptophan and D-/L-methionine are widely used feed additives (Leuchtenberger, W. (1996) Amino acids-technical production and use, pp. 466-502 in Rehm et al., (editors) Biotechnology vol. 6, chapter 14a, VCH: Weinheim). It has been found that these amino acids are additionally suitable as precursors for synthesizing synthetic amino acids and proteins such as N-acetylcysteine, S-carboxymethyl-L-cysteine, (S)-5-hydroxytryptophan and other substances described in Ullmann's Encyclopedia of Industrial Chemistry, vol. A2, pp. 57-97, VCH, Weinheim, 1085.

The biosynthesis of these natural amino acids in organisms able to produce them, for example bacteria, has been well characterized (for a review of bacterial amino acid biosynthesis and its regulation, see Umbarger, H. E. (1978) Ann. Rev. Biochem. 47; 533-606). Glutamate is synthesized by reductive amination of □-ketoglutarate, an intermediate in the citric acid cycle. Glutamine, proline and arginine are each generated successively from glutamate. Biosynthesis of serine takes place in a three-step method and starts with 3-phosphoglycerate (an intermediate of glycolysis) and yields this amino acid after oxidation, transamination and hydrolysis steps. Cysteine and glycine are each produced from serine, the former by condensation of homocysteine with serine, and the latter by transfer of the side-chain □-carbon atom to tetrahydrofolate in a reaction catalyzed by serine transhydroxymethylase. Phenylalanine and tyrosine are synthesized from the precursors of the glycolysis and pentose phosphate pathways, erythrose 4-phosphate and phosphenolpyruvate in a 9-step biosynthetic pathway which differs only in the last two steps after the synthesis of prephenate. Tryptophan is likewise produced from these two starting molecules, but its synthesis takes place in an 11-step pathway. Tyrosine can also be produced from phenylalanine in a reaction catalyzed by phenylalanine hydroxylase. Alanine, valine and leucine are each biosynthetic products of pyruvate, the final product of glycolysis. Aspartate is formed from oxalacetate, an intermediate of the citrate cycle. Asparagine, methionine, threonine and lysine are each produced by conversion of aspartate. Isoleucine is formed from threonine. Histidine is formed in a complex 9-step pathway from 5-phosphoribosyl 1-pyrophosphate, an activated sugar.

Amino acids whose quantity exceeds the protein biosynthesis requirement of the cell cannot be stored and are instead degraded, so that intermediates are provided for the main metabolic pathways of the cell (for a review, see Stryer, L., Biochemistry, 3rd edition, chapter 21 "Amino Acid Degradation and the Urea Cycle"; pp. 495-516 (1988)). Although the cell is able to convert unwanted amino acids into useful metabolic intermediates, amino acid production is costly in terms of the energy, the precursor molecules and the enzymes required for their synthesis. It is therefore not surprising that amino acid biosynthesis is regulated by feedback inhibition, where the presence of a particular amino acid slows down or entirely terminates its own production (for a review of the feedback mechanism in amino acid biosynthetic pathways, see Stryer, L., Biochemistry, 3rd edition, chapter 24, "Biosynthesis of Amino Acids and Heme", pp. 575-600 (1988)). The output of a particular amino acid is therefore restricted by the quantity of this amino acid in the cell.

II. Vitamins, Cofactors and Nutraceutical Metabolism, and Uses

Vitamins, cofactors and nutraceuticals comprise a further group of molecules. Higher animals have lost the ability to synthesize these and therefore need to take them in, although they are easily synthesized by other organisms such as bacteria. These molecules are either biologically active molecules per se or precursors of biologically active substances which serve as electron carriers or intermediates in a number of metabolic pathways. These compounds have, besides their nutritional value, also a significant industrial value as coloring agents, antioxidants and catalysts or other processing aids. (For a review of the structure, activity and industrial applications of these compounds, see, for example, Ullmann's Encyclopedia of Industrial Chemistry, "Vitamins", vol. A27, pp. 443-613, VCH: Weinheim, 1996). The term "vitamin" is known in the art and includes nutrients which are required by an organism for normal functioning, but cannot be synthesized by this organism itself. The group of vitamins may include cofactors and nutraceutical compounds. The term "cofactor" includes non-protein compounds which are necessary for the occurrence of normal enzymic activity. These compounds may be organic or inorganic; the cofactor molecules of the invention are preferably organic. The term "nutraceutical" includes food additives which promote health in plants and animals, especially in humans. Examples of such molecules are vitamins, antioxidants and likewise certain lipids (e.g. polyunsaturated fatty acids).

Biosynthesis of these molecules in organisms able to produce them, such as bacteria, has been characterized in detail (Ullmann's Encyclopedia of Industrial Chemistry, "Vitamins", vol. A27, pp. 443-613, VCH: Weinheim, 1996, Michal, G. (1999) Biochemical Pathways: An Atlas of Biochemistry and Molecular Biology, John Wiley & Sons; Ong, A. S., Niki, E. and Packer, L. (1995) "Nutrition, Lipids, Health and Disease" Proceedings of the UNESCO/Confederation of Scientific and Technological Associations in Malaysia and the Society for free Radical Research—Asia, held on Sep. 1-3, 1994, in Penang, Malaysia, AOCS Press, Champaign, Ill. X, 374 S).

Thiamine (vitamin $B_1$) is formed by chemical coupling of pyrimidine and thiazole units. Riboflavin (vitamin $B_2$) is synthesized from guanosine 5'-triphosphate (GTP) and ribose 5-phosphate, Riboflavin in turn is employed for the synthesis of flavin mononucleotide (FMN) and flavin-adenine dinucleotide (FAD). The family of compounds referred to jointly as "vitamin B6" (e.g. pyridoxine, pyridoxamine, pyridoxal 6 phosphate and the commercially used pyridoxine hydrochloride) are all derivatives of the common structural unit 5-hydroxy-6-methylpyridine. Pantothenate (pantothenic acid, R-(+)-N-(2,4-dihydroxy-3,3-dimethyl-1-oxobutyl)-□-alanine) can be produced either by chemical synthesis or by fermentation. The last steps in pantothenate biosynthesis consist of ATP-driven condensation of Fi-alanine and pantoic acid. The enzymes responsible for the biosynthetic steps for conversion into pantoic acid, into □-alanine and for condensation to pantothenic acid are known. The metabolically active form of pantothenate is coenzyme A, whose biosynthesis proceeds through 5 enzymatic steps. Pantothenate, pyridoxal 5-phosphate, cysteine and ATP are the precursors of coenzyme A. These enzymes catalyze not only the formation of pantothenate but also the production of (R)-pantoic acid, (R)-pantolactone, (R)-panthenol (provitamin B5), pantethein (and its derivatives) and coenzyme A.

The biosynthesis of biotin from the precursor molecule pimeloyl-CoA in microorganisms has been investigated in detail, and several of the genes involved have been identified. It has emerged that many of the corresponding proteins are involved in Fe cluster synthesis and belong to the class of nifS proteins. Lipoic acid is derived from octanoic acid and serves as coenzyme in energy metabolism, where it becomes a constituent of the pyruvate dehydrogenase complex and of the □-ketoglutarate dehydrogenase complex. The folates are a group of substances which are all derived from folic acid, which in turn is derived from L-glutamic acid, p-aminobenzoic acid and 6-methylpterin. The biosynthesis of folic acid and its derivatives starting from the metabolic intermediates guanosine 5'-triphosphate (GTP), L-glutamic acid and p-aminobenzoic acid has been investigated in detail in certain microorganisms.

Corrinoids (such as the cobalamins and in particular vitamin $B_{12}$) and the porphyrins belong to a group of chemicals which are distinguished by a tetrapyrrole ring system. The biosynthesis of vitamin $B_{12}$ is so complex that it has not yet been completely characterized, but most of the enzymes and substrates involved are now known. Nicotinic acid (nicotinate) and nicotinamide are pyridine derivatives, which are also referred to as "niacin". Niacin is the precursor of the important coenzymes NAD (nicotinamide-adenine dinucleotide) and NADP (nicotinamide-adenine dinucleotide phosphate) and their reduced forms.

The production of these compounds on the industrial scale is based for the most part on cell-free chemical syntheses, although some of these chemicals have likewise been produced by large-scale culturing of microorganisms, such as riboflavin, vitamin $B_6$, pantothenate and biotin. Only vitamin $B_{12}$ is produced solely by fermentation, because of the complexity of its synthesis. In vitro methods require a considerable expenditure of materials and time and frequently of high costs.

III. Purine, Pyrimidine, Nucleoside and Nucleotide Metabolism and Uses

Genes for purine and pyrimidine metabolism and their corresponding proteins are important targets for the therapy of neoplastic diseases and viral infections The term "purine" or "pyrimidine" comprises nitrogenous bases which are a constituent of nucleic acids, coenzymes and nucleotides. The term "nucleotide" comprises the fundamental structural units of nucleic acid molecules, which include a nitrogenous base, a pentose sugar (the sugar in RNA is ribose, and the sugar in DNA is D-deoxyribose) and phosphoric acid. The term "nucleoside" comprises molecules which serve as precursors of nucleotides but which, in contrast to nucleotides, have no phosphoric acid unit. It is possible by inhibiting the biosynthesis of these molecules or their mobilization for formation of nucleic acid molecules to inhibit RNA and DNA synthesis; targeted inhibition of this activity in carcinogenic cells allows the ability of tumor cells to divide and replicate to be inhibited.

There are also nucleotides which do not form nucleic acid molecules but serve as energy stores (i.e. AMP) or as coenzymes (i.e. FAD and NAD).

Several publications have described the use of these chemicals for these medical indications, where purine and/or pyrimidine metabolism is influenced (e.g. Christopherson, R. I. and Lyons, S. D. (1990) "Potent inhibitors of de novo pyrimidine and purine biosynthesis as chemotherapeutic agents", Med. Res. Reviews 10: 505-548). Investigations on enzymes involved in purine and pyrimidine metabolism have concentrated on the development of novel medicaments which can be used for example as immunosuppressants or antiproliferatives (Smith, J. L. "Enzymes in Nucleotide Synthesis" Curr. Opin. Struct. Biol. 5 (1995) 752-757; Biochem. Soc. Transact. 23 (1995) 877-902). Purine and pyrimidine bases, nucleosides and nucleotides have, however, also other possible uses: as intermediates in the biosynthesis of various fine chemicals (e.g. thiamine, S-adenosylmethionine, folates or riboflavin), as energy carriers for the cell (e.g. ATP or GTP) and for chemicals themselves, are commonly used as flavor enhancers (e.g. IMP or GMP) or for many medical applications (see, for example, Kuninaka, A., (1996) "Nucleotides and Related Compounds" in Biotechnology, vol. 6, Rehm et al., editors VCH: Weinheim, pp. 561-612). Enzymes involved in purine, pyridine, nucleoside or nucleotide metabolism are also increasingly serving as targets for the development of chemicals for crop protection, including fungicides, herbicides and insecticides.

The metabolism of these compounds in bacteria has been characterized (for reviews, see, for example, Zalkin, H. and Dixon, J. E. (1992) "De novo purine nucleotide biosynthesis" in Progress in Nucleic Acids Research and Molecular biology, vol. 42, Academic Press, pp. 259-287; and Michal, G. (1999) "Nucleotides and Nucleosides"; chapter 8 in: Biochemical Pathways. An Atlas of Biochemistry and Molecular Biology, Wiley, New York). Purine metabolism, which is the subject of intensive research, is essential for normal functioning of the cell. Impaired purine metabolism in higher animals may cause severe disorders, e.g. gout. The purine nucleotides are synthesized over a number of steps via the intermediate compound inosine 5'-phosphate (IMP) from ribose 5-phosphate, leading to production of guanosine 5'-monophosphate (GMP) or adenosine 5'-monophosphate (AMP), from which the triphosphate forms, which are used as nucleotides, can easily be prepared. These compounds are also used as energy stores, so that their degradation provides energy for many different biochemical processes in the cell. Pyrimidine biosynthesis takes place via the formation of uridine 5'-monophosphate (UMP) from ribose 5-phosphate. UMP in turn is converted into cytidine 5'-triphosphate (CTP), The deoxy forms of all nucleotides are prepared in a one-step reduction reaction from the diphosphate ribose form of the nucleotide to give the diphosphate deoxyribose form of the nucleotide. After phosphorylation, those molecules are able to take part in DNA synthesis.

IV. Trehalose Metabolism and Uses

Trehalose consists of two glucose molecules which are linked together via an □,□-1,1 linkage. It is commonly used in the food industry as sweetener, as additive to dried or frozen foods and in beverages. However, it is also used in the pharmaceutical industry, the cosmetics and biotechnology industry (see, for example, Nishimoto et al., (1998) U.S. Pat. No. 5,759,610; Singer, M. A. and Lindquist, S. Trends Biotech. 16 (1998) 460-467; Paiva, C. L. A. and Panek, A. D. Biotech Ann. Rev. 2 (1996) 293-314; and Shiosaka, M. FFIJ. Japan 172 (1997) 97-102). Trehalose is produced by enzymes of many microorganisms and is released in a natural way into the surrounding medium, from which it can be isolated by methods known in the art.

Particularly preferred biosynthetic products are selected from the group of organic acids, proteins, nucleotides and nucleosides, both proteinogenic and non-proteinogenic amino acids, lipids and fatty acids, diols, carbohydrates, aromatic compounds, vitamins and cofactors, enzymes and proteins.

Preferred organic acids are tartaric acid, itaconic acid and diaminopimelic acid.

Preferred nucleosides and nucleotides are described for example in Kuninaka, A. (1996) Nucleotides and related compounds, pp. 561-612, in Biotechnology, vol. 6, Rehm et al., editors VCH: Weinheim and references present therein.

Preferred biosynthetic products are additionally lipids, saturated and unsaturated fatty acids such as, for example, arachidonic acid, dials such as, for example, propanediol and butanediol, carbohydrates such as, for example, hyaluronic acid and trehalose, aromatic compounds such as, for example, aromatic amines, vanillin and indigo, vitamins and cofactors as described for example in Ullmann's Encyclopedia of Industrial Chemistry, vol. A27, "Vitamins", pp. 443-613 (1996) VCH: Weinheim and the references present therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held on Sep. 1-3, 1994 in Penang, Malaysia, AOCS Press (1995)), enzymes, polyketides (Cane et al, (1998) Science 282: 63-68) and all other chemicals described by Gutcho (1083) in Chemicals by Fermentation, Noyes Data Corporation, ISBN: 0818805086 and the references indicated therein.

Particularly preferred biosynthetic products are amino acids, particularly preferably essential amino acids, in particular L-glycine, L-alanine, L-leucine, L-methionine, L-phenylalanine, L-tryptophan, L-lysine, L-glutamine, L-glutamic acid, L-serine, L-proline, L-valine, L-isoleucine, L-cysteine, L-tyrosine, L-histidine, L-arginine, L-asparagine, L-aspartic acid and L-threonine, L-homoserine, especially L-lysine, L-methionine and L-threonine. An amino acid such as, for example, lysine, methionine and threonine means hereinafter both in each case the L and the D form of the amino acid, preferably the L form, i.e. for example L-lysine, L-methionine and L4 threonine.

The invention relates in particular to a method for producing lysine by cultivating genetically modified microorganisms with increased or caused expression rate of at least one gene compared with the wild type, where ch) the specific expression activity in the microorganism of at least one endogenous expression unit of the invention which regulates the expression of the endogenous genes, is increased compared with the wild type, or dh) the expression of genes in the microorganism is regulated by expression units of the invention or by expression units with increased specific expression activity according to embodiment a), where the genes are heterologous in relation to the expression units, and where the genes are selected from the group of nucleic acids encoding an aspartate kinase, nucleic acids encoding an aspartate-semialdehyde dehydrogenase, nucleic acids encoding a diaminopimelate dehydrogenase, nucleic acids encoding a diaminopimelate decarboxylase, nucleic acids encoding a dihydrodipicolinate synthetase, nucleic acids encoding a dihydrodipicolinate reductase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a transcriptional regulator LuxR, nucleic acids encoding a transcriptional regulator LysR1, nucleic acids encoding a transcriptional regulator LysR2, nucleic acids encoding a malate-quinone oxidoreductase, nucleic acids encoding a glucose-6-phosphate dehydrogenase, nucleic acids encoding a 6-phosphogluconate dehydrogenase, nucleic acids encoding a transketolase, nucleic acids encoding a transaldolase, nucleic acids encoding a lysine exporter, nucleic acids encoding a biotin ligase, nucleic acids encoding an arginyl-tRNA synthetase, nucleic acids encoding a phosphoenolpyruvate carboxylase, nucleic acids encoding a fructose-1,6-bisphosphatase, nucleic acids encoding a protein OpcA, nucleic acids encoding a 1-phosphofructokinase and nucleic acids encoding a 6-phosphofructokinase.

As described above for the methods, the regulation of the expression of these genes in the microorganism by expression units of the invention or by expression units of the invention with increased specific expression activity in accordance with embodiment ch) is achieved by dh1) introducing one or more expression units of the invention, where appropriate with increased specific expression activity, into the genome of the microorganism so that expression of one or more endogenous genes takes place under the control of the introduced expression units of the invention, where appropriate with increased specific expression activity, or dh2) introducing one or more of these genes into the genome of the microorganism so that expression of one or more of the introduced genes takes place under the control of the endogenous expression units of the invention, where appropriate with increased specific expression activity, or dh3) introducing one of more nucleic acid constructs comprising an expression unit of the invention, where appropriate with increased specific expression activity, and functionally linked one or more nucleic acids to be expressed, into the microorganism.

A further preferred embodiment of the method described above for preparing lysine comprises the genetically modified microorganisms, compared with the wild type, having additionally an increased activity, of at least one of the activities selected from the group of aspartate kinase activity, aspartate-semialdehyde dehydrogenase activity, diaminopimelate dehydrogenase activity, diaminopimelate decarboxylase activity, dihydrodipicolinate synthetase activity, dihydrodipicolinate reductase activity, glyceraldehyde-3-phosphate dehydrogenase activity, 3-phosphoglycerate kinase activity, pyruvate carboxylase activity, triosephosphate isomerase activity, activity of the transcriptional regulator LuxR, activity of the transcriptional regulator LysR1, activity of the transcriptional regulator LysR2, malate-quinone oxidoreductase activity, glucose-6-phosphate dehydrogenase activity, 6-phosphogluconate dehydrogenase activity, transketolase activity, transaldolase activity, lysine exporter activity, arginyl-tRNA synthetase activity, phosphoenolpyruvate carboxylase activity, fructose-1,6-bisphosphatase activity, protein OpcA activity, 1-phosphofructokinase activity, 6-phosphofructokinase activity and biotin ligase activity.

A further particularly preferred embodiment of the method described above for preparing lysine comprises the genetically modified microorganisms having, compared with the wild type, additionally a reduced activity, of at least one of the activities selected from the group of threonine dehydratase activity, homoserine O-acetyltransferase activity, O-acetylhomoserine sulfhydrylase activity, phosphoenolpyruvate carboxykinase activity, pyruvate oxidase activity, homoserine kinase activity, homoserine dehydrogenase activity, threonine exporter activity, threonine efflux protein activity, asparaginase activity, aspartate decarboxylase activity and threonine synthase activity.

These additional increased or reduced activities of at least one of the activities described above may, but need not, be caused by a nucleic acid of the invention having promoter activity and/or an expression unit of the invention.

The invention further relates to a method for producing methionine by cultivating genetically modified microorganisms with increased or caused expression rate of at least one gene compared with the wild type, where ch) the specific expression activity in the microorganism of at least one endogenous expression unit of the invention, which regulates the expression of the endogenous genes, is increased compared with the wild type, or dh) the expression of genes in the microorganism is regulated by expression units of the invention or by expression units of the invention with increased specific expression activity according to embodiment a), where the genes are heterologous in relation to the expression units, and where the genes are selected from the group of nucleic acids encoding an aspartate kinase, nucleic acids encoding an aspartate-semialdehyde dehydrogenase, nucleic acids encoding a homoserine dehydrogenase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a homoserine O-acetyltransferase, nucleic acids encoding a cystathionine gamma-synthase, nucleic acids encoding a cystathionine beta-lyase, nucleic acids encoding a serine hydroxymethyltransferase, nucleic acids encoding an O-acetylhomoserine sulfhydrylase, nucleic acids encoding a methylenetetrahydrofolate reductase, nucleic acids encoding a phosphoserine aminotransferase, nucleic acids encoding a phosphoserine phosphatase, nucleic acids encoding a serine acetyltransferase, nucleic acids encoding a cysteine synthase I, nucleic acids encoding a cysteine synthase II activity, nucleic acids encoding a coenzyme B12-dependent methionine synthase activity, nucleic acids encoding a coenzyme B12-independent methionine synthase activity, nucleic acids encoding a sulfate adenylyltransferase activity, nucleic acids encoding a phosphoadenosine phosphosulfate reductase activity, nucleic acids encoding a ferredoxin-sulfite reductase activity, nucleic acids encoding a ferredoxin NADPH-reductase activity, nucleic acids encoding a ferredoxin activity, nucleic acids encoding a protein of sulfate reduction RXA077, nucleic acids encoding a protein of sulfate reduction RXA248, nucleic acids encoding a protein of sulfate reduction RXA247, nucleic acids encoding an RXA0655 regulator and nucleic acids encoding an RXN2910 regulator.

As described above for the methods, the regulation of the expression of these genes in the microorganism by expression units of the invention or by expression units of the invention with increased specific expression activity according to embodiment ch) is achieved by dh1) introducing one or more expression units of the invention, where appropriate with increased specific expression activity, into the genome of the microorganism so that expression of one or more of these endogenous genes takes place under the control of the introduced expression units of the invention, where appropriate with increased specific expression activity, or dh2) introducing one or more genes into the genome of the microorganism so that expression of one or more of the introduced genes takes place under the control of the endogenous expression units of the invention, where appropriate with increased specific expression activity, or dh3) introducing one or more nucleic acid constructs comprising an expression unit of the invention, where appropriate with increased specific expression activity, and functionally linked one or more nucleic acids to be expressed, into the microorganism, A further preferred embodiment of the method described above for preparing methionine comprises the genetically modified microorganisms having, compared with the wild type, additionally an increased activity, of at least one of the activities selected from the group of aspartate kinase activity, aspartate-semialdehyde dehydrogenase activity, homoserine dehydrogenase activity, glyceraldehyde-3-phosphate dehydrogenase activity, 3-phosphoglycerate kinase activity, pyruvate carboxylase activity, triosephosphate isomerase activity, homoserine O-acetyltransferase activity, cystathionine gamma-synthase activity, cystathionine beta-lyase activity, serine hydroxymethyltransferase activity, O-acetylhomoserine sulfhydrylase activity methylenetetrahydrofolate reductase activity, phosphoserine aminotransferase activity, phosphoserine phosphatase activity, serine acetyltransferase activity, cysteine synthase I activity, cysteine synthase II activity, coenzyme B12 dependent methionine synthase activity, coenzyme B12-independent methionine synthase activity, sulfate adenylyltransferase activity, phosphoadenosine-phosphosulfate reductase activity, ferredoxin-sulfite reductase activity, ferredoxin NADPH-reductase activity, ferredoxin activity, activity of a protein of sulfate reduction RXA077, activity of a protein of sulfate reduction RXA248, activity of a protein of sulfate reduction RXA247, activity of an RXA655 regulator and activity of an RXN2910 regulator.

A further particularly preferred embodiment of the method described above for preparing methionine comprises the genetically modified microorganisms having, compared with the wild type, additionally a reduced activity, of at least one of the activities selected from the group of homoserine kinase activity, threonine dehydratase activity, threonine synthase activity, meso-diaminopimelate D-dehydrogenase activity, phosphoenolpyruvate carboxykinase activity, pyruvate oxidase activity, dihydrodipicolinate synthase activity, dihydrodipicolinate reductase activity and diaminopicolinate decarboxylase activity.

These additional increased or reduced activities of at least one of the activities described above may, but need not, be caused by a nucleic acid of the invention having promoter activity and/or an expression unit of the invention.

The invention further relates to a method for preparing threonine by cultivating genetically modified microorganisms with increased or caused expression rate of at least one gene compared with the wild type, where ch) the specific expression activity in the microorganism of at least one endogenous expression unit of the invention, which regulates the expression of the endogenous genes, is increased compared with the wild type, or dh) the expression of genes in the microorganism is regulated by expression units of the invention or by expression units of the invention with increased specific expression activity according to embodiment a), where the genes are heterologous in relation to the expression units, and where the genes are selected from the group of nucleic acids encoding an aspartate kinase, nucleic acids encoding an aspartate-semialdehyde dehydrogenase, nucleic acids encoding a glyceraldehyde-3-phosphate dehydrogenase, nucleic acids encoding a 3-phosphoglycerate kinase, nucleic acids encoding a pyruvate carboxylase, nucleic acids encoding a triosephosphate isomerase, nucleic acids encoding a homoserine kinase, nucleic acids encoding a threonine synthase, nucleic acids encoding a threonine exporter carrier, nucleic acids encoding a glucose-6-phosphate dehydrogenase, nucleic acids encoding a transaldolase, nucleic acids encoding a transketolase, nucleic acids encoding a malate-quinone oxidoreductase, nucleic acids encoding a 6-phosphogluconate dehydrogenase, nucleic acids encoding a lysine exporter, nucleic acids encoding a biotin ligase, nucleic acids encoding a phosphoenolpyruvate carboxylase, nucleic acids encoding a threonine efflux protein, nucleic acids encoding a fructose-1,6-bisphosphatase, nucleic acids encoding an OpcA protein, nucleic acids encoding a 1-phosphofructokinase, nucleic acids encoding a 6-phosphofructokinase, and nucleic acids encoding a homoserine dehydrogenase.

As described above for the methods, the regulation of the expression of these genes in the microorganism by expression units of the invention or by expression units of the invention with increased specific expression activity according to embodiment ch) is achieved by dh1) introducing one or more expression units of the invention, where appropriate with increased specific expression activity, into the genome of the microorganism so that expression of one or more of these endogenous genes takes place under the control of the introduced expression units of the invention, where appropriate with increased specific expression activity, or dh2) introducing one or more of these genes into the genome of the microorganism so that expression of one or more of the introduced genes takes place under the control of the endogenous expression units of the invention, where appropriate with increased specific expression activity, or dh3) introducing one or more nucleic acid constructs comprising an expression unit of the invention, where appropriate with increased specific expression activity, and functionally linked one or more nucleic acids to be expressed, into the microorganism.

A further preferred embodiment of the method described above for preparing threonine comprises the genetically modified microorganisms having, compared with the wild type, additionally an increased activity, of at least one of the activities selected from the group of aspartate kinase activity, aspartate-semialdehyde dehydrogenase activity, glyceraldehyde-3-phosphate dehydrogenase activity, 3-phosphoglycerate kinase activity, pyruvate carboxylase activity, triosephosphate isomerase activity, threonine synthase activity, activity of a threonine export carrier, transaldolase activity, transketolase activity, glucose-6-phosphate dehydrogenase activity, malate-quinone oxidoreductase activity, homoserine kinase activity, biotin ligase activity, phosphoenolpyruvate carboxylase activity, threonine efflux protein activity, protein OpcA activity, 1-phosphofructokinase activity, 6-phosphofructokinase activity, fructose-1,6-bisphosphatase activity, 6-phosphogluconate dehydrogenase and homoserine dehydrogenase activity.

A further particularly preferred embodiment of the method described above for preparing threonine comprises the genetically modified microorganisms having, compared with the wild type, additionally a reduced activity, of at least one of the activities selected from the group of threonine dehydratase activity, homoserine O-acetyltransferase activity, serine hydroxymethyltransferase activity, O-acetylhomoserine sulfhydrylase activity, meso-diaminopimelate D-dehydrogenase activity, phosphoenolpyruvate carboxykinase activity, pyruvate oxidase activity, dihydrodipicolinate synthetase activity, dihydrodipicolinate reductase activity, asparaginase activity, aspartate decarboxylase activity, lysine exporter activity, acetolactate synthase activity, ketol-acid reductoisomerase activity, branched chain aminotransferase activity, coenzyme B12-dependent methionine synthase activity, coenzyme B12-independent methionine synthase activity, dihydroxy-acid dehydratase activity and diaminopicolinate decarboxylase activity.

These additional increased or reduced activities of at least one of the activities described above may, but need not, be caused by a nucleic acid of the invention having promoter activity and/or an expression unit of the invention.

The term "activity" of a protein means in the case of enzymes the enzymic activity of the corresponding protein, and in the case of other proteins, for example structural or transport proteins, the physiological activity of the proteins The enzymes are ordinarily able to convert a substrate into a product or catalyze this conversion step.

Accordingly, the "activity" of an enzyme means the quantity of substrate converted by the enzyme, or the quantity of product formed, in a particular time.

Thus, where an activity is increased compared with the wild type, the quantity of the substrate converted by the enzyme, or the quantity of product formed, in a particular time is increased compared with the wild type.

This increase in the "activity" preferably amounts, for all activities described hereinbefore and hereinafter, to at least 5%, further preferably at least 20%, further preferably at least 50%, further preferably at least 100%, more preferably at least 300%, even more preferably at least 500%, especially at least 600% of the "activity of the wild type".

Thus, where an activity is reduced compared with the wild type, the quantity of substrate converted by the enzyme, or the quantity of product formed, in a particular time is reduced compared with the wild type.

A reduced activity preferably means the partial or substantially complete suppression or blocking, based on various cell biological mechanisms, of the functionality of this enzyme in a microorganism.

A reduction in the activity comprises a quantitative decrease in an enzyme as far as substantially complete absence of the enzyme (i.e. lack of detectability of the corresponding activity or lack of immunological detectability of the enzyme). The activity in the microorganism is preferably reduced, compared with the wild type, by at least 5%, further preferably by at least 20%, further preferably by at least 50%, further preferably by 100%. "Reduction" also means in particular the complete absence of the corresponding activity.

The activity of particular enzymes in genetically modified microorganisms and in the wild type, and thus the increase or reduction in the enzymic activity, can be measured by known methods such as, for example, enzyme assays.

For example, a pyruvate carboxylase means a protein which exhibits the enzymatic activity of converting pyruvate into oxaloacetate.

Correspondingly, a pyruvate carboxylase activity means the quantity of pyruvate converted by the pyruvate carboxlyase protein, or quantity of oxaloacetate formed, in a particular time.

Thus, where a pyruvate carboxylase activity is increased compared with the wild type, the quantity of pyruvate converted by the pyruvate carboxylase protein, or the quantity of oxaloacetate formed, in a particular time is increased compared with the wild type.

This increase in the pyruvate carboxylase activity is preferably at least 5%, further preferably at least 20%, further preferably at least 50%, further preferably at least 100%, more preferably at least 300%, even more preferably at least 500%, in particular at least 600%, of the pyruvate carboxylase activity of the wild type, In addition, for example a phosphoenolpyruvate carboxykinase activity means the enzymic activity of a phosphoenolpyruvate carboxykinase.

A phosphoenolpyruvate carboxykinase means a protein which exhibits the enzymatic activity of converting oxaloacetate into phosphoenolpyruvate.

Correspondingly, phosphoenolpyruvate carboxykinase activity means the quantity of oxaloacetate converted by the phosphoenolpyruvate carboxykinase protein, or quantity of phosphoenolpyruvate formed, in a particular time.

When the phosphoenolpyruvate carboxykinase activity is reduced compared with the wild type, therefore, the quantity of oxaloacetate converted by the phosphoenolpyruvate carboxykinase protein, or the quantity of phosphoenolpyruvate formed, in a particular time, is reduced compared with the wild type.

A reduction in phosphoenolpyruvate carboxykinase activity comprises a quantitative decrease in a phosphoenolpyruvate carboxykinase as far as a substantially complete absence of phosphoenolpyruvate carboxykinase (i.e. lack of detectability of phosphoenolpyruvate carboxykinase activity or lack of immunological detectability of phosphoenolpyruvate carboxykinase). The phosphoenolpyruvate carboxykinase activity is preferably reduced, compared with the wild type, by at least 5%, further preferably by at least 20%, further preferably by at least 50%, further preferably by 100%. In particular, "reduction" also means the complete absence of phosphoenolpyruvate carboxykinase activity.

The additional increasing of activities can take place in various ways, for example by switching off inhibitory regulatory mechanisms at the expression and protein level or by increasing gone expression of nucleic acids encoding the proteins described above compared with the wild type.

Increasing the gene expression of the nucleic acids encoding the proteins described above compared with the wild type can likewise take place in various ways, for example by inducing the gene by activators or, as described above, by increasing the promoter activity or increasing the expression activity or by introducing one or more gene copies into the microorganism.

Increasing the gene expression of a nucleic acid encoding a protein also means according to the invention manipulation of the expression of endogenous proteins intrinsic to the microorganism.

This can be achieved for example, as described above, by altering the promoter and/or expression unit sequences of the genes. Such an alteration, which results in an increased expression rate of the gene, can take place for example by deletion or insertion of DNA sequences.

It is possible, as described above, to alter the expression of endogenous proteins by applying exogenous stimuli. This can take place through particular physiological conditions, i.e. through the application of foreign substances.

The skilled worker may have recourse to further different procedures, singly or in combination, to achieve an increase in gene expression. Thus, for example, the copy number of the appropriate genes can be increased, or the promoter and regulatory region or the ribosome binding site located upstream of the structural gene can be mutated. It is additionally possible to increase the expression during fermentative production through inducible promoters. Procedures to prolong the lifespan of the mRNA likewise improve expression. Enzymic activity is likewise enhanced also by preventing degradation of enzyme protein. The genes or gene constructs may be either present in plasmids with varying copy number or integrated and amplified in the chromosome. It is also possible as an alternative to achieve overexpression of the relevant genes by altering the composition of the media and management of the culture.

The skilled worker can find guidance on this inter alia in Martin et al. (Biotechnology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in European patent 0472869, in U.S. Pat. No. 4,601,893, in Schwarzer and Puhler (Biotechnology 9, 84-87 (1991), in Reinscheid et al. (Applied and Environmental Microbiology 60, 126-132 (1994), in LaBarre et al. (Journal of Bacteriology 175, 1001-1007 (1993)), in the patent application WO 96/15246, in Malumbres et al. (Gene 134, 15-24 (1993)), in the Japanese published specification JP-A-10-229891, in Jensen and Hammer (Biotechnology and Bioengineering 58, 191-195 (1998)), in Makrides (Microbiological Reviews 60: 512-538 (1996) and in well-known textbooks of genetics and molecular biology.

It may additionally be advantageous for the production of biosynthetic products, especially L-lysine, L-methionine and L-threonine, besides the expression or enhancement of a gene, to eliminate unwanted side reactions (Nakayama, "Breeding of Amino Acid Producing Microorganisms", in: Overproduction of Microbial Products, Krumphanzl, Sikyta, Vanek (eds.), Academic Press, London, UK, 1982).

In a preferred embodiment, gene expression of a nucleic acid encoding one of the proteins described above is increased by introducing at least one nucleic acid encoding a corresponding protein into the microorganism. The introduction of the nucleic acid can take place chromosomally or extrachromosomally, i.e, through increasing the copy number on the chromosome and/or a copy of the gene on a plasmid which replicates in the host microorganism.

The introduction of the nucleic acid, for example in the form of an expression cassette comprising the nucleic acid, preferably takes place chromosomally, in particular by the SacB method described above.

It is possible in principle to use for this purpose any gene which encodes one of the proteins described above.

In the case of genomic nucleic acid sequences from eukaryotic sources which comprise introns, if the host microorganism is unable or cannot be made able to express the corresponding proteins it is preferred to use nucleic acid sequences which have already been processed, such as the corresponding cDNAs.

Examples of the corresponding genes are listed in Table 1 and 2.

The activities described above in microorganisms are preferably reduced by at least one of the following methods:

- introduction of at least one sense ribonucleic acid sequence for inducing cosuppression or of an expression cassette ensuring expression thereof
- introduction of at least one DNA- or protein-binding factor against the corresponding gene, RNA or protein or of an expression cassette ensuring expression thereof
- introduction of at least one viral nucleic acid sequence which causes RNA degradation, or of an expression cassette ensuring expression thereof
- introduction of at least one construct to produce a loss of function, such as, for example, generation of stop codons or a shift in the reading frame, of a gene for example by producing an insertion, deletion, inversion or mutation in a gene. It is possible and preferred to generate knockout mutants by targeted insertion into the desired target gene through homologous recombination or introduction of sequence-specific nucleases against the target gene.
- introduction of a promoter with reduced promoter activity or of an expression unit with reduced expression activity.

The skilled worker is aware that further methods can also be employed within the scope of the present invention for reducing its activity or function. For example, the introduction of a dominant negative variant of a protein or of an expression cassette ensuring expression thereof may also be advantageous.

It is moreover possible for each single one of these methods to bring about a reduction in the quantity of protein, quantity of mRNA and/or activity of a protein. A combined use is also conceivable. Further methods are known to the skilled worker and may comprise impeding or suppressing the processing of the protein, of the transport of the protein or its mRNA, inhibition of ribosome attachment, inhibition of RNA splicing, induction of an RNA-degrading enzyme and/or inhibition of translation elongation or termination.

In the method of the invention for producing biosynthetic products, the step of cultivation of the genetically modified microorganisms is preferably followed by an isolation of biosynthetic products from the microorganisms or/or from the fermentation broth. These steps may take place at the same time and/or preferably after the cultivation step.

The genetically modified microorganisms of the invention can be cultivated to produce biosynthetic products, in particular L-lysine, L-methionine and L-threonine, continuously or discontinuously in a batch method (batch cultivation) or in the fed batch or repeated fed batch method. A summary of known cultivation methods is to be found in the textbook by Chmiel (Bioprozeβtechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy in a suitable manner the demands of the respective strains. There are descriptions of culture media for various microorganisms in the handbook "Manual of Methods for General Bacteriology" of the American Society for Bacteriology (Washington D.C., USA, 1981).

These media which can be employed according to the invention usually comprise one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, ribose, sorbose, ribulose, lactose, maltose, sucrose, raffinose, starch or cellulose. Sugars can be put in the media also via complex compounds such as molasses, or other by-products of sugar refining. It may also be advantageous to add mixtures of various carbon sources. Other possible carbon sources are oils and fats such as, for example, soybean oil, sunflower oil, peanut oil and coconut fat, fatty acids such as, for example, palmitic acid, stearic acid or linoleic acid, alcohols such as, for example, glycerol, methanol or ethanol and organic acids such as, for example, acetic acid or lactic acid.

Nitrogen sources are usually organic or inorganic nitrogen compounds or materials containing these compounds. Examples of nitrogen sources include ammonia gas or ammonium salts such as ammonium sulfate, ammonium chloride, ammonium phosphate, ammonium carbonate or ammonium nitrate, nitrates, urea, amino acids or complex nitrogen sources such as corn steep liquor, soybean flour, soybean protein, yeast extract, meat extract and others. The nitrogen sources may be used singly or as mixtures.

Inorganic salt compounds which may be present in the media comprise the chloride, phosphoric or sulfate salts of calcium, magnesium, sodium, cobalt, molybdenum, potassium, manganese, zinc, copper and iron.

For producing fine chemicals, especially methionine, it is possible to use as sulfur source inorganic compounds such as, for example, sulfates, sulfites, dithionites, tetrathionates, thiosulfates, sulfides, but also organic sulfur compounds such as mercaptans and thiols.

It is possible to use as phosphorus source phosphoric acid, potassium dihydrogenphosphate or dipotassium hydrogenphosphate or the corresponding sodium-containing salts.

Chelating agents can be added to the medium in order to keep the metal ions in solution. Particularly suitable chelating agents comprise dihydroxyphenols such as catechol or protocatechuate, or organic acids such as citric acid.

The fermentation media employed according to the invention normally also comprise other growth factors such as vitamins or growth promoters, which include for example biotin, riboflavin, thiamine, folio acid, nicotinic acid, pantothonate and pyridoxine. Growth factors and salts are frequently derived from complex components of the media, such as yeast extract, molasses, corn steep liquor and the like. Suitable precursors may also be added to the culture medium. The exact composition of the compounds in the media depends greatly on the particular experiment and will be decided individually for each specific case. Information on optimization of media is obtainable from the textbook "Applied Microbiol. Physiology, A Practical Approach" (editors P. M. Rhodes, P. F. Stanbury, IRL Press (1997) pp. 53-73, ISBN 0 19 963577 3). Growth media can also be purchased from commercial suppliers, such as Standard 1 (Merck) or BHI (Brain heart infusion, DIFCO) and the like.

All the components of the media are sterilized either by heat (20 min at 1.5 bar and 121° C.) or by sterilizing filtration. The components can be sterilized either together or, if necessary, separately. All the components of the media may be present at the start of culturing or optionally be added continuously or batchwise.

The temperature of the culture is normally between 15° C. and 45° C., preferably at 25° C. to 40° C. and can be kept constant or changed during the experiment. The pH of the medium should be in the range from 5 to 8.5, preferably around 7.0. The pH for the culturing can be controlled during the culturing by adding basic compounds such as sodium hydroxide, potassium hydroxide, ammonia or aqueous ammonia or acidic compounds such as phosphoric acid or sulfuric acid. The development of foam can be controlled by employing antifoams such as, for example, fatty acid polyglycol esters. The stability of plasmids can be maintained by adding to the medium suitable substances with a selective action, such as, for example, antibiotics. Aerobic conditions are maintained by introducing oxygen-containing gas mixtures such as, for example, ambient air into the culture. The temperature of the culture is normally 2000 to 45° C. The culture is continued until formation of the desired product is at a maximum. This aim is normally reached within 10 hours to 160 hours.

The dry matter content of the fermentation broths obtained in this way is normally from 7.5 to 25% by weight.

It is additionally advantageous also to run the fermentation with sugar limitation at least at the end, but in particular over at least 30% of the fermentation time. This means that the concentration of utilizable sugar in the fermentation medium is kept at 0 to 3 g/l, or is reduced, during this time.

Biosynthetic products are isolated from the fermentation broth and/or the microorganisms in a manner known per se in accordance with the physical/chemical properties of the required biosynthetic product and the biosynthetic by-products.

The fermentation broth can then be processed further for example. Depending on the requirement, the biomass can be removed wholly or partly from the fermentation broth by separation methods such as, for example, centrifugation, filtration, decantation or a combination of these methods, or left completely in it, The fermentation broth can then be concentrated by known methods such as, for example, with the aid of a rotary evaporator, thin-film evaporator, falling-film evaporator, by reverse osmosis or by nanofiltration. This concentrated fermentation broth can then be worked up by freeze drying, spray drying, spray granulation or by other methods.

However, it is also possible to purify the biosynthetic products, especially L-lysine, L-methionine and L-threonine, further. For this purpose, the product-containing broth is subjected, after removal of the biomass, to a chromatography using a suitable resin, with the desired product or the impurities being retained wholly or partly on the chromatography resin. These chromatographic steps can be repeated if required, using the same or different chromatography resins. The skilled worker is proficient in the selection of suitable chromatography resins and their most effective use. The purified product can be concentrated by filtration or ultrafiltration and be stored at a temperature at which the stability of the product is a maximum.

The biosynthetic products may result in various forms, for example in the form of their salts or esters.

The identity and purity of the isolated compound(s) can be determined by prior art techniques. These comprise high performance liquid chromatography (HPLC), spectroscopic methods, staining methods, thin-layer chromatography, NIRS, enzyme assay or microbiological assays. These analytical methods are summarized in: Patek et al. (1994) Appl. Environ. Microbiol. 60:133-140; Malakhova et al. (1996) Biotekhnologlya 11 27-32; and Schmidt et al. (1998) Bioprocess Engineer. 19:67-70. Ulmann's Encyclopedia of Industrial Chemistry (1008) vol. A27, VCH: Weinheim, pp. 80-90, pp. 521 540, pp. 540-547, pp. 559-566, 575-581 and pp. 581-587; Michal, G (1999) Biochemical Pathways: An Atlas of Biochemistry and Molecular Biology, John Wiley and Sons: Fallon, A. et al. (1987) Applications of HPLC in Biochemistry in: Laboratory Techniques in Biochemistry and Molecular Biology, vol. 17.

The invention is now described in more detail by means of the following nonlimiting examples:

Example 1

Preparation of an Integrated Plasmid for Overexpression of the pycA Gene with the Aid of the Heterologous Expression Unit Pgro SEQ. ID. 2

The following oligonucleotides were defined for amplification of the promoter of the gene which codes for chaperonin Gro ES.

```
SEQ. ID. NO 5:
gro3:    5'-gccgcagcaaacccagtag-3'

SEQ. ID. NO. 6:
gro11:   5'-agtcgacacgatgaatccctccatgagaaaa-3'
```

The primers were employed in a PCR reaction with chromosomal DNA from C. glutamicum ATCC13032. It was possible with this approach to amplify a DNA fragment which corresponded to the expected size of 427 bp.

The following oligonucleotides were defined for amplification of a part of the gene which codes for pyruvate carboxylase.

```
SEQ. ID. NO. 7:
pyc6:
5'-tttttctcatggagggattcatcgtgtcgactcacacatcttcaacg

cttccag-3'

SEQ. ID. NO. 8:
pyc3:
5'-cccgcagcaacgcacgcaagaaa-3'
```

The primers were employed in a PCR reaction with chromosomal DNA from *C. glutamicum* ATCC13032. It was possible with this approach to amplify a DNA fragment which corresponded to the expected size of 1344 bp.

The primers gro11 and pyc6 contain an overlapping sequence and are homologous to one another at their 5' ends. The PCR products obtained above were employed as template for a further PCR in which the following primers were used.

```
SEQ. ID. NO. 9:
gro12: 5'-gcattcgcgccgctcgtaacta-3'

SEQ. ID. NO. 10:
pyc11: 5'-ggttcccgcgccctggtaa-3'
```

It was possible with this approach to amplify a DNA fragment which corresponded to the expected size of 1107 bp. This Pgro/pycA fusion was then cloned into the vector pCR2.1 (from Invitrogen GmbH, Karlsruhe, Germany). In a further step, the Pgro/pycA fusion was cloned from the plasmid pCR2.1 (from Invitrogen GmbH, Karlsruhe, Germany) as 1125 hp EcoRI fragment into the integration vector pK19 mob sacB SEQ ID NO 11, which had previously been cut with the restriction endonuclease. The resulting plasmid was referred to as pk19 mob sacB Pgro/pycA.

The following oligonucleotides were defined for amplification of a 5' region of the pycA gene:

```
SEQ. ID. NO. 12:
pyc14: 5'-ccggcgaagtgtctgctcgcgtga-3'

SEQ. ID. NO. 13:
pyc15: 5'-accccgccccagtttttc-3'
```

The primers were employed in a PCR reaction with chromosomal DNA from *C. glutamicum* ATCC13032. It was possible with this approach to amplify a DNA fragment which corresponded to the expected size of 487 bp. This DNA fragment was cloned into the vector pCR2.1 (from Invitrogen GmbH, Karlsruhe, Germany). A 593 bp SpeI/XbaI fragment was then subsequently cloned into the vector pK19 mob sacB Psod ask, which had previously been digested with the restriction enzyme NheI. The resulting plasmid was referred to as pK19 mob sacB Pgro pycA+US (SEQ. ID. NO. 14). Up to this step, all clonings were carried out in *Escherichia coli* XL-1 Blue (from Stratagene, Amsterdam, Netherlands).

The transformation plasmid pK19 mob sacB Pgro pycA+US was then used to transform *E. coli* Mn522 (from Stratagene, Amsterdam, Netherlands) together with the plasmid pTc15AcgIM as described by Liebl et al. (1989) FEMS Microbiology Letters 53:299-303. The plasmid pTc15AcgIM enables DNA to be methylated according to the methylation pattern of *Corynebacterium glutamicum* (DE 10046870). This step enables *Corynebacterium glutamicum* subsequently to undergo electroporation with the integration plasmid pK19 mob sacB Pgro pycA+US. This electroporation and the subsequent selection on CM plates (10 μl glucose; 2.5 μl NaCl; 2 g/l urea, 10 g/l Bacto Peptone (Difco); 10 g/l yeast extract, 22.0 g/l agar (Difco)) with kanamycin (25 μg/ml) resulted in a plurality of transconjugants.

To select for the second recombination event, which should lead to excision of the vector together with the pycA promoter and the pycA gone, these transconjugants were cultured in CM medium without kanamycin overnight and then plated out on CM plates with 10% sucrose for selection. The sacB gene present on the vector pK19 mob sacB codes for the enzyme levansucrase and leads to the synthesis of levan on growth on sucrose. Since levan is toxic for *C. glutamicum*, the only *C. glutamicum* cells able to grow on sucrose-containing medium are those which have lost the integration plasmid through the second recombination step (Jäger et al., Journal of Bacteriology 174 (1992) 5462-5466). 100 sucrose-resistant clones were examined for their kanamycin sensitivity. It was possible to demonstrate for 15 of the tested clones not only resistance to sucrose but also sensitivity to kanamycin. A polymerase chain reaction (PCR) was used to check whether the desired replacement of the natural expression unit by the Pgro expression unit had also taken place. Chromosomal DNA was isolated from the initial strain and the 15 clones for this analysis. For this purpose, the respective clones were removed from the agar plate with a toothpick and suspended in 100 μl of $H_2O$ and boiled at 95° C. for 10 min. 10 μl portions of the resulting solution were employed as template in the PCR. The primers used were oligonucleotides which are homologous to the Pgro expression unit and the pycA gene.

The PCR conditions were chosen as follows: predenaturation: 5 min at 95° C.; denaturation 30 sec at 9500; hybridization 30 sec at 56° C.; amplification 1 min at 72° C.; 30 cycles; final extension 5 min at 72° C. In the mixture with the DNA of the initial strain it was not possible for a PCR product to result owing to the choice of the oligonucleotides. Only with clones in which the second recombination effected replacement of the natural expression unit (PpycA) by Pgro was a band with a size of 310 bp expected. In total, 7 of the tested 15 clones were positive.

The 7 positive clones and the initial strain were then cultured in 10 ml of CM medium (10 glucose; 2.5 g/l NaCl; 2 g/l urea, 10 g/l Bacto Peptone (Difco); 10 g/l yeast extract) overnight. The cells were then pelleted and taken up in 0.5 ml of buffer (50 mM Tris, 10 mM $MgCl_2$, 50 mM KCl; pH 7.7). The cells were disrupted with the aid of a Ribolyzer (3×30 sec at level 6, from Hybaid). After a protein determination by the Bradford method, 15 μg portions of protein were loaded onto a 10% SDS gel, and the proteins were fractionated. An increased amount of PycA protein was detectable compared with the initial strain (FIG. 1). FIG. 1 shows a 10% SDS gel of the Pgro pycA clones.

Example 2

Preparation of the Vector pCLiK5MCS

Firstly, the ampicillin resistance and origin of replication of the vector pBR322 were amplified by the polymerase chain reaction (PCR) using the oligonucleotide primers SEQ ID NO: 15 and SEQ ID NO: 16.

```
                                         SEQ ID NO: 15
5'-CCCGGGATCCGCTAGCGGCGCGCCGGCCGGCCCGGTGTGAAATACCG

CACAG-3'

                                         SEQ ID NO: 16
5'-TCTAGACTCGAGCGGCCGCGGCCGGCCTTTAAATTGAAGACGAAAGG

GCCTCG-3'
```

Besides the sequences complementary to pBR322, the oligonucleotide primer SEQ ID NO: 15 contains in the 5'-3' direction the cleavage sites for the restriction endonucleases SmaI, BamHI, NheI and AscI and the oligonucleotide primer SEQ ID NO: 16 contains in the 5'-3' direction the cleavage sites for the restriction endonucleases XbaI, XhoI, NotI and DraI. The PCR reaction was carried out with PfuTurbo polymerase (Stratagene, La Jolla, USA) by a standard method such as Innis et al. (PCR Protocols. A Guide to Methods and Applications, Academic Press (1990)). The resulting DNA fragment with a size of approximately 2.1 kb as purified using the GFX™ PCR, DNA and Gel Band purification kit (Amersham Pharmacia, Freiburg) in accordance with the manufacturer's instructions. The blunt ends of the DNA fragment were ligated together using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor (1989)). Plasmid-harboring cells were selected by plating out on LB agar (Lennox, 1955, Virology, 1:190) containing ampicillin (50 μg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK1.

Starting from the plasmid pWLT1 (Liebl et al., 1992) as template for a PCR reaction, a kanamycin resistance cassette was amplified using the oligonucleotide primers SEQ ID NO: 17 and SEQ ID NO: 18.

```
SEQ ID NO: 17:
5'-GAGATCTAGACCCGGGGATCCGCTAGCGGGCTGCTAAAGGAAGCGG

A-3'

SEQ ID NO: 18:
5'-GAGAGGCGCGCCGCTAGCGTGGGCGAAGAACTCCAGCA-3'
```

Besides the sequences complementary to pWLT1, the oligonucleotide primer SEQ ID NO: 17 contains in the 5'-3' direction the cleavage sites for the restriction endonucleases XbaI, SmaI, BamHI, NheI and the oligonucleotide primer SEQ ID NO. 18 contains in the 5'-3' direction the cleavage sites for the restriction endonucleases AscI and NheI. The PCR reaction was carried out with PfuTurbo polymerase (Stratagene, La Jolla, USA) by standard methods such as Innis et al. (PCR Protocols. A Guide to Methods and Applications, Academic Press (1990)). The resulting DNA fragment with a size of approximately 1.3 kb was purified using the GFX™ PCR, DNA and Gel Band purification kit (Amersham Pharmacia, Freiburg) in accordance with the manufacturer's instructions. The DNA fragment was cut with the restriction endonucleases XbaI and AscI (New England Biolabs, Beverly, USA) and subsequently again purified using the GFX™ PCR, DNA and Gel Band purification kit (Amersham Pharmacia, Freiburg) in accordance with the manufacturer's instructions. The vector pCLiK1 was likewise cut with the restriction endonucleases XbaI and Asci and dephosphorylated with alkaline phosphatase (I (Roche Diagnostics, Mannheim)) in accordance with the manufacturer's instructions. After electrophoresis in a 0.8% agarose gel, the linearized vector (approx. 2.1 kb) was isolated using the GFX™ PCR, DNA and Gel Band purification kit (Amersham Pharmacia, Freiburg) in accordance with the manufacturer's instructions. This vector fragment was ligated with the cut PCR fragment using the rapid DNA ligation kit (Roche Diagnostics, Mannheim) in accordance with the manufacturers instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing ampicillin (50 μg/ml) and kanamycin (20 μg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK2.

The vector pCLiK2 was cut with the restriction endonuclease DraI (New England Biolabs, Beverly, USA). After electrophoresis in a 0.8% agarose gel, a vector fragment approx 2.3 kb in size was isolated using the GFX™ PCR, DNA and Gel Band purification kit (Amersham Pharmacia, Freiburg) in accordance with the manufacturer's instructions. This vector fragment was religated using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK3.

Starting from the plasmid pWLQ2 (Liebl et al., 1992) as template for a PCR reaction, the origin of replication pHM1519 was amplified using the oligonucleotide primers SEQ ID NO: 19 and SEQ ID NO: 20.

```
SEQ ID NO: 19:
5'-GAGAGGGCGGCCGCGCAAAGTCCCGCTTCGTGAA-3'

SEQ ID NO: 20:
5'-GAGAGGGCGGCCGCTCAAGTCGGTCAAGCCACGC-3'
```

Besides the sequences complementary to pWLQ2, the oligonucleotide primers SEQ ID NO: 19 and SEQ ID NO: 20 contain cleavage sites for the restriction endonuclease NotI. The PCR reaction was carried out with PfuTurbo polymerase (Stratagene, La Jolla, USA) by a standard method such as Innis et al. (PCR Protocols. A Guide to Methods and Applications, Academic Press (1990)). The resulting DNA fragment with a size of approximately 2.7 kb was purified using the GFX™ PCR, DNA and Gel Band purification kit (Amersham Pharmacia, Freiburg) in accordance with the manufacturer's instructions. The DNA fragment was cut with the restriction endonuclease NotI (New England Biolabs, Beverly, USA) and then again purified with the GFX™ PCR, DNA and Gel Band purification kit (Amersham Pharmacia, Freiburg) in accordance with the manufacturer's instructions. The vector pCLiK3 was likewise cut with the restriction endonuclease NotI and dephosphorylated with alkaline phosphatase (I (Roche Diagnostics, Mannheim)) in accordance with the manufacturer's instructions. After electrophoresis in a 0.8% agarose gel, the linearized vector (approx. 2.3 kb) was isolated with the GFX™ PCR, DNA and Gel Band purification kit (Amersham Pharmacia, Freiburg) in accordance with the manufacturer's instructions. This vector fragment was ligated with the cut PCR fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA of an individual clone was isolated using the Qiaprep spin miniprep kit (Qiagen, Hilden) in accordance with the manufacturer's instructions and checked by restriction digestions. The plasmid obtained in this way is called pCLiK5

To extend pCLiK5 by a multiple cloning site (MCS), the two synthetic, very substantially complementary oligonucleotides SEQ ID NO: 21 and SEQ ID NO: 22, which contain cleavage sites for the restriction endonucleases SwaI, XhoI, AatI, ApaI, Asp718, MluI, NdeI, SpeI, EcoRV, SalI, ClaI, BamHI, XbaI and SmaI, were combined by heating together at 95° C. and slow cooling to give a double-stranded DNA fragment.

```
SEQ ID NO: 21:
5'-TCGAATTTAAATCTCGAGACCCCTCACGTCGGGCCCGGTACCACGCG

TCATATGACTAGTTCGGACCTAGGGATATCGTCGACATCGATGCTCTTCT

GCGTTAATTAACAATTGGGATCCTCTAGACCCGGGATTTAAAT-3'

SEQ ID NO: 22:
5'-GATCATTTAAATCCCGGGTCTAGAGGATCCCAATTGTTAATTAACGC

AGAAGAGCATCGATGTCGACGATATCCCTAGGTCCGAACTAGTCATATGA

CGCGTGGTACCGGGCCCGACGTCAGGCCTCTCGAGATTTAAAT-3'
```

The vector pCLiK5 was cut with the restriction endonucleases XhoI and BamHI (New England Biolabs, Beverly, USA) and dephosphorylated with alkaline phosphatase (I (Roche Diagnostics, Mannheim)) in accordance with the manufacturers instructions. After electrophoresis in a 0.8% agarose gel, the linearized vector (approx. 5.0 Kb) was Isolated with the GFX™ PCR, DNA and Gel Band purification kit (Amersham Pharmacia, Freiburg) in accordance with the manufacturer's instructions. This vector fragment was ligated to the synthetic double-stranded DNA fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA of an individual clone was isolated using the Qiaprep spin miniprep kit (Qiagen, Hilden) in accordance with the manufacturers instructions and checked by restriction digestions. The plasmid obtained in this way is called pCLiK5MCS.

Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmid pCLiK5MCS is listed as SEQ ID NO: 23.

Example 3

Preparation of the Plasmid PmetA metA

Chromosomal DNA was prepared from *C. glutamicum* ATCC 13032 as described by Tauch et al. (1995) Plasmid 33:168-179 or Eikmanns et al. (1994) Microbiology 140: 1817-1828. The metA gene including the noncoding 5' region was amplified by the polymerase chain reaction (PCR) by standard methods as described in Innis et al. (1990) PCR Protocols. A Guide to Methods and Applications, Academic Press, using the oligonucleotide primers SEQ ID NO: 24 and SEQ ID NO. 25, the chromosomal DNA as template and Pfu Turbo polymerase (from Stratagene).

```
SEQ ID NO: 24 5'-GCGCGGTACCTAGACTCACCCCAGTGCT-3'
and

SEQ ID NO: 25 5'-CTCTACTAGTTTAGATGTAGAACTCGATGT-3'
```

The resulting DNA fragment with a size of approx. 1.3 kb was purified using the GFX™ PCR, DNA and Gel Band purification kit (Amersham Pharmacia, Freiburg) in accordance with the manufacturer's instructions. It was then cleaved with the restriction enzymes Asp718 and SpeI (Roche Diagnostics, Mannheim) and the DNA fragment was purified with the GFX™ PCR, DNA and Gel Band purification kit.

The vector pClik5MCS SEQ ID NO: 23 was cut with the restriction enzymes Asp718 and SpeI and, after fractionation by electrophoresis, a fragment 5 kb in size was isolated using the GFX™ PCR, DNA and Gel Band purification kit.

The vector fragment was ligated together with the PCR fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA was prepared by methods and using materials from Qiagen. Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmid pCLiK5MCS PmetA meta is listed as SEQ ID NO: 26.

Example 9

Preparation of the Plasmid pCLiK5MCS Pgro metA

Chromosomal DNA was prepared from *C. glutamicum* ATCC 13032 as described by Tauch et al. (1995) Plasmid 33: 168-179 or Eikmanns et al. (1994) Microbiology 140:1817-1828. A DNA fragment of approx. 200 base pairs from the noncoding 5' region (region of the expression unit) of the gene GroES (Pgro) was amplified by the polymerase chain reaction (PCR) by standard methods such as Innis et al. (1990) PCR Protocols, A Guide to Methods and Applications, Academic Press, using the oligonucleotide primers SEQ ID NO: 27 and SEQ ID NO: 28, the chromosomal DNA as template and Pfu Turbo polymerase (from Stratagene).

```
                                          SEQ ID NO: 27
5'-GAGACTCGAGCGGCTTAAAGTTTGGCTGCC-3'
and

                                          SEQ ID NO: 28
5'-CCTGAAGGCGCGAGGGTGGGCATGATGAATCCCTCCATGAG-3'
```

The resulting DNA fragment was purified with the GFX™ PCR, DNA and Gel Band purification kit (Amersham Pharmacia, Freiburg) in accordance with the manufacturer's instructions.

Starting from plasmid PmetA meta as template for a PCR reaction, a part of meta was amplified using the oligonucleotide primers SEQ ID NO: 29 and SEQ ID NO: 30.

```
SEQ ID NO: 29      5'-CCCACCCTCGCGCCTTCAG-3'
and

SEQ ID NO: 30      5'-CTGGGTACATTGCGGCCC-3'
```

The resulting DNA fragment of approximately 470 base pairs was purified with the GFX™ PCR, DNA and Gel Band purification kit in accordance with the manufacturer's instructions.

In a further PCR reaction, the two fragments obtained above were employed together as template. Owing to the sequences which have been introduced with the oligonucleotide primer SEQ ID NO: 28 and are homologous to metA, during the PCR reaction the two fragments are attached to one another and extended to give a continuous DNA strand by the polymerase employed. The standard method was modified by adding the oligonucleotide primers used SEQ ID NO: 27 and SEQ ID NO: 30, to the reaction mixture only at the start of the second cycle.

The amplified DNA fragment of approximately 675 base pairs was purified using the GFX™ PCR, DNA and Gel Band purification kit in accordance with the manufacturer's instructions. It was then cleaved with the restriction enzymes XhoI and NcoI (Roche Diagnostics, Mannheim) and fractionated by gel electrophoresis. Subsequently, the DNA fragment approximately 620 base pairs in size was purified from the agarose using the GFX™ PCR, DNA and Gel Band purification kit (Amersham Pharmacia, Freiburg) The plasmid PmetA meta SEQ ID NO: 26 was cleaved with the restriction enzymes NcoI and SpeI (Roche Diagnostics, Mannheim). After fractionation by gel electrophoresis, a metA fragment approximately 0.7 kb in size was purified from the agarose using the GFX™ PCR, DNA and Gel Band purification kit.

The vector pClik5MCS SEQ ID NO: 23 was cut with the restriction enzymes XhoI and SpeI (Roche Diagnostics, Mannheim) and, after fractionation by electrophoresis, a fragment 5 kb in size was isolated using the GFX™ PCR, DNA and Gel Band purification kit.

The vector fragment was ligated together with the PCR fragment and the metA fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA was prepared by methods and using materials from Qiagen. Sequencing reactions were carried out as described by Sanger et al. (1977) Proceedings of the National Academy of Sciences USA 74; 5463-5467. The sequencing reactions were fractionated and evaluated using an ABI prism 377 (PE Applied Biosystems, Weiterstadt).

The resulting plasmid pCLiK5MCS PGroESmetA is listed as SEQ ID NO: 31.

Example 10

MetA Activities

The strain *Corynebacterium glutamicum* ATCC13032 was transformed with each of the plasmids pClik5 MCS, pClik MCS PmetA metA, pCLiK5MCS PGroESmetA by the method described (Liebl, et al. (1989) FEMS Microbiology Letters 53:299-303). The transformation mixture was plated on CM plates which additionally contained 20 mg/l kanamycin in order to select for plasmid-containing cells. Resulting Kan-resistant clones were picked and isolated.

*C. glutamicum* strains which contained one of these plasmid constructs were cultured in MMA medium (40 g/l sucrose. 20 g/l $(NH_4)_2SO_4$, 1 g/l $KH_2PO_4$, 1 g/l $K_2HPO_4$, 0.25 g/l $MgSO_4 \times 7H_2O$, 54 g Aces, 1 ml $CaCl_2$ (10 g/l), 1 ml protocatechuate (300 mg/10 ml), 1 ml trace element solution (10 g/l $FeSO_4 \times 7H_2O$, 10 g/l $MnSO_4 \times H_2O$, 2 g/l $ZnSO_4 \times 7H_2O$, 0.2 g/i $CuSO_4$, 0.02 g/l $NiCl_2 \times 6H_2O$), 100 μg/l vitamin $B_{12}$, 0.3 mg/l thiamine, 1 mM leucine, 1 mg/l pyridoxal HCl, 1 ml biotin (100 mg/l), pH 7.0) at 30° C. overnight. The cells were spun down at 4° C. and then washed twice with cold Tris-HCl buffer (0.1%, pH 8.0). After renewed centrifugation, the cells were taken up in cold Tris-HCl buffer (0.1%, pH 8.0) and adjusted to an $OD_{600}$ of 160. For cell disruption, 1 ml of this cell suspension was transferred into 2 ml Ribolyser tubes from Hybaid and lysed in a Ribolyser from Hybaid with a rotation setting of 6.0 three times for 30 sec each time. The lysate was clarified by centrifugation at 15 000 rpm and 4° C. in an Eppendorf centrifuge for 30 minutes, and the supernatant was transferred into a new Eppendorf cup. The protein content was determined as described by Bradford, M. M. (1976) Anal. Biochem. 72:248-254.

The enzymatic activity of metA was determined as follows. The 1 ml reaction mixtures contained 100 mM potassium phosphate buffer (pH 7.5), 5 mM $MgCl_2$, 100 μM acetyl-CoA, 5 mM L-homoserine, 500 μM DTNB (Ellman's reagent) and cell extract. The assay was started by adding the respective protein lysate and incubated at room temperature. Kinetics were then recorded at 412 nm for 10 min.

The results are shown in Table 1a

TABLE 1a

| Strain | Specific activity [nmol/mg/min] |
|---|---|
| ATCC 13032 pClik5MCS | 12.6 |
| ATCC 13032 pClik5MCS PmetA metA | 50.7 |
| ATCC 13032 pCLiK5MCS PGroESmetA | 109.0 |

It was possible to increase MetA activity considerably by using the heterologous expression unit.

Example 11

Preparation of the Plasmid pClik5MCS metA Without Start Codon

Chromosomal DNA was prepared from *C. glutamicum* ATCC 13032 as described by Tauch et al. (1995) Plasmid 33:168-179 or Eikmanns et al. (1994) Microbiology 140: 1817-1828. The oligonucleotide primers SEQ ID NO 32 to SEQ ID NO 33, the chromosomal DNA as template and Pfu Turbo Polymerase (from Stratagene) were used in a polymerase chain reaction (PCR) by standard methods, as described in Innis et al. (1990) PCR Protocols. A Guide to Methods and Applications, Academic Press, to amplify the termination region of the groEL gene.

```
SEQ ID NO 32 5'-GGATCTAGAGTTCTGTGAAAAACACCGTG-3'

SEQ ID NO 33 5'-GCGACTAGTGCCCCACAAATAAAAAACAC-3'
```

The resulting DNA fragments about 60 bp in size were purified using the GFX™ PCR, DNA and Gel Band Purification Kit (Amersham Pharmacia, Freiburg) in accordance with the manufacturer's instructions. After this, it was cleaved with the restriction enzymes XbaI and BcnI (Roche Diagnostics, Mannheim), and the DNA fragment was purified using GFX™ PCR, DNA and G3 μl Band Purification Kit.

The vector pClik5MCS SEQ ID NO: 23 was cut with the restriction enzyme XbaI, and a fragment 5 kb in size was isolated after electrophoretic fractionation with GFX™ PCR, DNA and Gel Band Purification Kit.

The vector fragment was ligated together with the fragment 60 bp in size using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA was prepared by methods and using materials from Qiagen. Sequencing reactions were carried out as described by Sanger et al. (1977) Proceedings of the National Academy of Sciences USA 74:5483-6467. The sequencing reaction were fractionated and evaluated using an ABI prism 377 (PE Applied Biosystems, Weiterstadt).

The resulting plasmid pCLiK5MCS PgroES term is listed as SEQ ID NO: 34.

Chromosomal DNA was prepared from *C. glutamicum* ATCC 13032 as described by Tauch et al. (1995) Plasmid 33:168-179 or Eikmanns et al. (1994) Microbiology 140: 1817-1828. The oligonucleotide primers SEQ ID NO 35 and SEQ ID NO 36, the chromosomal DNA as template and Pfu Turbo Polymerase (from Stratagene) were used in a polymerase chain reaction (PCR) by standard methods, as described in Innis et al. (1990) PCR Protocols. A Guide to Methods and Applications, Academic Press, to amplify the meta gene without start codon.

```
SEQ ID NO 35 5'-GAGACATATGCCCACCCTCGCGCCTTCAGG-3'
and

SEQ ID NO 36 5'-CTCTACTAGTTTAGATGTAGAACTCGATGT-3'
```

The resulting DNA fragment about 1.2 kb in size was purified using the GFX™ PCR, DNA and Gel Band Purification Kit (Amersham Pharmacia, Freiburg) in accordance with the manufacturer's instructions. After this, it was cleaved with the restriction enzymes XbaI and BcnI) (Roche Diagnostics, Mannheim), and the DNA fragment was purified using GFX™ PCR, DNA and Gel Band Purification Kit.

The vector pClik5MCS groEL term SEQ ID NO, 34 was cut with the restriction enzymes NdeI and BcnI, and a fragment 5 kb in size was isolated after electrophoretic fractionation with GFX™ PCR, DNA and Gel Band Purification Kit.

The vector fragment was ligated together with the PCR fragment using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA was prepared by methods and using materials from Qiagen. Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmid pCLiK5MCS metA without start codon ist listed as SEQ ID NO, 37

Example 12

Construction of Pgro Expression Units with Different Specific Expression Activities Due to Different RBS Sequences and Distances of metA from the Start Codon Chromosomal DNA was prepared from *C. glutamicum* ATCC 13032 as described by Tauch et al. (1995) Plasmid 33:168-179 or Eikmanns et al. (1994) Microbiology 140: 1817-1828. The oligonucleotide primers SEQ ID NO 38 to SEQ ID NO 43, the chromosomal DNA as template and Pfu Turbo Polymerase (from Stratagene) were used in a polymerase chain reaction (PCR) by standard methods, as described in Innis et al. (1990) PCR Protocols. A Guide to Methods and Applications, Academic Press, to amplify the various expression units. In this case, the oligonucleotide primer 1701 (SEQ ID NO 38) was used as sense primer and was combined with the other oligonucleotide primers.

```
Oligonucleotide primer 1701
                                          SEQ ID NO 38
5'-GAGACTCGAGCGGCTTAAAGTTTGGCTGCC-3'

Oligonucleotide primer 1828
                                          SEQ ID NO 39
5'-ctctcatatgcAATCCCTCCATGAGAAAAATT-3'

Oligonucleotide primer 1831
                                          SEQ ID NO 40
5'-ctctcatatgcgcggccgcAATCCCTCCATGAGAAAAATT-3'

Oligonucleotide primer 1832
                                          SEQ ID NO 41
5'-ctctcatatgcAAtctctccATGAGAAAAATTTTGTGTG 3'

Oligonucleotide primer 1833
                                          SEQ ID NO 42
5'-ctctcatatgcAAtctcctcATGAGAAAAATTTTGTGTG-3'

Oligonucleotide primer 1834
                                          SEQ ID NO 43
5'-ctctcatatgcAAtcccttcATGAGAAAAATTTTGTGTG-3'
```

The resulting DNA fragments with a size of approx, 200 bp were purified using the GFX™ PCR, DNA and Gel Band Purification Kit (Amersham Pharmacia, Freiburg) in accordance with the manufacturer's instructions.

The vector pBS KS+ (SEQ ID NO: 44) was cut with the restriction enzyme EcoRV, and a fragment 2.9 kb in size was isolated after electrophoretic fractionation with GFX™ PCR, DNA and Gel Band Purification Kit.

The vector fragment was ligated together with the PCR fragments using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology, 1:190) containing kanamycin (20 μg/ml).

The plasmid DNA was prepared by methods and using materials from Qiagen. Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmids were called pKS Pgro 1701/1828, pKS Pgro 1701/1831, pKS Pgro 1701/1832, pKS Pgro 1701/1833 and pKS Pgro 1701/1834, These plasmids were then cut with the restriction enzymes NdeI and XhoI. The resulting DNA fragments approx. 200 bp in size were isolated and purified using the GFX™ PCR, DNA and Gel Band Purification Kit (Amersham Pharmacia, Freiburg) in accordance with the manufacturer's instructions.

The vector pCLiK5MCS metA without start codon SEQ ID NO: 37 was cut with the restriction enzymes NdeI and XhoI, and a fragment 5 kb in size was isolated after electrophoretic fractionation with GFX™ PCR, DNA and Gel Band Purification Kit.

The vector fragment was ligated together with the fragment 200 bp in size using the rapid DNA ligation kit (Roche Diagnostics, Mannheim) in accordance with the manufacturer's instructions, and the ligation mixture was transformed into competent *E. coli* XL-1 Blue (Stratagene, La Jolla, USA) by standard methods as described in Sambrook et al. (Molecular Cloning. A Laboratory Manual, Cold Spring Harbor, (1989)). Plasmid-harboring cells were selected by plating out on LB agar (Lennox, 1955, Virology. 1:190) containing kanamycin (20 μg/ml).

The plasmid DNA was prepared by methods and using materials from Qiagen. Sequencing reactions were carried out as described by Sanger et al. (1977) Proceedings of the National Academy of Sciences USA 74:5463-5467. The sequencing reactions were fractionated and evaluated using an ABI prism 377 (PE Applied Biosystems, Weiterstadt).

The resulting plasmids pCLiK5MCS Pgro 1701/1828 meta, pCLiK5MCS Pgro 1701/1831 meta, pCLiK5MCS Pgro 1701/1832 metA, pCLiK5MCS Pgro 1701/1833 metA and pCLiK5MCS Pgro 1701/1834 meta are listed as SEQ ID NO: 45 to 49.

Figure 2:
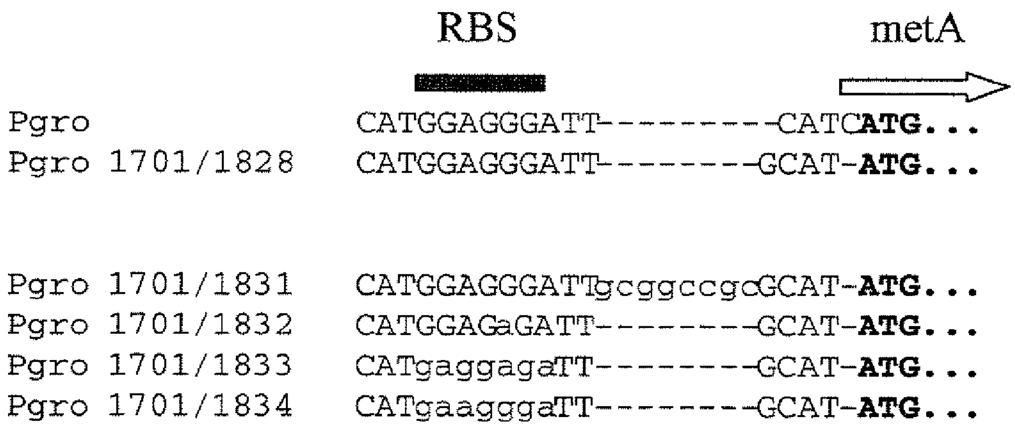
FIG. 2 represents the choice of oligonucleotides for altering the Pgro expression unit. Prgo (found within SEQ ID NO: 31), Pgro 1701/1828 (found within SEQ ID NO: 45), Pgro 1701/1831 (found within SEQ ID NO: 46), Pgro 1701/1832 (found within SEQ ID NO: 47), Pgro 1701/1833 (found within SEQ ID NO. 45), and Pgro 1701/1834 (found within SEQ ID NO: 49).

The Pgro expression unit was altered through the choice of the oligonucleotides as described in FIG. 2.

The strain *Corynebacterium glutamicum* ATCC13032 was transformed with each of the plasmids pClik5 MCS, pClik MOS Pgro metA, pCLiK5MCS Pgro 1701/1828 meta, pCLiK5MCS Pgro 1701/1831 metA, pCLiK5MCS Pgro 1701/1832 meta, pCLiK5MCS Pgro 1701/1833 metA and pCLiK5MCS Pgro 1701/1834 by the described method (Liebl, et al. (1989) FEMS Microbiology Letters 53:299-303). The transformation mixture was plated on GM plates which additionally contained 20 mg/l kanamycin in order to select for plasmid-containing cells. Resulting Kan-resistant clones were picked and isolated.

*C. glutamicum* strains which contained one of these plasmid constructs were cultured in MMA medium (40 g/l sucrose, 20 g/l $(NH_4)_2SO_4$, 1 μl $KH_2PO_4$, 1 g/l $K_2HPO_4$, 0.25 μl $MgSO_4 \times_7 H_2O$, 54 g Aces, 1 ml $CaCl_2$ (10 μl), 1 ml protocatechuate (300 mg/10 ml), 1 ml trace element solution (10 μl $FeSO_4 \times_7 H_2O$, 10 g/l $MnSO_4 \times H_2O$, 2 g/l $ZnSO_4 \times 7H_2O$, 0.2 g/l $CuSO_4$, 0.02 g/l $NiCl_2 \times 6H_2O$), 100 μg/l vitamin $B_{12}$, 0.3 mg/l thiamine, 1 mM leucine, 1 mg/l pyridoxal HCl, 1 ml biotin (100 mg/l), pH 7.0) at 30° C. for 5 h, The cells were spun down at 4° C. and then washed twice with cold Tris-HCl buffer (0.1%, pH 8.0). After renewed centrifugation, the cells were taken up in cold Tris-HCl buffer (0.1%, pH 8.0) and adjusted to an $OD_{600}$ of 160. For cell disruption, 1 ml of this sell suspension was transferred into 2 ml Ribolyser tubes from Hybaid and lysed in a Ribolyser from Hybaid with a rotation setting of 6.0 three times for 30 sec each time. The lysate was clarified by centrifugation at 15 000 rpm and 4° C. in an Eppendorf centrifuge for 30 minutes, and the supernatant was transferred into a new Eppendorf cup. The protein content was determined as described by Bradford, M. M, (1976) Anal. Biochem. 72:248-254.

The enzymatic activity of meta was determined as follows. The 1 ml reaction mixtures contained 100 mM potassium phosphate buffer (pH 7.5), 5 mM $MgCl_2$, 100 μM acetyl-CoA, 5 mM homoserine, 500 μM DTNB (Ellman's reagent) and cell extract. The assay was started by adding the respective protein lysate and incubated at room temperature. Kinetics were then recorded at 412 nm for 10 min.

The results are shown in table 2a.

TABLE 2a

| Strain | specific activity [nmol/mg/min] |
|---|---|
| ATCC 13032 pClik5MCS | 7.5 |
| ATCC 13032 pCLiK5MCS Pgro metA | 109.0 |
| ATCC 13032 pCLiK5MCS Pgro 1701/1828 metA | 30.6 |
| ATCC 13032 pCLiK5MCS Pgro 1701/1831 metA | 8.7 |
| ATCC 13032 pCLiK5MCS Pgro 1701/1832 metA | 60.6 |
| ATCC 13032 pCLiK5MCS Pgro 1701/1833 metA | 217.3 |
| ATCC 13032 pCLiK5MCS Pgro 1701/1835 metA | 96.3 |

We claim:

1. A genetically modified microorganism comprising:

a nucleic acid having promoter activity which regulates transcription of a gene in the microorganism, where the gene is heterologous to and functionally linked to the nucleic acid having promoter activity, and where the nucleic acid having promoter activity comprises a) a nucleic acid molecule comprising the nucleotide sequence of SEQ ID NO: 1; or b) a nucleic acid molecule comprising a nucleotide sequence having at least 98% identity to the entire nucleotide sequence of SEQ ID NO: 1;

where the microorganism is *Corynebacterium glutamicum*, and wherein the nucleic acid having promoter activity is introduced into the microorganism.

2. The genetically modified microorganism of claim 1, wherein the nucleic acid having promoter activity is introduced into the genome of the microorganism so that transcription of one or more endogenous genes takes place under the control of the introduced nucleic acid having promoter activity.

3. The genetically modified microorganism of claim 2, wherein introduction of the nucleic acid having promoter activity results in transcription of the one or more endogenous genes in the microorganism or results in an increased transcription rate of the one or more endogenous genes compared with the corresponding wild type microorganism.

4. The genetically modified microorganism of claim 3, wherein the microorganism has an increased transcription rate of the one or more endogenous genes compared with the corresponding wild type microorganism.

5. The genetically modified microorganism of claim 1, wherein the nucleic acid having promoter activity is introduced in a construct comprising the nucleic acid having promoter activity functionally linked to the gene.

6. The genetically modified microorganism of claim 5, wherein introduction of the construct results in transcription of the gene in the microorganism.

7. The genetically modified microorganism of claim 5, wherein the microorganism has an increased transcription rate of the gene compared with a microorganism in which the nucleic acid having promoter activity has not been introduced.

8. The genetically modified microorganism of claim 1, wherein the gene is selected from the group consisting of nucleic acids encoding a protein from the biosynthetic pathway of proteinogenic and non-proteinogenic amino acids, nucleic acids encoding a protein from the biosynthetic pathway of nucleotides and nucleosides, nucleic acid encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors, and nucleic acids encoding a protein from the biosynthetic pathway of enzymes, where the gene may comprise further regulatory elements.

9. The genetically modified microorganism of claim 8, wherein the protein is selected from the group consisting of aspartate kinase, aspartate-semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1,6-bisphosphatase, protein of sulfate reduction RXA077, protein of sulfate reduction RXA248, protein of sulfate reduction RXA247, protein OpcA, 1-phosphofructokinase, and 6-phosphofructokinase.

10. A method for producing the microorganism of claim 1, comprising introducing a nucleic acid having promoter activity into a microorganism so that the nucleic acid having promoter activity regulates transcription of a gene in the microorganism, wherein the nucleic acid having promoter activity comprises a) a nucleic acid molecule comprising the nucleotide sequence of SEQ ID NO: 1; or b) a nucleic acid molecule comprising a nucleotide sequence having at least 98% identity to the entire nucleotide sequence of SEQ ID NO: 1.

11. A method for increasing the transcription rate of a gene in a microorganism or causing the transcription of a gene in a microorganism compared with a microorganism in which the nucleic acid having promoter activity has not been introduced comprising regulating transcription of a gene in the microorganism by cultivating the genetically modified microorganism of claim 1.

12. The method of claim 11, where the nucleic acid having promoter activity is introduced into the genome of the microorganism so that transcription of one or more endogenous genes takes place under the control of the introduced nucleic acid having promoter activity.

13. The method of claim 12, wherein the regulating causes the transcription of the gene or results in an increased transcription rate of the gene in the microorganism compared with the corresponding wild type microorganism.

14. The method of claim 11, wherein the nucleic acid having promoter activity is introduced in a construct comprising the nucleic acid having promoter activity functionally linked to a nucleic acid to be transcribed in the microorganism.

15. The method of claim 14, wherein the regulating causes the transcription of the nucleic acid or results in an increased transcription rate of the nucleic acid in the microorganism compared with a microorganism in which the nucleic acid having promoter activity has not been introduced.

16. The method of claim 11, wherein the gene is selected from the group consisting of nucleic acids encoding a protein from the biosynthetic pathway of proteinogenic and non-proteinogenic amino acids, nucleic acids encoding a protein from the biosynthetic pathway of nucleotides and nucleosides, nucleic acids encoding a protein from the biosynthetic pathway of organic acids, nucleic acids encoding a protein from the biosynthetic pathway of lipids and fatty acids, nucleic acids encoding a protein from the biosynthetic pathway of diols, nucleic acids encoding a protein from the biosynthetic pathway of carbohydrates, nucleic acids encoding a protein from the biosynthetic pathway of aromatic compounds, nucleic acids encoding a protein from the biosynthetic pathway of vitamins, nucleic acids encoding a protein from the biosynthetic pathway of cofactors, and nucleic acids encoding a protein from the biosynthetic pathway of enzymes, where the genes may comprise further regulatory elements.

17. The method of claim 16, wherein the protein is selected from the group consisting of aspartate kinase, aspartate-semialdehyde dehydrogenase, diaminopimelate dehydrogenase, diaminopimelate decarboxylase, dihydrodipicolinate synthetase, dihydrodipicolinate reductase, glyceraldehyde-3-phosphate dehydrogenase, 3-phosphoglycerate kinase, pyruvate carboxylase, triosephosphate isomerase, transcriptional regulator LuxR, transcriptional regulator LysR1, transcriptional regulator LysR2, malate-quinone oxidoreductase, glucose-6-phosphate dehydrogenase, 6-phosphogluconate dehydrogenase, transketolase, transaldolase, homoserine O-acetyltransferase, cystathionine gamma-synthase, cystathionine beta-lyase, serine hydroxymethyltransferase, O-acetylhomoserine sulfhydrylase, methylenetetrahydrofolate reductase, phosphoserine aminotransferase, phosphoserine phosphatase, serine acetyltransferase, homoserine dehydrogenase, homoserine kinase, threonine synthase, threonine exporter carrier, threonine dehydratase, pyruvate oxidase, lysine exporter, biotin ligase, cysteine synthase I, cysteine synthase II, coenzyme B12-dependent methionine synthase, coenzyme B12-independent methionine synthase, sulfate adenylyltransferase subunit 1 and 2, phosphoadenosine-phosphosulfate reductase, ferredoxin-sulfite reductase, ferredoxin NADP reductase, 3-phosphoglycerate dehydrogenase, RXA00655 regulator, RXN2910 regulator, arginyl-tRNA synthetase, phosphoenolpyruvate carboxylase, threonine efflux protein, serine hydroxymethyltransferase, fructose-1,6-bisphosphatase, protein of sulfate reduction RXA077, protein of sulfate reduction RXA248, protein of sulfate reduction RXA247, protein OpcA, 1-phosphofructokinase, and 6-phosphofructokinase.

* * * * *